United States Patent
Arad et al.

(10) Patent No.: US 7,328,829 B2
(45) Date of Patent: Feb. 12, 2008

(54) PALM SIZE SURGICAL STAPLER FOR SINGLE HAND OPERATION

(75) Inventors: Michael Arad, Tel Aviv (IL); Boaz Harari, Tel Aviv (IL); Amir Perle, Haifa (IL); Dror Rosner, Holon (IL)

(73) Assignee: NiTi Medical Technologies Ltd., Netanya (IL)

( * ) Notice: Subject to any disclaimer, the term of this patent is extended or adjusted under 35 U.S.C. 154(b) by 59 days.

(21) Appl. No.: 11/446,870

(22) Filed: Jun. 5, 2006

(65) Prior Publication Data

US 2006/0219752 A1 Oct. 5, 2006

Related U.S. Application Data

(63) Continuation-in-part of application No. 11/010,866, filed on Dec. 13, 2004, now Pat. No. 7,121,446.

(51) Int. Cl.
*A61B 17/068* (2006.01)
(52) U.S. Cl. .............. 227/176.1; 227/175.4; 227/181.1; 227/180.1; 227/19
(58) Field of Classification Search ......... 227/176.1, 227/19, 175.4, 181.1, 180.1
See application file for complete search history.

(56) References Cited

U.S. PATENT DOCUMENTS

| | | | |
|---|---|---|---|
| 4,321,002 A | 3/1982 | Froehlich | |
| 4,520,817 A | 6/1985 | Green | |
| 4,633,861 A | 1/1987 | Chow et al. | |
| 4,633,874 A | 1/1987 | Chow et al. | |
| 4,767,044 A | 8/1988 | Green | |
| 4,892,244 A | 1/1990 | Fox et al. | |
| 5,040,715 A | 8/1991 | Green et al. | |
| 5,065,929 A | 11/1991 | Schulze et al. | |
| 5,071,430 A | 12/1991 | de Salis et al. | |
| 5,275,323 A | 1/1994 | Schulze et al. | |
| 5,318,221 A | 6/1994 | Green et al. | |
| 5,326,013 A | 7/1994 | Green et al. | |
| 5,350,400 A | 9/1994 | Esposito et al. | |
| 5,364,001 A | 11/1994 | Bryan | |
| 5,397,046 A * | 3/1995 | Savage et al. | 227/175.3 |
| 5,413,268 A | 5/1995 | Green et al. | |
| 5,415,334 A | 5/1995 | Williamson et al. | |
| 5,425,745 A | 6/1995 | Green et al. | |
| 5,431,322 A | 7/1995 | Green et al. | |
| 5,456,401 A | 10/1995 | Green et al. | |
| 5,465,894 A | 11/1995 | Clark et al. | |
| 5,472,132 A | 12/1995 | Savage et al. | |
| 5,476,206 A | 12/1995 | Green et al. | |

(Continued)

*Primary Examiner*—Brian Nash
(74) *Attorney, Agent, or Firm*—Pearne & Gordon LLP

(57) ABSTRACT

Palm-size staplers for surgical procedures are proposed. The staplers include cartridge and slider assemblies with the cartridge assembly containing staples. As the slider assembly advances step-wise incrementally it provides a staple ejection force causing ejection of staples. Optionally, a blade element may be included for cutting. An anvil member is operable in closed and open positions with respect to the cartridge assembly. When in a closed position, the anvil member holds a portion of tissue against the cartridge assembly, ejected staples passing through the held tissue. Actuation of the staplers is effected by a lever member. A locking mechanism, when in its locked position, holds the anvil member adjacent to the cartridge assembly allowing closure of the staple to occur. The devices are intended for one hand use.

20 Claims, 45 Drawing Sheets

U.S. PATENT DOCUMENTS

| | | |
|---|---|---|
| 5,480,089 A | 1/1996 | Blewett |
| 5,482,197 A | 1/1996 | Green et al. |
| 5,487,499 A | 1/1996 | Sorrentino et al. |
| 5,497,933 A | 3/1996 | DeFonzo et al. |
| 5,507,426 A | 4/1996 | Young et al. |
| 5,564,615 A | 10/1996 | Bishop et al. |
| 5,630,541 A | 5/1997 | Williamson et al. |
| 5,657,921 A | 8/1997 | Young et al. |
| 6,010,054 A | 1/2000 | Johnson et al. |
| 6,045,560 A | 4/2000 | McKean et al. |
| 6,250,532 B1 | 6/2001 | Green et al. |
| 6,264,087 B1 | 7/2001 | Whitman |
| 6,315,184 B1 | 11/2001 | Whitman |
| 6,443,973 B1 | 9/2002 | Whitman |
| 6,488,196 B1 | 12/2002 | Fenton, Jr. |
| 6,505,768 B2 | 1/2003 | Whitman |
| 6,517,565 B1 | 2/2003 | Whitman et al. |
| 6,817,508 B1 | 11/2004 | Racenet et al. |
| 6,953,138 B1 | 10/2005 | Dworak et al. |

\* cited by examiner

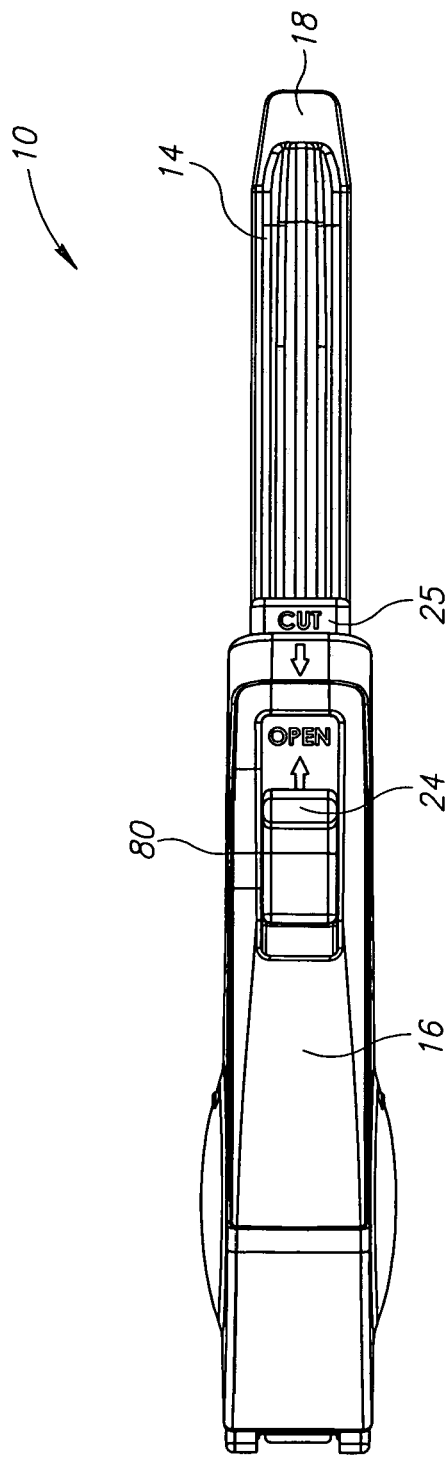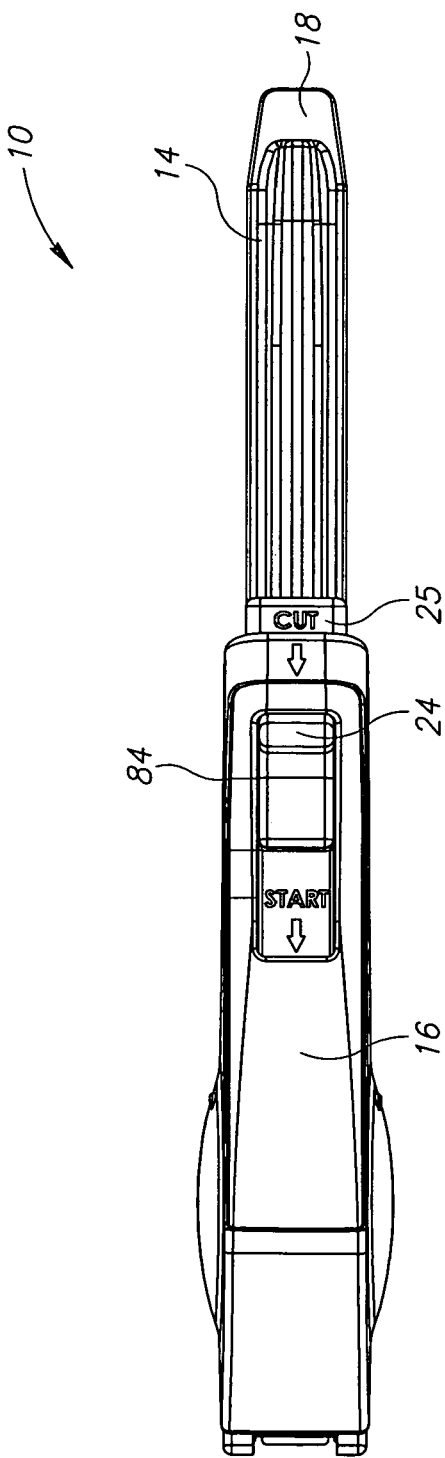

PALM SIZE SURGICAL STAPLER FOR SINGLE HAND OPERATION

CROSS REFERENCE TO RELATED APPLICATION

This application is a continuation-in-part of U.S. patent application Ser. No. 11/010,866 filed Dec. 13, 2004 originally titled "Tissue Stapler" and now titled "Palm Size Surgical Stapler for Single Hand Operation".

FIELD OF THE INVENTION

The present invention relates to staplers and a method for use thereof, particularly tissue staplers.

DEFINITION

Throughout the specification and claims below, the term "stapler" means a device which accomplishes stapling of tissue, and which may optionally also be provided with cutting or resection capabilities, by means of a blade or a knife.

BACKGROUND OF THE INVENTION

Surgical stapling devices for performing gastrointestinal surgery are known. Generally, these devices are categorized by their method of use and application. One type of device is designed for use under open surgery conditions, while a second type of device is designed for use in laparoscopic or endoscopic surgery. Included in the latter is the surgical method known as hand-assisted laparoscopic surgery (HALS).

HALS is a bridge method between open and laparoscopic surgical methods. In HALS, a special hand port is installed through a small (4-6 cm.) incision in the body. The hand port enables the surgeon to insert one hand into the abdominal cavity to assist with the laparoscopic procedure thereby retaining finger sensitivity which is lost in full laparoscopic procedures. HALS also enables the surgeon to insert hand operated palm size instruments through the hand port.

Prior art open and laparoscopic surgical devices are based on a plurality of mechanisms. Each device includes one or more specific improvements, such as means for reducing the risk of using the device when the staple cartridge is empty. These open and laparoscopic surgical devices include instruments which may be mechanically, gas or electrically driven.

Prior art laparoscopic instruments are generally similar to open surgery devices. However, they typically have an extended or elongated body with a pair of jaws connected to the distal end of the elongated portion. These jaws are pivotally mounted at the device's distal end for movement toward and away from each other while gripping body tissue. Many variations of this basic design exist with each device providing specific added features, such as articulation of the distal operating mechanism. As with open surgery devices, these instruments may be driven by various types of motive power sources.

As noted above, surgical instruments for the surgical stapling and excising of tissue are well known in the art. These include, for example, U.S. Pat. No. 4,520,817 to Green; U.S. Pat. No. 4,633,861 to Chow, et al.; U.S. Pat. No. 4,633,874 to Chow, et al.; U.S. Pat. No. 4,892,244 to Fox, et al.; U.S. Pat. No. 5,065,929 to Schulze, et al.; and U.S. Pat. No. 5,275,323 to Schulze, et al. Laparoscopic and endoscopic devices are disclosed in a number of patents. These include inter alia U.S. Pat. No. 5,071,430 to de Salis, et al.; U.S. Pat. No. 5,040,715 to Green, et al.; U.S. Pat. Nos. 5,318,221, 5,413,268, 5,425,745 and 5,476,206, to Green, et al.; U.S. Pat. No. 5,326,013 to Green, et al.; U.S. Pat. No. 5,364,001 to Bryan; U.S. Pat. No. 5,456,401 to Green, et al.; U.S. Pat. Nos. 5,397,046 and 5,472,132 to Savage, et al.; U.S. Pat. No. 5,482,197 to Green, et al.; U.S. Pat. No. 6,250,532 to Green, et al.; U.S. Pat. No. 5,487,499 to Sorrentino, et al.; U.S. Pat. Nos. 5,476,206 and 5,431,322 to Green, et al.; U.S. Pat. Nos. 5,507,426 and 5,657,921 to Young, et al.; U.S. Pat. No. 6,010,054 to Johnson, et al.; U.S. Pat. No. 6,045,560 to McKean, et al.; U.S. Pat. No. 6,264,087 to Whitman; U.S. Pat. No. 6,505,768 to Whitman; U.S. Pat. No. 6,517,565 to Whitman, et al.; U.S. Pat. No. 6,315,184 to Whitman; U.S. Pat. No. 6,443,973 to Whitman; and U.S. Pat. No. 6,488,196 to Fenton, Jr.

The above-mentioned prior art devices provide a wide range of apparatuses and techniques for stapling, cutting, and excising tissue, typically a portion of the bowel. Generally, these devices require the surgeon to use both hands. In addition, as noted, the laparoscopic devices discussed in the above patents generally have elongated elements for entry into the body cavity while being actuated by the operator outside the cavity.

There appears to be a lack of compact simple devices for single-hand use where the device can be positioned and actuated totally within the abdominal cavity. Such a device is essential for use in HALS. Additionally, there does not appear to be a simple single-hand use device which allows for interrupting the stapling, and optionally the cutting, operation, repositioning the tissue being stapled, and optionally cut, and then recommencing the stapling, and optional cutting, procedure. This is very important in stapling and/or resecting the correct part of the diseased tissue and, in some applications, for resections where the cut must be an essentially non-linear cut.

SUMMARY OF THE INVENTION

It is an object of the present invention to provide a hand-held stapler for surgical procedures which can be operated at all times by just a single hand of the user. The device is suitable for open and laparoscopic surgery, including hand-assisted laparoscopic surgery (HALS).

It is another object of the present invention to provide a stapler for surgical procedures which can be positioned and operated entirely within the body cavity.

It is yet a further object of the present invention to provide a stapler for surgical procedures which clamps the tissue to be stapled and resected before stapling and cutting begins. However, the stapler can be repositioned around the tissue to be stapled during the surgery by a series of single-hand operations.

Another object of the present invention is to provide a method for stapling, and optionally cutting, tissue during surgical procedures wherein all the operations are effected using one hand of the user. The method also allows for the repositioning of the stapler around the tissue being stapled and resected during the stapling and optional cutting operations without removing the stapler from the body cavity.

A further object of the present invention is to provide a stapler for surgical procedures wherein the staples remain substantially planar during and after stapling.

It is a further object of the present invention to provide a tissue stapler wherein the registration of the anvil member and cartridge assembly in which are positioned staples to be crimped is increased.

It is an object of the present invention to provide a tissue stapler for one hand operation where the force needed to operate the stapler is reduced.

It is another object of the present invention to provide a tissue stapler which is structurally uncomplicated and operationally usable with one hand.

All these objectives and others discussed below are accomplished in accordance with the principles of the invention by providing a surgical instrument which is manually operated. The surgical device in accordance with embodiments of the present invention is a surgical stapler adapted for inserting two or more longitudinal rows of staples. The stapler may optionally include a blade element for making an incision in body tissue between rows of staples. The stapler may find particular use in removing all or a portion of an organ, such as the bowel, appendix, gallbladder, uterus, etc.

In one aspect of the present invention there is provided a palm-size stapler for hand-assisted laparoscopic and open surgery. The device includes a chassis member and an anvil member. The chassis member supports at least the following elements: i) a cartridge assembly for containing two or more rows of staples and ii) a slider assembly operative to slidably move along a predetermined path with respect to the cartridge assembly, thereby providing a predetermined staple ejection force causing the ejection of staples from the cartridge assembly. The slider assembly includes one or more staple ejector elements aligned with the two or more rows of staples for causing ejection of the staples. The anvil member is operable in closed and open positions with respect to the cartridge assembly. When in a closed position, the anvil member is spaced from the cartridge assembly so that a portion of tissue is held between it and the cartridge assembly. The anvil member also allows closure of staples ejected from the cartridge assembly in response to the predetermined staple ejection force provided by the slider assembly. The stapler also includes a lever member mounted to the chassis member which is pivotably movable with respect to the cartridge assembly. The stapler further includes one or more selector elements disposed on the stapler, the one or more selector elements being operated while in the grip of a single hand of an operator. These elements act to select an operational mode of the stapler in response to the operator selected positioning of the one or more selector elements. The stapler also includes a locking linking mechanism operable in locked and unlocked positions. The linking mechanism is in operative association with the anvil member and also with the one or more selector elements. The mechanism is brought to its locked position when the lever member is brought down and presses on it. When the linking mechanism is in its locked position the anvil member is brought to its closed position and held adjacent to the cartridge assembly. This allows closure of staples in the portion of tissue held between the cartridge assembly and the anvil member as the slider assembly advances step-wise incrementally, ejecting staples into the tissue with each step.

In another embodiment of the stapler of the present invention, the stapler further includes an incremental drive mechanism operative to selectively engage with and to provide a predetermined driving force to the slider assembly causing an incremental step-wise sliding motion of the slider assembly. The locking linking mechanism is in its unlocked position when the drive mechanism is operative. The incremental drive mechanism allows for interruption of the operation of the stapler during surgery and repositioning of the tissue being stapled. Interruption and repositioning is effected when the one or more selector elements are brought to an operational mode where the lever member is operative to release the anvil member from its closed position.

In another aspect of the present invention there is provided a second palm-size stapler for hand-assisted laparoscopic and open surgery. The stapler includes a chassis member and an anvil member. The chassis member supports at least the following elements: i) a cartridge assembly for containing two or more rows of staples and ii) a slider assembly operative to slidably move along a predetermined path with respect to the cartridge assembly, thereby providing a predetermined staple ejection force causing the ejection of staples from the cartridge assembly. The slider assembly includes one or more staple ejector elements aligned with the two or more rows of staples for causing ejection thereof. The anvil member is operable in closed and open positions with respect to the cartridge assembly. When in a closed position, the anvil member is spaced from the cartridge assembly so that a portion of tissue is held between the anvil and the cartridge assembly. The anvil member also allows closure of staples ejected from the cartridge assembly in response to the predetermined staple ejection force provided by the slider assembly. Included is one or more selector elements disposed on the stapler. The one or more selector elements are operated while in the grip of a single hand of an operator. The one or more selector elements select an operational mode of the stapler in response to operator selected positioning of the selector elements. The stapler also includes a lever member mounted to the chassis member, the lever member being pivotably movable with respect to the cartridge assembly. The stapler also includes an incremental drive mechanism in operational association with the slider assembly. The drive mechanism operates to selectably engage with and to provide a predetermined driving force to the slider assembly causing an incremental step-wise sliding motion of the slider assembly. The incremental drive mechanism also allows for interruption of the operation of the device during surgery and repositioning of the portion of tissue being stapled. Interruption occurs when the one or more selector elements are brought to an operational mode where the lever member operates to release the anvil member from its closed position.

In another embodiment of the second stapler, the stapler further includes a locking linking mechanism which operates in locked and unlocked positions. The linking mechanism is in operative association with the anvil member and also with the one or more selector elements. The locking linking mechanism is brought to its locked position when the lever member is brought down pressing on it. When in its locked position the locking linking member holds the anvil member in its closed position proximate to the cartridge assembly.

In another embodiment of staplers constructed according to the present invention, the one or more selector elements are operable to select at least one of a plurality of operative modes. In some of these embodiments the one or more selector elements is operable to select any of a first, second and third operative mode, wherein a) in the first operative mode, the lever member is operative to move the anvil member into a position proximal to the cartridge assembly, thereby facilitating closure of staples ejected there against, b) in the second operative mode, the lever member is operative to transform a squeezing force, applied repetitively thereto, into the predetermined driving force of the incremental drive mechanism so as to slidably move the slider assembly with an incremental stepped action in the predetermined path relative to the chassis member, thereby to provide the predetermined staple ejection force; and c) in the third operative mode, the lever member is operative to release the anvil member from its closed position, where the anvil member is proximate to the cartridge assembly, to its open position where the anvil member is distant from the cartridge assembly.

In another embodiment of staplers constructed according to the present invention, the staplers further include a release mechanism comprising a guiding pin attached to the incremental drive mechanism. The pin rides in a groove having two or more legs positioned in the chassis member. The guiding pin rides in one leg of the two or more legs when the anvil member is in its closed position and held proximate to the cartridge assembly and rides in another leg of the two or more legs when the anvil member is in its open position and held distant from the cartridge assembly. The pin moves from one leg to another as the incremental drive mechanism is selectively engaged with the slider assembly.

Additional embodiments of the staplers constructed according to aspects of the present invention are possible. In a further embodiment of the staplers, the incremental drive mechanism is selected from a group of mechanisms consisting of a pusher-ratchet mechanism, a pulley mechanism and a gear mechanism. In some embodiments of the pusher-ratchet mechanism, the mechanism includes a pusher and a ratchet mechanism where the pusher is positioned obliquely to the ratchet mechanism and the ratchet mechanism is part of the slider assembly. In some embodiments, the pusher is operatively associated with a slidable tooth rack so as to incrementally move the slider assembly of the device along a predetermined path in a stepped fashion.

In yet another embodiment of the staplers of the present invention, the anvil member has proximal and distal surfaces with respect to the cartridge assembly and a plurality of recesses positioned on the proximal surface. The recesses are in registration with staples in a cartridge in the cartridge assembly and configured to hold the staples in a planar configuration during and subsequent to crimping of the staples. In some of the anvil recess embodiments, the recesses are funnel-shaped with each recess having a rounded end and a wide end. The funnel-shaped recesses may have one or more of the following characteristics when using staples of a given cross section formed from a wire with a given largest cross sectional dimension: a) the wide end of the recess ranges in size from about three to about six times the largest cross sectional dimension of the wire from which the staples are formed; and b) the rounded end of each of the recesses has a radius of curvature of from about half the largest cross sectional dimension to about the largest cross sectional dimension of the wire from which the staples are formed. In other embodiments employing anvil recesses the recesses may have a bottom surface and an angle formed between the bottom surface and the proximal surface of the anvil ranges from about 0 to about 5 degrees. In these embodiments, when the wire has a circular cross section, the largest cross sectional dimension is a diameter of the wire.

In further embodiments of the staplers of the present invention, the locking linking mechanism includes a plurality of links. In some of these embodiments the locking linking mechanism locks when the plurality of links are in a substantially linear configuration. In other embodiments, the locking linking mechanism locks when the plurality of links are in an over center position. In yet other embodiments, the locking linking mechanism locks when the plurality of links are in an under center position. In some embodiments, the locking linking mechanism locks when held in place by a latch.

In yet other embodiments of the staplers of the present invention, a tab is positioned on a link of the locking linking mechanism, the tab preventing the pusher from engaging with the slider assembly.

In another embodiment of the staplers of the present invention, the one or more selector elements are disposed on the lever member.

In yet another embodiment of the present invention the stapling device may include a blade element to selectively cut the held portion of tissue. The blade element may be attached to the slider assembly. In embodiments with a blade element, the blade element may advance step-wise incrementally cutting through the held portion of stapled tissue as the slider assembly advances step-wise incrementally.

In yet another aspect of the present invention, a method is provided for performing tissue stapling during hand-assisted laparoscopic or open surgery. The method includes the following steps:

a) inserting a stapler through an incision in a body cavity b) positioning the stapler so that an anvil member and a cartridge assembly of the stapler are arranged about a preselected tissue section to be excised;

c) closing and locking the stapler so as to hold a preselected tissue section between the anvil member and the cartridge assembly of the stapler; and d) repeatedly operating a lever member of the stapler so as to incrementally and in a stepped fashion move a slider assembly of the stapler along a predetermined path, thereby to staple the preselected tissue section at a predetermined position, wherein all of the above steps are performed by the operator while holding the device in one hand.

In another embodiment of the method, following the step of repeatedly operating there is included the step of opening the stapler from about the preselected tissue section so that the anvil member and cartridge assembly are in a mutually spaced apart position releasing the held tissue section. In some of these embodiments, the method, further includes repeating the steps of positioning and closing at any point during the surgery so as to reposition the stapler about the tissue being stapled and then continuing with the step of repeatedly operating. In some embodiments of the method, the method further includes the steps of positioning, closing and repeatedly operating where the slider assembly moves along a second preselected path on the tissue so that a second stapling line can be formed along a second predetermined position.

In another embodiment of the method, the step of repeatedly operating further includes the step of cutting the stapled preselected tissue, when the stapler additionally includes a blade element. In yet another embodiment of the method, the method further includes the steps of positioning, closing and repeatedly operating where the slider assembly moves along a second preselected path on the tissue so that a second cut can be effected along a second predetermined position, thereby totally severing the tissue, allowing for its withdrawal from the body cavity. In some of these embodiments, the method further includes the step of anastomosing the two ends of tissue from which the severed tissue was detached.

When the step of anastomosing is effected, anastomosis may be performed using the same stapler as that used in the steps of positioning, closing and repeatedly operating. In other instances, anastomosis may be performed using a device other than the stapler used in the steps positioning, closing and repeatedly operating.

In some embodiments, of the method according to the present invention, the tissue being stapled and/or resected is bowel tissue and the body cavity is the abdominal cavity.

In a further embodiment of the method of the present invention the step of inserting is effected while the anvil member of the device is held proximal to the cartridge assembly.

In yet another aspect of the present invention there is provides an anvil for use in a stapling device. The anvil has proximal and distal surfaces with respect to a staple cartridge containing a plurality of staples, and the proximal surface has a plurality of funnel-shaped recesses. Each recess has a wide end and a rounded end. The recesses are in registration with the staples in the cartridge and sized and configured for receiving staples during the crimping process so that the staple will retain a substantially planar shape after crimping.

In a further embodiment of the anvil having recesses, the anvil is for use in stapling body tissue.

In an additional embodiment of the anvil, the recesses have at least one of the following characteristics when using staples of a given cross section formed from wire of a given largest cross sectional dimension:

a) the wide end of the recess ranges in size from about three to about six times the largest cross sectional dimension of the wire from which the staples are formed; and b) the rounded end of each of the recesses has a radius of curvature of from about half the largest cross sectional dimension to about the largest cross sectional dimension of the wire from which the staples are formed.

When the wire has a circular cross section, the largest cross sectional dimension is the diameter of the wire.

In another embodiment of the anvil, each of the recesses has a bottom surface and an angle formed between the bottom surface and the proximal surface of the anvil ranges from about 0 to about 5 degrees.

In yet another aspect of the present invention, there is provided a palm-size stapler for hand-assisted laparoscopic and open surgery comprising:

a) a chassis member in which at least the following elements are supported:
   i) a cartridge assembly for containing at least two rows of staples; and
   ii) a slider assembly operative to slidably move along a predetermined path with respect to the cartridge assembly, thereby to provide a predetermined staple ejection force to cause the ejection of staples from the cartridge assembly, the slider assembly including:
     at least one staple ejector element aligned with the at least two rows of staples for causing ejection of the staples;

b) an anvil member operable in closed and open positions with respect to the cartridge assembly and when in a closed position the anvil member is spaced from the cartridge assembly so as to hold a portion of tissue to be stapled therebetween and to allow closure of staples ejected into the tissue from the cartridge assembly in response to the predetermined staple ejection force provided by the slider assembly;

c) a lever member mounted to the chassis member pivotably movable with respect to the cartridge assembly and operable by using one hand; and d) a locking mechanism operable in locked and unlocked positions and in operative association with the anvil member, the locking mechanism being brought to its locked position when the lever member is pressed and brought down, and when the locking mechanism is brought to its locked position the anvil member is brought to and locked in its closed position and held adjacent to the cartridge assembly during subsequent operation, thereby to allow closure of staples in the portion of the tissue held between the cartridge assembly and the anvil member as the slider assembly advances step-wise incrementally ejecting staples into the tissue with each step.

In yet another embodiment of this last aspect of the present invention, the stapler further includes an incremental drive mechanism operative to engage with and to provide a predetermined driving force to the slider assembly which causes an incremental step-wise sliding motion of the assembly. The incremental drive mechanism allows for interruption of the operation of the stapler during surgery and thereby also allows for repositioning of the tissue being stapled. When the locking mechanism is released by a release mechanism in operative association with the locking mechanism, the anvil member is brought to its open position from its closed position. The release mechanism is operated by use of one hand, the hand which performs all the operations when using the stapler. In some variations of this last embodiment, the anvil member may be connected rigidly to an anvil frame forming therewith an extended substantially rigid compound anvil member. The compound anvil extends from an axis pin positioned near the proximal end of the stapler to the distal end of the anvil member. The compound anvil member is hingedly mounted on the axis pin. In some cases, the locking mechanism further comprises a pusher pin, a locking link and an anvil locking element. The locking link is in operational engagement with the compound anvil member allowing scissor-like motion between these two elements. The pusher pin is positioned on the lever member. The pusher pin moves downward in a direction generally toward the slider assembly when the lever member is depressed. The pusher pin moves upward in a direction generally away from the slider assembly when the lever is released. The pusher pin is operative, when moving downward, to push the locking link against the anvil locking element so as to become engaged with it. As a result of this engagement, the anvil member is held in its closed position after depression of the lever member until activation of the release mechanism. The incremental drive mechanism may be a pusher-ratchet mechanism that comprises a.) a pusher positioned obliquely to the ratchet mechanism and b.) a ratchet mechanism. The ratchet mechanism is formed as part of the slider assembly, and the pusher is mounted for pivoting about an axis extending substantially transversally through the pusher. The axis also extends substantially through the pusher pin. The pusher is operatively associated with a slidable tooth rack so as to incrementally move the slider assembly of the stapler along a predetermined path in a stepped fashion.

In some embodiments of the stapler in this last aspect of the invention, the stapler's cartridge assembly is configured to hold a cartridge of staples, and the anvil member has proximal and distal surfaces with respect to the cartridge assembly. The proximal surface includes a plurality of recesses formed to be in registration with the staples in the cartridge in the cartridge assembly. The recesses are configured to retain the plurality of staples in a planar arrangement during and subsequent to crimping of the staples.

In yet another embodiment of this last aspect of the invention, the stapler further includes a blade element attached to the slider assembly. The blade element is operative to advance in incremental steps corresponding to the advance of the slider assembly in incremental steps. The blade element thereby incrementally cuts through the tissue held between the anvil member and the cartridge assembly in accordance with the advance of the slider assembly.

In another embodiment of this last aspect of the present invention, the locking mechanism of the stapler further comprises a pusher pin, a locking link and an anvil locking element. The locking link is in operational engagement with the anvil member allowing scissor-like motion therebetween. The pusher pin is positioned on the lever member. The pusher pin moves downward in a direction generally toward the slider assembly when the lever member is depressed, and the pin moves upward in a direction generally away from the slider assembly when the lever is released. The pusher pin is operative, when moving downward, to push the locking link against the anvil locking element so as to become engaged therewith. This holds the anvil member in the closed position after depression of said lever member until activation of a release mechanism which is in operational communication with the anvil locking element and which operates to release the locking mechanism bringing it from its locked to its unlocked position.

In another embodiment of this last aspect of the present invention, the incremental drive mechanism of the stapler is a pusher-ratchet mechanism that comprises a.) a pusher positioned obliquely to said ratchet mechanism and b.) a ratchet mechanism. The ratchet mechanism is formed as part of the slider assembly, and the pusher is mounted for pivoting about an axis extending substantially transversally therethrough. The axis also extends substantially through a pusher pin positioned on said lever member.

In yet another aspect of the present invention there is provided a palm-size stapler for hand-assisted laparoscopic and open surgery comprising:
 a) a chassis member in which at least the following elements are supported:
  i) a cartridge assembly for containing at least two rows of staples; and
  ii) a slider assembly operative to slidably move along a predetermined path with respect to the cartridge assembly, thereby to provide a predetermined staple ejection force to cause the ejection of staples from the cartridge assembly, the slider assembly including:
   at least one staple ejector element aligned with the at least two rows of staples for causing ejection of the staples;
 b) a lever member mounted to the chassis member pivotably movable with respect to the cartridge assembly and operable by using one hand;
 c) an anvil member operable in closed and open positions with respect to the cartridge assembly and when in closed position the anvil member is spaced from the cartridge assembly so as to hold a portion of tissue being stapled therebetween, and to allow closure of staples ejected into the tissue from the cartridge assembly in response to the predetermined staple ejection force provided by the slider assembly; and
 d) an incremental drive mechanism in operational association with the slider assembly, the drive mechanism operative to engage with and to provide a predetermined driving force to the slider assembly causing an incremental step-wise sliding motion thereof, the incremental drive mechanism also allowing for interruption of the operation of the device during surgery and allowing repositioning of the portion of tissue being stapled.

In an embodiment of this last aspect of the present invention, the stapler further includes a locking mechanism operable in locked and unlocked positions. The locking mechanism is in operative association with the anvil member. The locking mechanism is brought to its locked position when the lever member is pressed and brought down, and when the locking mechanism is brought to its locked position the anvil member is brought to its closed position. In the closed position, the anvil member is held adjacent to the cartridge assembly during subsequent stapler operation. It remains in the closed position until a release mechanism, which is in operative association with the locking mechanism, is activated unlocking the locking mechanism. This allows the anvil member to pivot away from the cartridge assembly.

In some variations of this last embodiment, the anvil member is connected rigidly to an anvil frame thereby to form therewith an extended substantially rigid compound anvil member.

The compound anvil member extends from an axis pin positioned near the proximal end of the stapler to the distal end of the anvil member, and the compound anvil member is hingedly mounted on the axis pin. In some cases, the locking mechanism further comprises a pusher pin, a locking link and an anvil locking element. The locking link is in operational engagement with the compound anvil member allowing scissor-like motion between them. The pusher pin is positioned on the lever member. The pusher pin moves downward in a direction generally toward the slider assembly when the lever member is depressed. The pin moves upward in a direction generally away from the slider assembly when the lever is released. The pusher pin is operative when moving downward to push the locking link against the anvil locking element so as to effect engagement between them. This engagement holds the anvil member in the closed position after depression of the lever member until activation of the release mechanism. The release mechanism operates to release the locking mechanism bringing it from its locked to its unlocked position. The incremental drive mechanism may be a pusher-ratchet mechanism that comprises a.) a pusher positioned obliquely to the ratchet mechanism and b.) a ratchet mechanism. The ratchet mechanism is formed as part of the slider assembly, and the pusher is mounted for pivoting about an axis extending substantially transversally through the pusher. The axis also extends substantially through the pusher pin. The pusher is operatively associated with a slidable tooth rack so as to incrementally move the slider assembly of the stapler along a predetermined path in a stepped fashion.

In some embodiments of the stapler in this last aspect of the invention, the cartridge assembly is configured to hold a cartridge of staples. The anvil member has proximal and distal surfaces with respect to the cartridge assembly, the proximal surface having a plurality of recesses formed to be in registration with the staples in the cartridge in the cartridge assembly. The recesses are configured to retain the plurality of staples in a planar arrangement during and subsequent to crimping of the staples.

In yet another embodiment of this last aspect of the invention, the stapler further includes a blade element attached to the slider assembly. The blade element is operative to advance in incremental steps corresponding to the advance of the slider assembly in incremental steps. The blade element thereby incrementally cuts through the tissue held between the anvil member and the cartridge assembly in accordance with the advance of the slider assembly.

In still another embodiment of this last aspect of the present invention, the incremental drive mechanism is a pusher-ratchet mechanism that comprises a.) a pusher positioned obliquely to the ratchet mechanism and b.) a ratchet mechanism. The ratchet mechanism is formed as part of the slider assembly, and the pusher is mounted for pivoting about an axis extending substantially transversally therethrough and also extending substantially through a pusher pin positioned on the lever member.

In another embodiment of this last aspect of the present invention, the stapler includes a locking mechanism which comprises a pusher pin, a locking link and an anvil locking element. The locking link is in operational engagement with the anvil member allowing scissor-like motion between the locking link and the anvil member. The pusher pin is positioned on the lever member. The pusher pin moves downward in a direction generally toward the slider assembly when the lever member is depressed, and the pin moves upward in a direction generally away from the slider assembly when the lever is released, The pusher pin is operative when moving downward to push the locking link against the anvil locking element so as to become engaged therewith. This holds the anvil member in the closed position after depression of the lever member until activation of a release mechanism. The release mechanism is in operational communication with the anvil locking element and operates to release the locking mechanism bringing it from its locked to its unlocked position.

BRIEF DESCRIPTION OF THE DRAWINGS

The present invention will be more fully understood and its features and advantages will become apparent to those skilled in the art by reference to the ensuing description, taken in conjunction with the accompanying drawings, in which:

FIGS. 8, 9 and 10 are top plan views of the stapler illustrating three operational mode positions of a selector element;

Similar elements in the Figures are numbered with similar reference numerals.

DETAILED DESCRIPTION OF THE PREFERRED EMBODIMENTS

In the ensuing description, there is described a stapler which is constructed with elements to effect both stapling and cutting. While the present invention primarily contemplates devices that are constructed to effect stapling and cutting, stapling devices without cutting elements or blade elements are also contemplated.

Accordingly, all the embodiments described below are equally applicable to a stapling device alone since the incremental drive mechanism and locking linking mechanism described herein below do not rely on the cutting function, per se.

When used in the specification and claims herein, "palm-size" is intended to indicate the general size of the device. Its size is about the size of the hand of a typical adult male or female and it is this size that allows for its one hand use.

The present invention relates to a stapler for performing open and hand-assisted laparoscopic surgery (HALS). HALS is generally carried out employing a hand port, which provides entry into the patient's abdominal cavity and facilitates continuous inflation of the cavity. The surgeon grasps the generally palm-size stapler of the present invention with one hand and works directly within the cavity.

The stapler of the present invention is useful in resecting various types of tissue, particularly bowel tissue. The discussion herein below will describe the use of the stapler in resecting bowel tissue. It should readily be understood by one skilled in the art that such use is exemplary only and should not be deemed limiting as to other types of tissue.

The stapler of the present invention allows for stapling and cutting tissue, while permitting interruption of the resection at any point during the surgery and repositioning the stapler with respect to the tissue to be excised. At any point during the resection of the tissue, the surgeon can stop the stapling and cutting operation, open the stapler, rotate the device, re-clamp the tissue and continue stapling and cutting in the same or in a different direction.

Stapling is effected by an incremental drive mechanism, including but not limited to, a step-like ratchet mechanism. The stapler includes a locking linking mechanism which locks an anvil member in a position proximate to a cartridge assembly. The mechanism uses the relatively small forces produced by a single hand and magnifies them sufficiently to ensure proper clamping of the tissue between the anvil and a cartridge assembly.

Other features of the stapler of the present invention include:
  A mechanism which prevents the reuse of a spent staple cartridge.
  An anvil member formed to include funnel-shaped recesses which guide the staple into a crimped B-shape while ensuring that the staple remains essentially in one plane during and after crimping.

Figure 1:
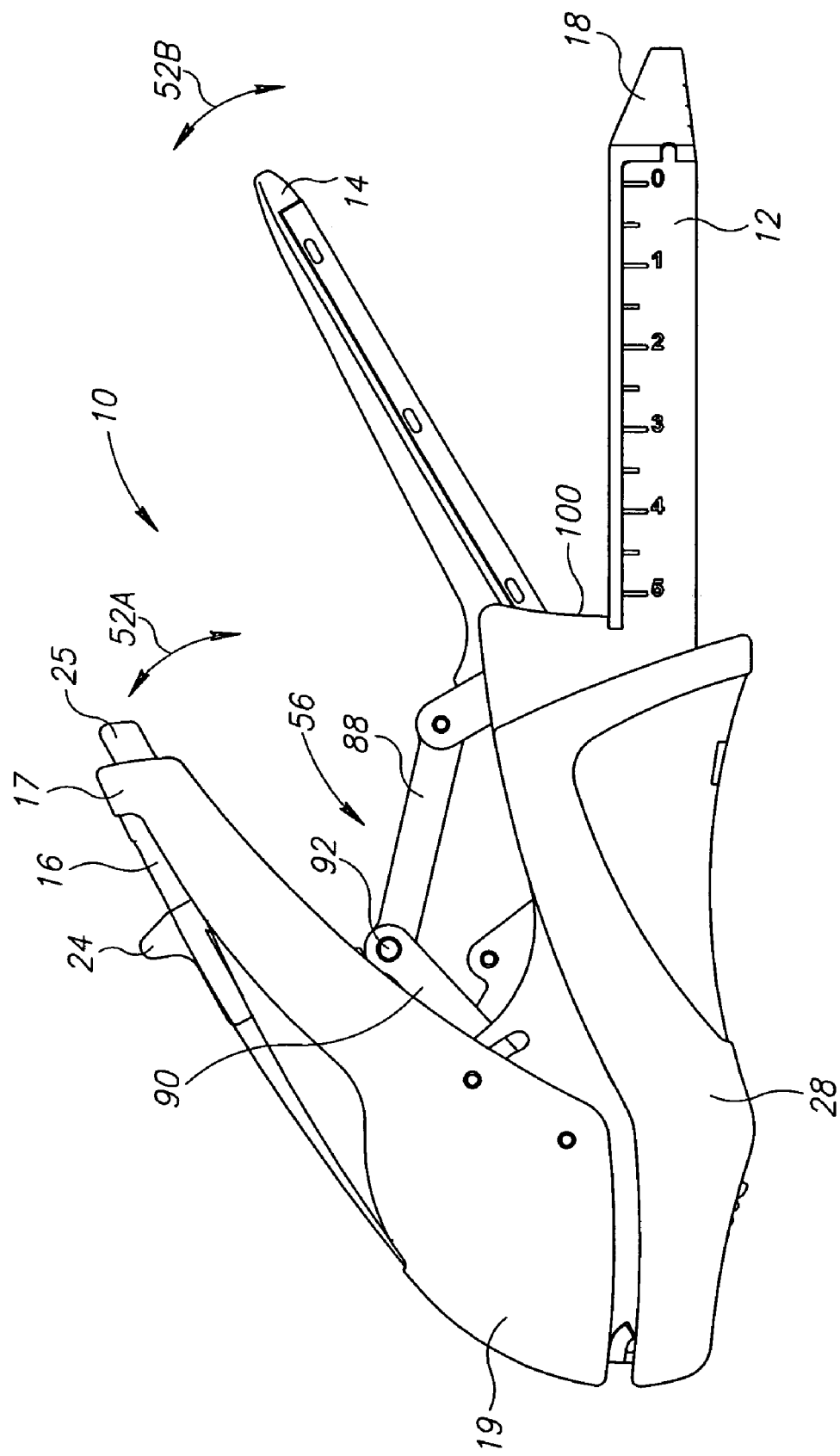
FIG. 1 is a side view of a stapler.
Figure 2:
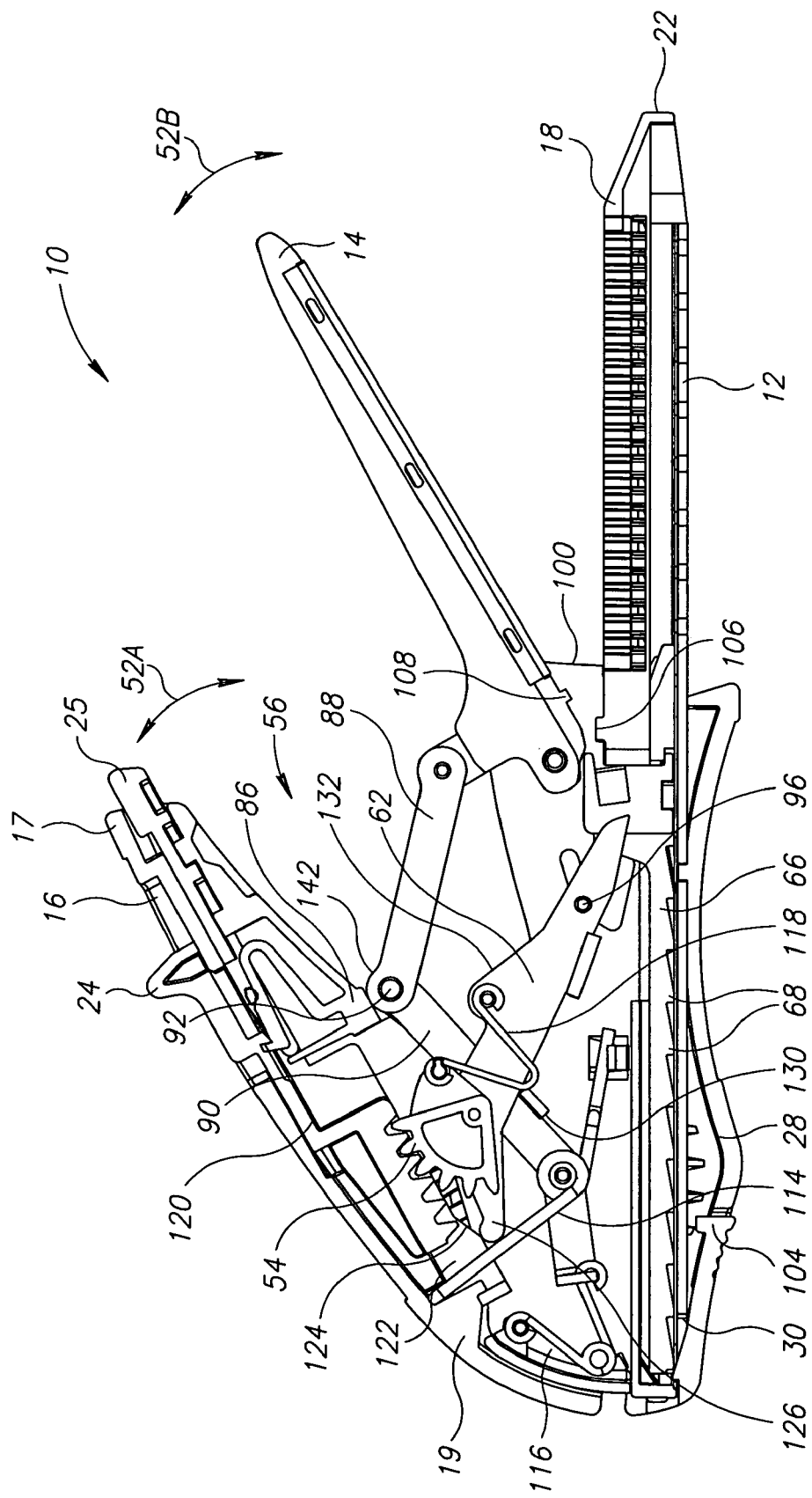
FIG. 2 is a partial cross-sectional view of the operating mechanism of the stapler shown in FIG. 1.

Reference is made to FIGS. 1 and 2 where a side view of a stapler 10 and a partial cross-sectional view of the operating mechanism of stapler 10, constructed according to an embodiment of the present invention, are shown. Reference is also made to FIGS. 3A-3C and 4 where a perspective view, two exploded perspective views and a side view of cartridge assembly 18, respectively, are shown. In what is described herein below, "proximal" relates to the side of the stapler or element of the stapler closest to the user, while "distal" refers to the side of the stapler or element of the stapler furthest from the user. To properly orient the position of the user, element 18 in FIG. 1 is positioned near the distal end of stapler 10 while element 19 is located near its proximal end.

Stapler 10 includes a chassis member 12, to which are attached anvil member 14 and lever member 16. Both anvil 14 and lever 16 members are pivoting members as indicated by arrows 52B and 52A respectively. Operatively associated with lever member 16 and disposed near its distal end 17, is a selector element 24. FIG. 1 includes a chassis cover member 28, which obscures additional elements readily seen in FIG. 2. It should be noted that chassis member 12 includes in addition to an elongated end which is readily seen in FIG. 2, a second larger, non-elongated, shaped proximal end that is obscured by chassis cover 28 of FIG. 1 and not shown in FIG. 2. The entire chassis member 12 can best be seen in FIG. 3B which will be discussed below.

As shown in FIG. 2, lever member 16 is mounted on main spring 114 and can pivot relative to chassis member 12, as indicated by arrow 52A. Main spring 114 keeps lever member 16 open by providing a biasing tension thereto. Disposed near the proximal end 19 of lever member 16 is a selector mechanism 54, which is operatively connected to selector element 24. During a surgical procedure, the user grasps stapler 10 in one hand and operates selector element 24 with a finger of that hand.

Stapler 10 is operational in three modes, these modes being discussed in greater detail below. Selector element 24 determines in which of the three operational modes stapler 10 is to be operated. By moving selector element 24 to one of three different positions, the operational mode in which stapler 10 is to be operated is determined and may be varied.

Locking linking mechanism 56 is comprised of locking front 88 and back 90 links joined at locking linking mechanism pin 92. Locking front link 88 is attached to anvil member 14 and when front 88 and back 90 links are extended so as to form a substantially linear configuration (as shown in FIGS. 12-17 which will be described below), anvil member 14 pivots as indicated by arrow 52B toward chassis member 12. As will be described below and discussed in conjunction with the relevant Figures to be presented, chassis member 12 inter alia supports slider assembly 20 and cartridge assembly 18 which ride therein.

Locking back link 90 is attached to locking linking mechanism spring 116. Locking linking mechanism spring 116 assists in controlling locking linking mechanism 56 so that anvil member 14 may be in its open or closed position as described herein.

In our discussion, "closed" with respect to lever member 16 indicates that member 16 has rotated toward chassis member 12 as shown by arrow 52A and is proximate to chassis member 12; "open" indicates that lever member 16 is in a position distant from chassis member 12 as shown in FIGS. 1 and 2. Similarly, the term "closed" with respect to anvil member 14 indicates that it has rotated in a direction toward chassis member 12 as shown by arrow 52B and is held proximate to chassis member 12, while "open" indicates that anvil member 14 is in a position distant from chassis member 12 as shown in FIGS. 1 and 2.

Selector element 24 is in mode transferring association with selector mechanism 54 through mode transfer element 120. Proximal end 122 of mode transfer element 120 has grooves which engage teeth on selector mechanism 54.

When selector element 24 is moved in the proximal direction to its stapling and cutting position, selector mechanism 54, which is spring loaded by selector spring 118, turns in a counter-clockwise direction (as viewed when facing the plane of FIG. 2). The other side of selector spring 118 is attached to pusher 62; spring 118 pushes pusher 62 down to engage with teeth 68 on tooth rack 66 of slider assembly 20, the latter element best seen in FIGS. 3A-3C. This engagement is necessary for pushing slider assembly 20 and moving it towards the distal end 22 of cartridge assembly 18 during the stapling and cutting operations. Each squeeze of lever member 16 advances pusher 62 a predetermined distance while engaging tooth 68 on tooth rack 66 causing slider assembly 20 to advance incrementally one "step" within cartridge chassis member 42. When releasing lever member 16, pusher 62 retracts and moves to the next successive tooth.

When selector element 24 is moved in the distal direction to its release position, selector mechanism 54 turns in a clockwise direction (as viewed when facing the plane of FIG. 2). Pusher 62 moves upward due to the force exerted by selector spring 118 and it disengages from tooth rack 66 of slider assembly 20 (FIG. 3) as described in more detail in conjunction with FIGS. 18-20 below.

FIGS. 1 and 2 (and FIG. 11 below) show stapler 10 in its neutral position. When in neutral position, proximal end 126 of pusher 62 is restrained by restraining surface 124 of proximal end 122 of mode transfer element 120. When in open position, front 88 and back 90 links of locking linking mechanism 56 are in a "bent" non-extended configuration forming a "knee" 142 as shown. When lever element 16 is squeezed, locking leg 86 descends and presses on knee 142. After pressing on knee 142, front 88 and back 90 links extend and form a substantially linear configuration as shown in, for example, FIGS. 12-17 to be discussed below. This substantially linear configuration locks anvil member 14 in its "closed" position proximate to cartridge assembly 18. When knee 142 is pressed, locking linking mechanism pin 92 moves down and is restrained against the edge of chassis member 12.

It should be noted that prior to and throughout its operation, pusher 62 is positioned obliquely with respect to slider assembly 20. As is readily evident, the obliqueness changes during the various stages in the stapler's 10 operation. The angle also depends on the point pusher 62 has reached in cartridge assembly 18.

In order to prevent cartridge assembly 18 from moving forward when a force is applied to advance tooth rack 66 of slider assembly 20, thereby to staple and cut tissue, a cartridge step 106 and a locking step 108 are included on cartridge assembly 18 and anvil member 14 respectively. The engagement of these steps, shown for example in FIGS. 12-17 below, prevents relative motion between anvil member 14 and cartridge assembly 18.

In addition, stapler 10 includes safety tab 130 which is part of back link 90. Its purpose is to prevent pusher 62 from engaging one of teeth 68 of tooth rack 66 when anvil member 14 is not yet in its closed position, i.e. not proximate to cartridge assembly 18, and when selector element 24 is in its stapling and cutting mode position.

Stapler 10 is constructed so as to allow stapling and cutting of, for example, a large diameter bowel section. Even if the bowel is larger than the distance between tissue stop 100 and the distal end 22 of cartridge assembly 18, stapling and excision of the bowel may be effected. This may be achieved by stapling and cutting a first portion of the bowel. After completing the stapling and cutting of the first bowel portion, the procedure is interrupted and, if required, a fresh cartridge inserted into stapler 10. The stapling and cutting procedure is then resumed where it was interrupted until the entire bowel is severed. If necessary before resuming the stapling and cutting operation, the user may reposition the stapler with respect to the bowel section being resected. The user may then continue stapling and cutting along the same or in a different direction.

Reference is again made to FIGS. 3A-3C and 4 where a perspective view, two exploded perspective views and a side view of cartridge assembly 18, respectively, are shown. Cartridge assembly 18 has a proximal 40 and a distal end 22 and includes a cartridge 21 and a slider assembly 20. Slider assembly 20 includes a slider assembly cover 23. Cartridge assembly 18 contains a plurality of rows 34, typically, but without being limiting, four or six rows, of staples 50 in cartridge 21. These staples 50 are ejected in response to an ejection force conveyed by two rows of staple lifters 36 which are aligned with the rows 34 of staples 50. Cartridge 21 and slider assembly 20 typically are both constructed of plastic and are positioned on cartridge chassis member 42, typically constructed of metal. They may however be made of other materials as well.

Figure 3A:
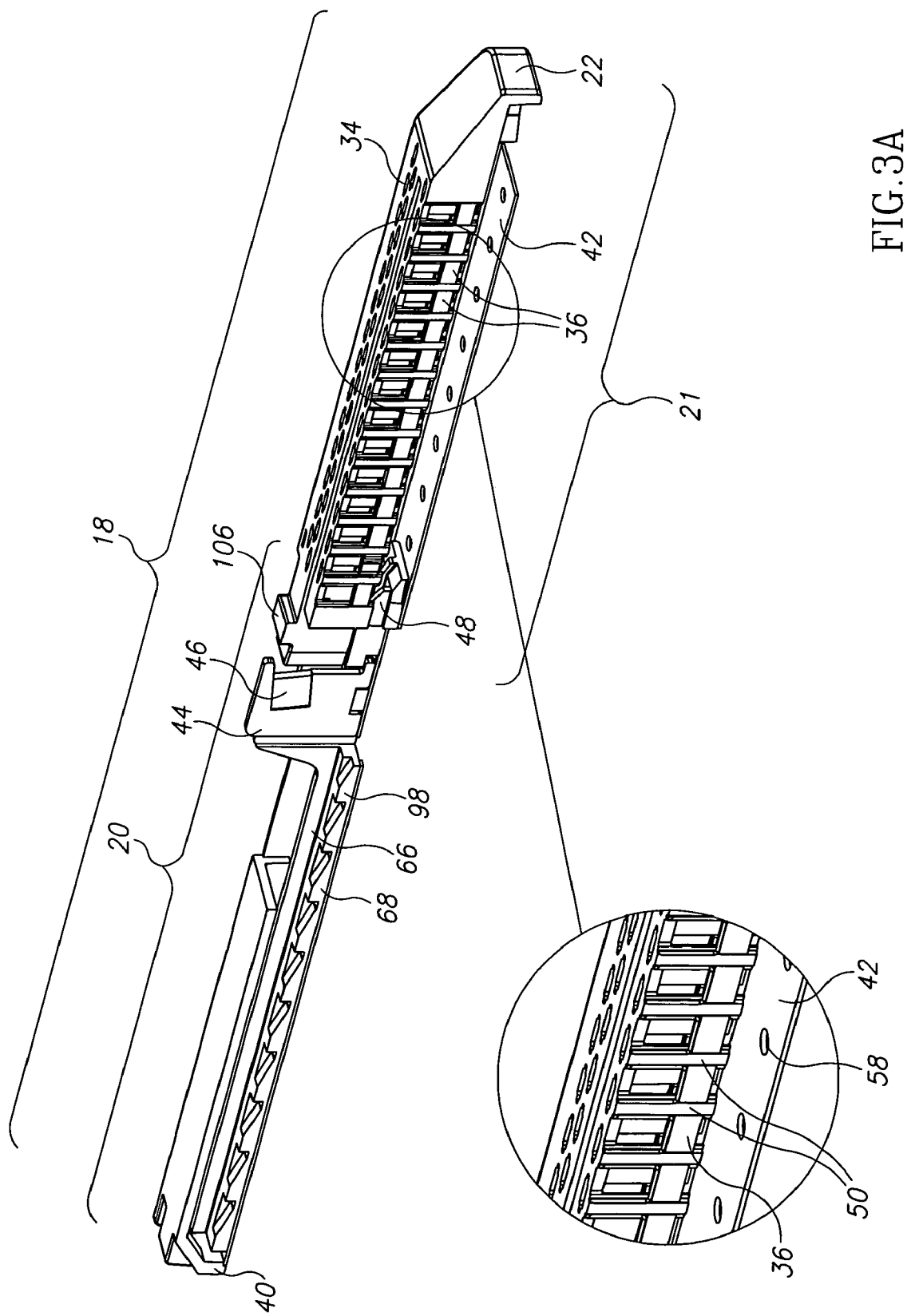
FIG. 3A is a partial perspective cross-sectional view of the cartridge assembly of the stapler shown in FIG. 1.

Slider assembly 20 includes a series of teeth 68, the first of which is distal tooth 98, on tooth rack 66. Slider assembly 20 is initially disposed on the proximal side of cartridge assembly 18 as seen in FIG. 3A. Slider assembly 20 is further comprised of a blade holder 44, a blade element 46 positioned on blade holder 44, and stapler ejector wedges 48, the latter disposed on each side of blade element 46 and aligned with a row of staples 34 contained in cartridge 21.

Figure 3B:
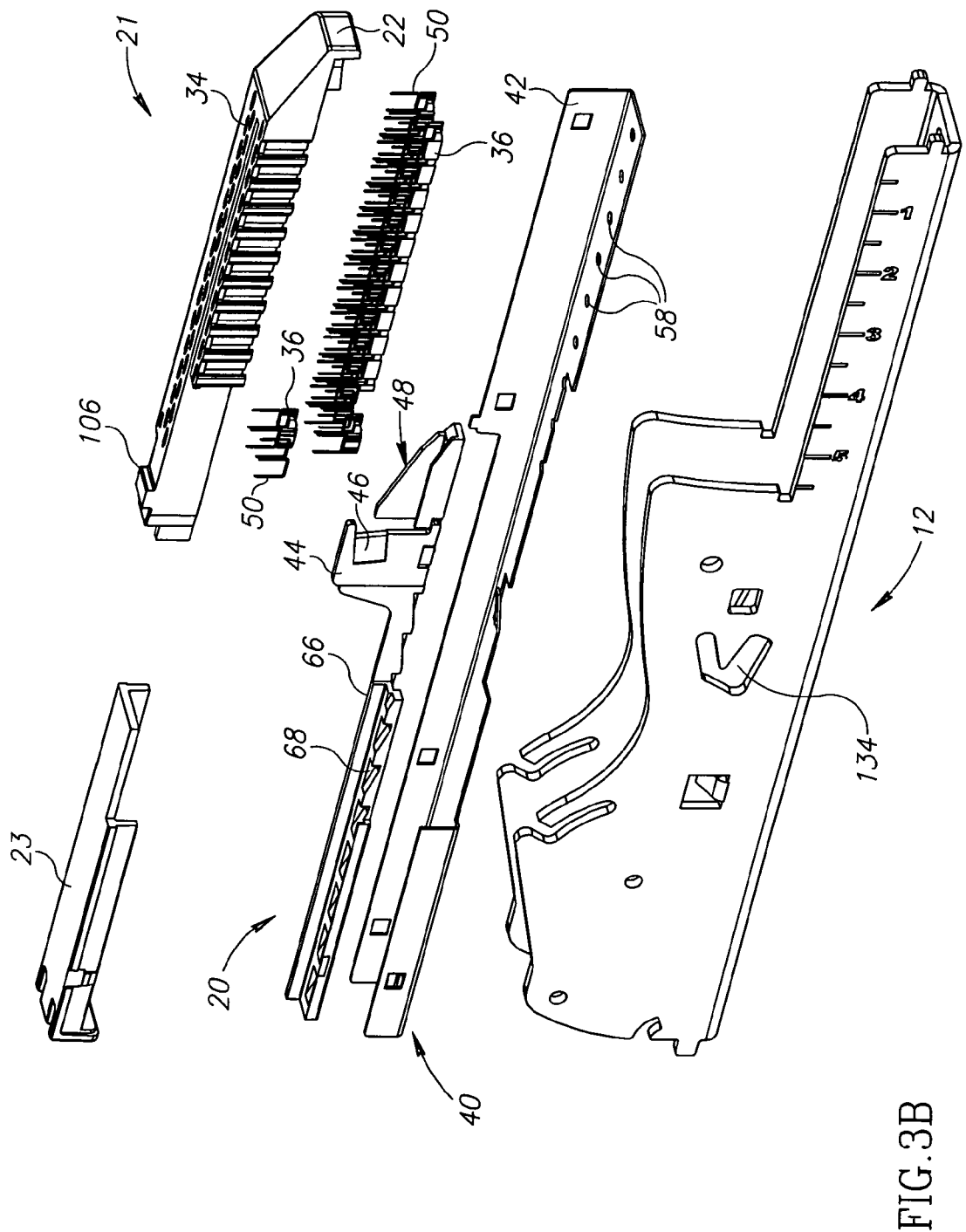
FIG. 3B is a first exploded view of the cartridge assembly shown in FIG. 3A.

FIG. 3B shows chassis member 12 in its entirety. Cartridge assembly 18 and slider 20 sit in and are supported by chassis member 12. Additionally, the entire locking linking mechanism 56 and the pusher 62 shown in FIG. 2 are positioned within the larger, non-elongated, shaped proximal end of chassis member 12. Groove 134 necessary for the release mechanism discussed in conjunction with FIG. 21 below is also shown.

Figure 3C:
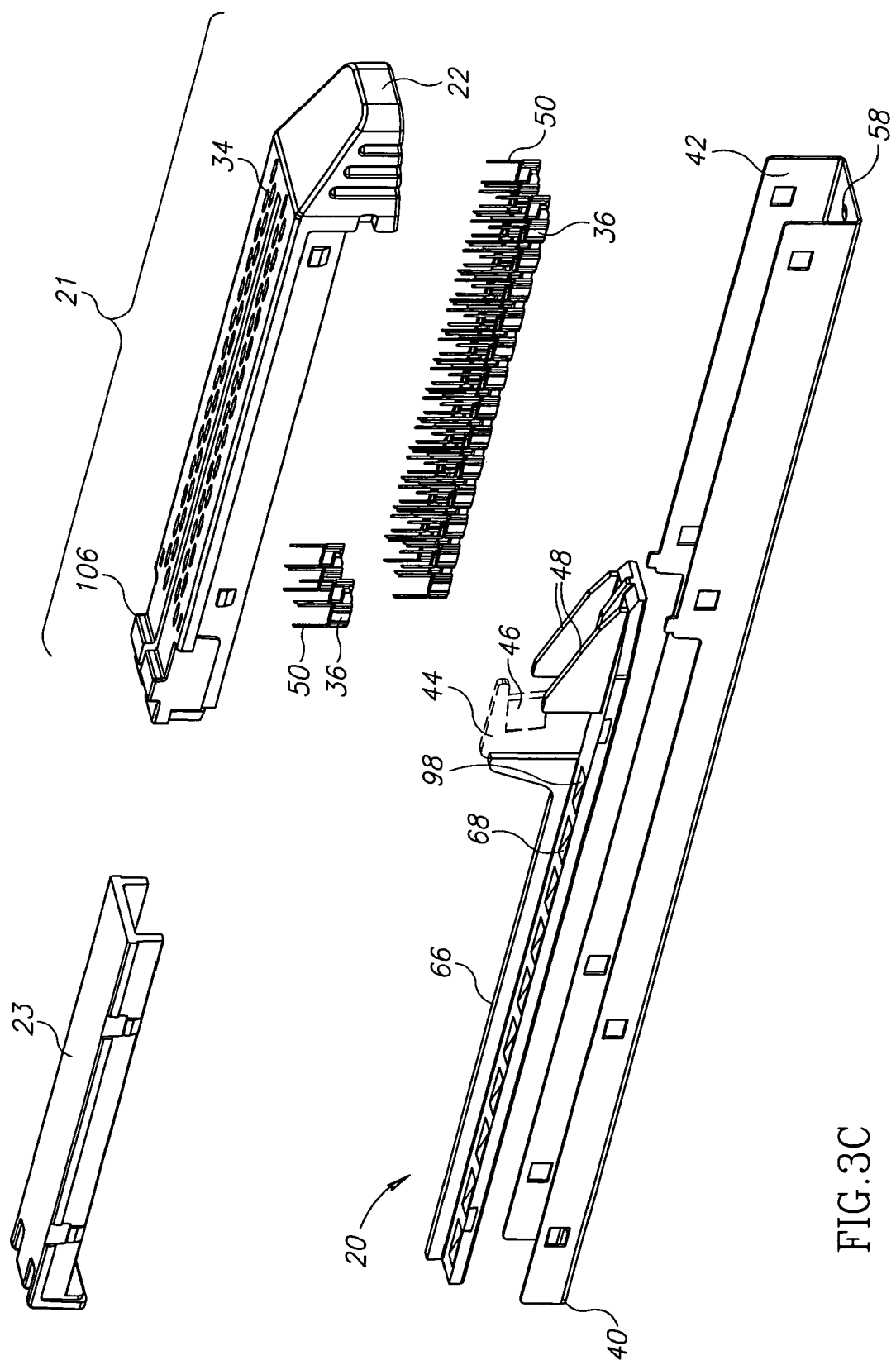
FIG. 3C is a second exploded view of the cartridge assembly shown in FIG. 3A, but wherein the blade holder and blade element are seen in broken lines, indicating that the stapler may optionally be bladeless.

FIG. 3C is a second exploded view of the cartridge assembly shown in FIG. 3A. The blade holder and blade element are seen in broken lines, indicating that the stapler may optionally be bladeless.

Reference is now made again to FIG. 4 where a perspective underside view of cartridge assembly 18 of FIG. 3A is shown. In the Figure a series of position indicator windows 58 on the underside 60 of cartridge chassis member 42 is shown. The position of slider assembly 20, which includes blade element 46 and stapler ejector wedges 48, in relation to cartridge 21 of cartridge assembly 18, is observable through these windows during the stapling and cutting operation.

Figure 4:
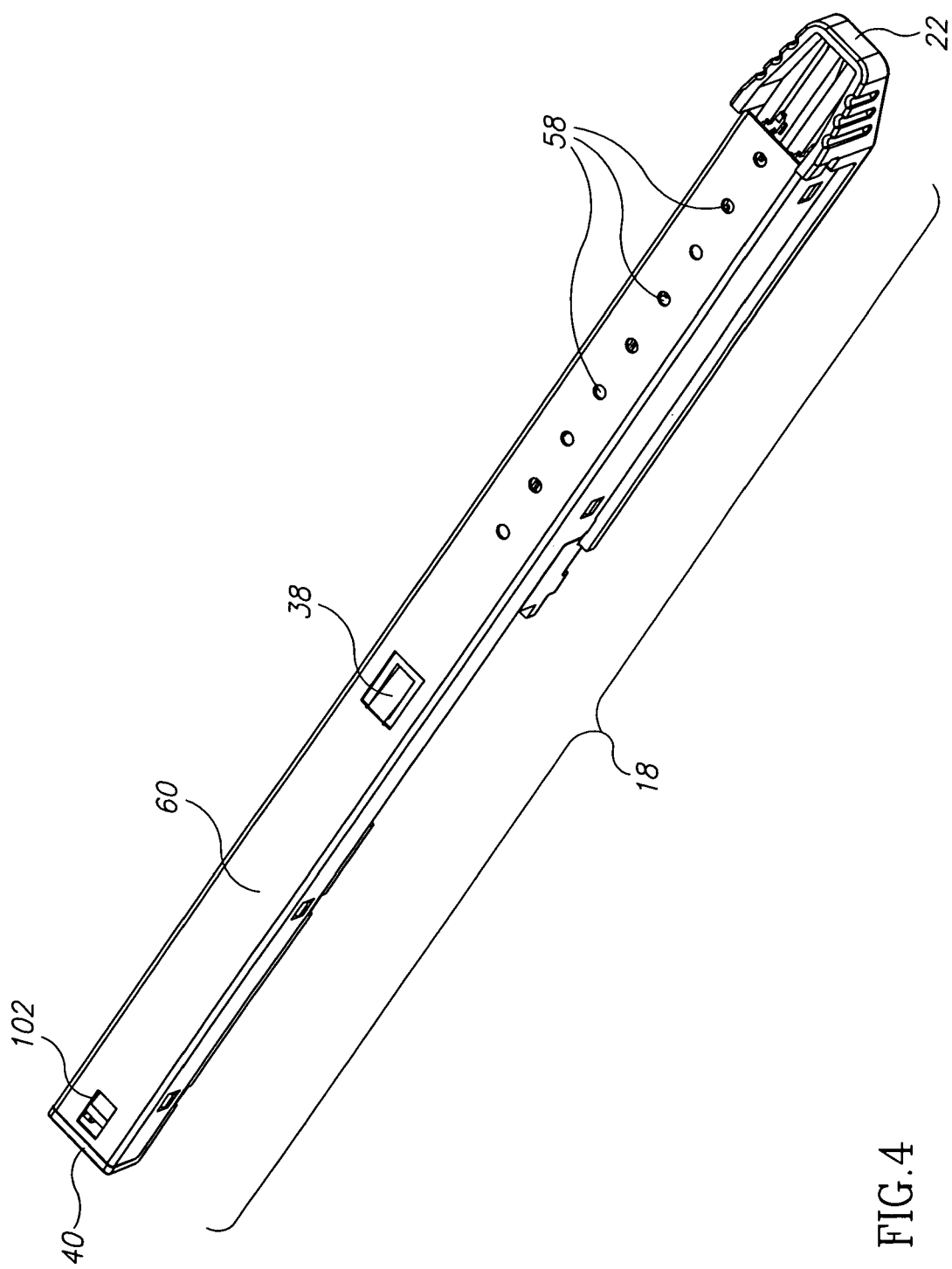
FIG. 4 is a perspective underside view of the cartridge assembly shown in FIG. 3A.

Cartridge locking groove 102 is also shown in FIG. 4. Groove 102 prevents undesired movement of cartridge chassis member 42 when a force is applied in the distal direction by a user on cartridge assembly 18. Groove 102 is locked by cartridge locking snap 104 as described below in conjunction with FIG. 7. Also noted on the underside 60 of cartridge chassis member 42 is ratchet tooth 38 which engages with ratchet grooves 39 (FIG. 5) on the bottom of slider assembly 20 during the pushing effected by pusher 62. Ratchet tooth 38 prevents slider assembly 20 from moving in a proximal direction.

Figure 5:
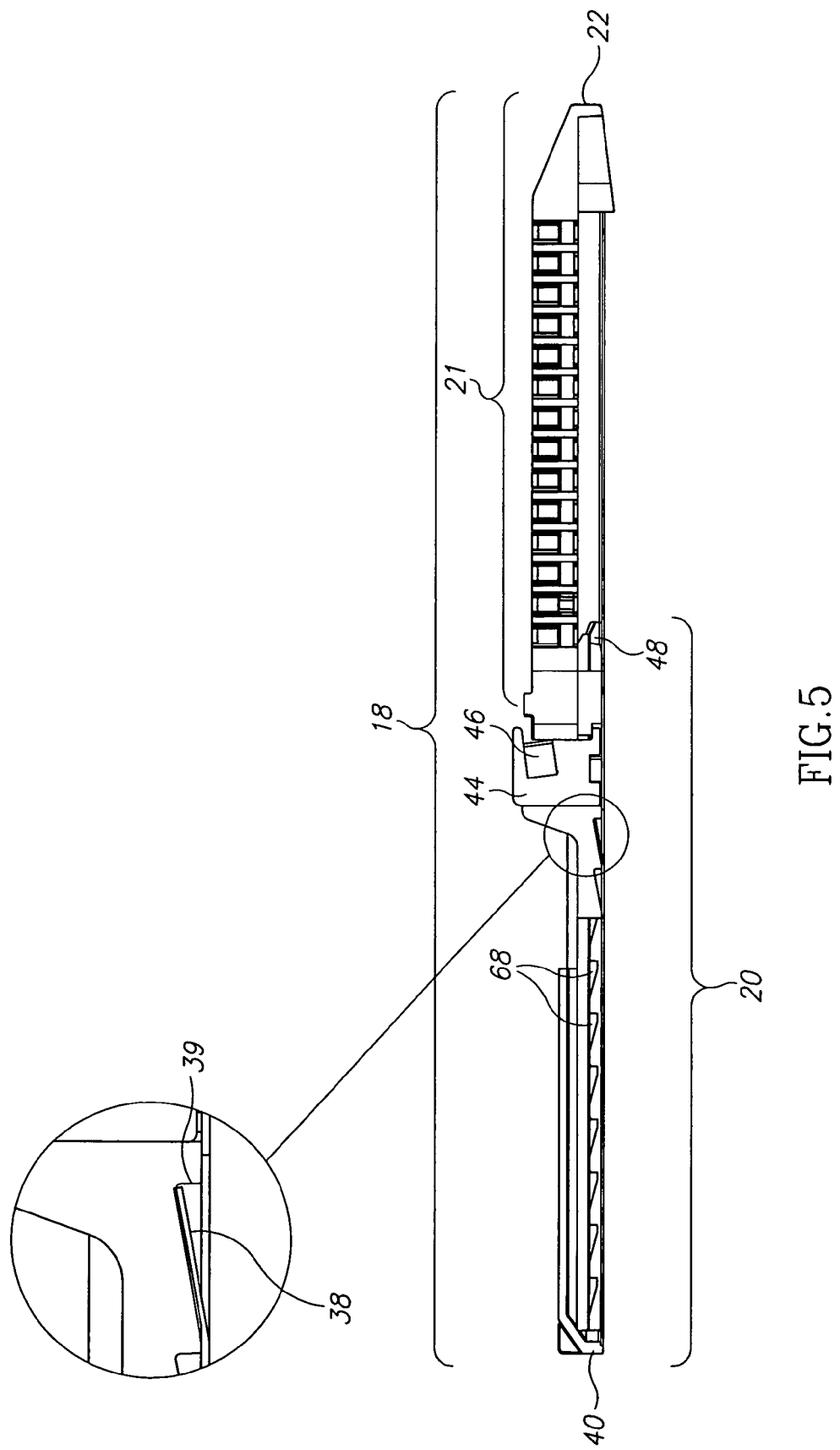
FIG. 5 is a side view of the cartridge assembly shown in FIG. 3A and a detailed view of the cartridge ratchet mechanism.

In FIG. 5, to which reference is now made, blade holder 44 and blade 46 are clearly shown as are individual teeth 68. There is also presented an enlarged view of ratchet tooth 38 and ratchet groove 39. As has been discussed in conjunction with FIG. 2 above and will be discussed in more detail below, pusher 62, shown in FIG. 2 and elsewhere, engages teeth 68 of tooth rack 66 thereby pushing slider assembly 20 in the distal direction of cartridge assembly 18. As lever member 16 is squeezed while stapler 10 is in its stapling and cutting mode, pusher 62 pushes slider assembly 20 forward toward the distal end 22 of cartridge assembly 18. Slider assembly 20 advances incrementally step-wise as pusher 62 advances one tooth per squeeze of lever member 16. As slider assembly 20 advances, blade 46, blade holder 44 and stapler ejection wedges 48 advance in a stepped fashion. With each stepped advance of slider assembly 20, an additional set of staples 50, typically but without being limiting, four or six staples, are ejected by stapler ejector wedges 48. Staples 50 pass through tissue clamped between anvil member 14 and cartridge assembly 18 (FIG. 2) and then advancing blade element 46 cuts further into the clamped tissue. This stapling and cutting process is described in more detail below.

In accordance with the operating characteristics of stapler 10, accidental re-use of a cartridge 21 which no longer contains any staples, is prevented. Operation of lever member 16 is not possible until slider assembly 20 has been repositioned at the initial, proximal end 40 of cartridge chassis member 42. When a cartridge 21 is exhausted, blade 46 remains near the distal end 22 of cartridge 21. In a spent cartridge 21, blade 46 is unable to move backwards and cartridge 21 can not be reused.

In accordance with one embodiment of the present invention, an exhausted cartridge assembly 18 of stapler 10 is detached and replaced with a fully loaded staple cartridge 21. In another embodiment, the cartridge 21 is replaced with a new supply of staples and the blade 46 is also replaced. In accordance with a further embodiment of the present invention, cartridge assembly 18, including blade element 46, are not replaceable.

Figure 6A:
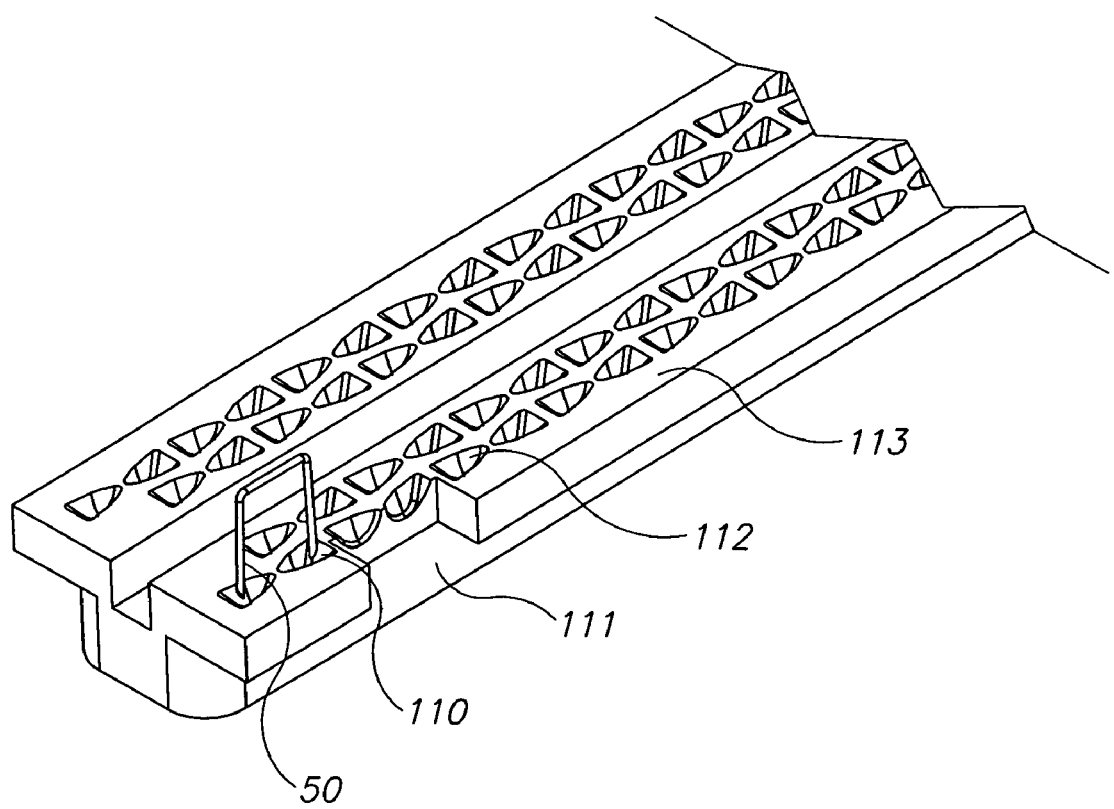
FIG. 6A is a detailed view of the anvil grooves used with the anvil of the stapler shown in FIGS. 1-2.

FIG. 6A, to which reference is now made, shows the anvil face 113 proximate to cartridge assembly 18 (FIGS. 3A-3C). Anvil face 113, when positioned adjacent to cartridge assembly 18 and with the bowel portion to be excised positioned therebetween, acts as the crimping, i.e. closing, surface for the ejected staples. Anvil face 113 includes stapling recesses 110 constructed to have a funnel shape 112 at one end. Part of anvil face 113 is cut away 111 so that side views of stapling recesses 110 are visible.

Prior art anvils include recesses that are typically square, rectangular or even hour-glass in shape. The present invention has funnel-shaped recesses 110 which are better able to keep staples 50 in one plane during the crimping/closing process even when the staples are distorted from their original planar shape as a result of their penetrating the tissue being stapled. After the ejected staple encounters anvil face 113 and is crimped, i.e. closed, the crimped staple 50 forms a "B" shape. Each stapling recess 110 is large where the staple meets the anvil to allow for greater tolerances. The recess is gathered to a rounded corner at one end to ensure that the two ends of the staple will remain in the same plane and to ensure a better B-like shape. The wide end of the stapling recess 110 meets the staple leg and guides it into the narrow rounded part of the funnel-shaped recess shaping it into a flat, i.e. planar, crimped B-like shape.

While in FIG. 6A the adjacent rows of funnel shaped recesses appear staggered with respect to each other, in other embodiments the rows do not have to be offset from each other.

Figure 6B:
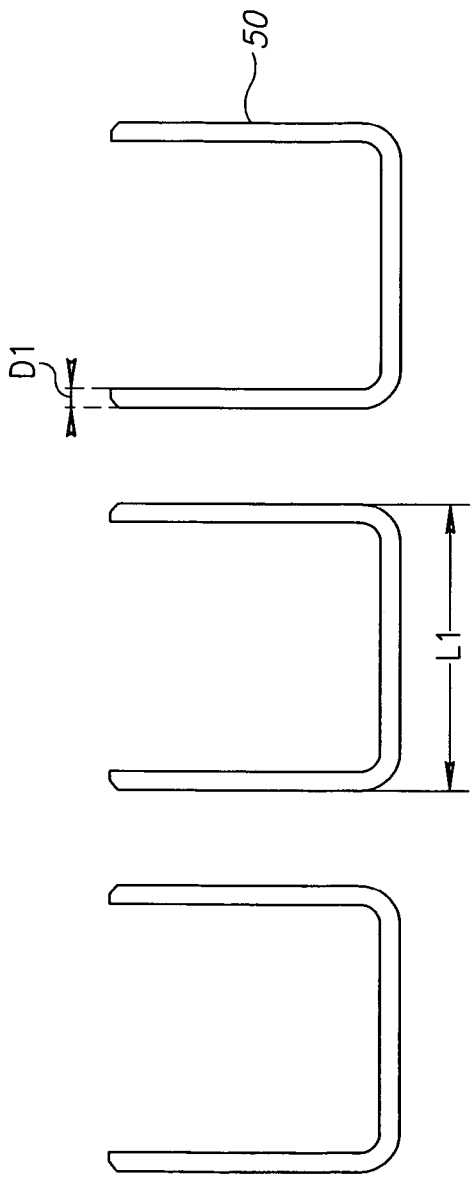
FIGS. 6B-6D are views showing additional details of the staples, anvil recesses and recess configurations and their relative dimensions with FIGS. 6C and 6D showing top and side views of the recesses respectively.
Figure 6C:
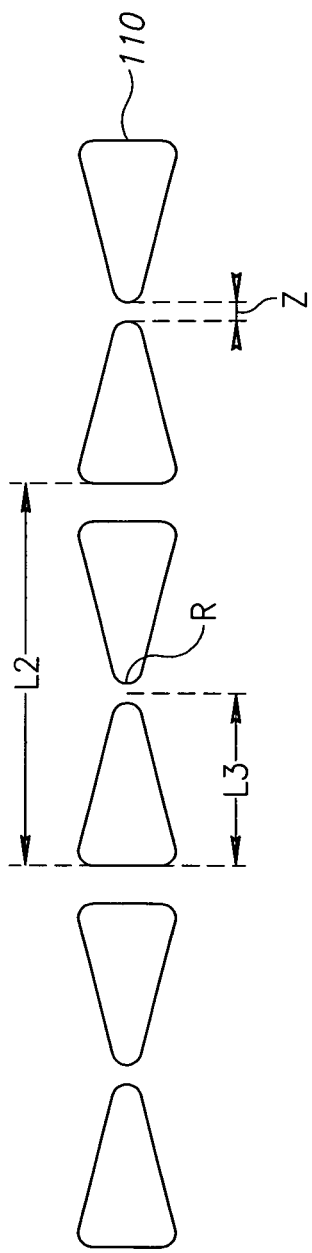
Figure 6D:
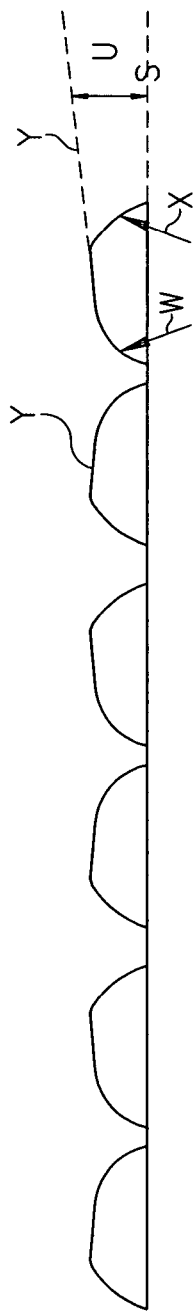

Reference is now made to FIGS. 6B-6D which give typical relative dimensions of the staples, anvil recesses and recess configurations. In FIG. 6B, three staples are shown. The wire diameter of each staple is D1, the width of the staple is L1 and the staples are spaced as shown at a distance of L2. The distance between adjacent wide ends of the recesses as shown in FIG. 6C, may range in length from between about D1 to about 4D1.

As shown in FIGS. 6B-6C, the recesses repeat at a uniform distance of L2. The wide end of the recess may range in size between about 3 to about 6 times D1. The funnel is gathered to a rounded end where the end has a radius of curvature ranging from about the same radius R (=D1:2) as the wire to about twice the radius of the wire of the staple, that is D1. The distance Z between the adjacent rounded ends of two recesses ranges between about the size of the wire diameter (D1), up to about three times the wire diameter (3D1). The length of the recess is larger than about half the staple width (L3>L1:2) to compensate for any misalignment of the staple position in the anvil recesses.

FIG. 6D shows a cross sectional view of the recesses 110 on anvil member 14. It shows the penetration radius of curvature X of the anvil groove, i.e. the first surface the staple meets as it enters the recesses and starts to bend. It should be noted that the staple enters the recess from below in the presentation of FIG. 6D. Only one end of the staple enters a recess. After bending begins, the staple is guided in a plane Y that can be inclined or perpendicular to the direction of staple movement, that is inclined or parallel to the surface S of the anvil in FIG. 6D. The angle U of plane Y with respect to the anvil surface S is typically from about 0 to about 5 degrees. After bending, the staple encounters an exit radius of curvature W that guides the staple out of the recess, generating the closed planar B-like shape.

The sizes and the size relationships shown in FIGS. 6B-6D are meant to be illustrative only and are not intended to be limiting.

In the above description, a circular wire having a diameter D is described. It should readily be understood that wires with other cross sections such as, but without intending to be limiting, elliptical, square or rectangular cross sections, may be used. In such cases, diameter should be replaced by the largest cross section dimension of the wire.

Figure 7:
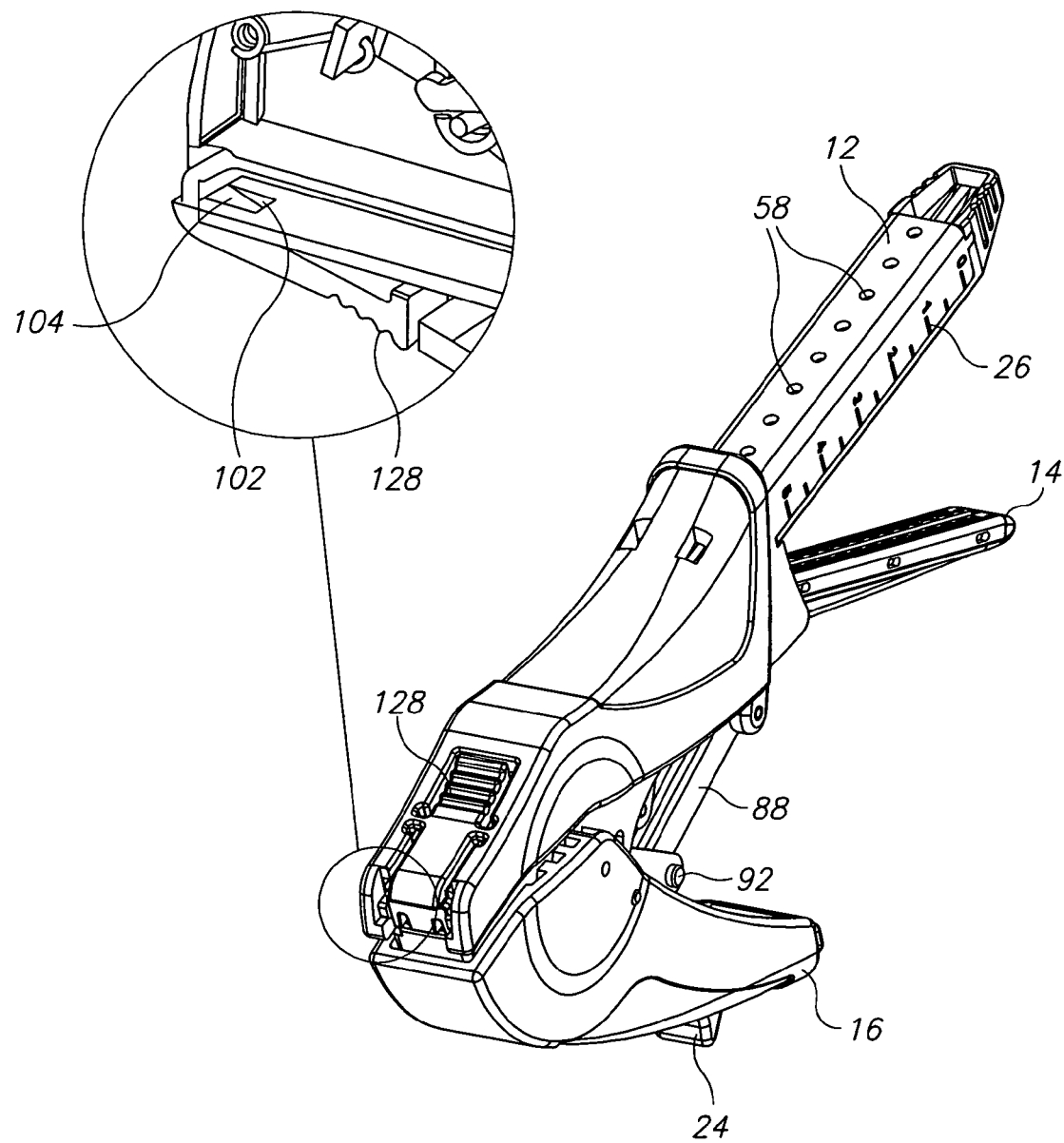
FIG. 7 is a perspective bottom view of the stapler shown in FIG. 1.

FIG. 7 to which reference is now made shows a perspective generally underside view of stapler 10. Additionally, there is a detailed cut away view of proximal end 30 of chassis member 12. The cut away view has been inverted from the general underside view. When cartridge locking groove 102 and cartridge locking snap 104 engage, they hold cartridge assembly 18 firmly in place when the user applies a pulling force in the distal direction. When cartridge release snap 128 is pressed, cartridge chassis member 42 is released. Cartridge assembly 18 (FIG. 3A) can then be removed from stapler 10 and a new cartridge assembly 18 can be inserted.

Figure 10:
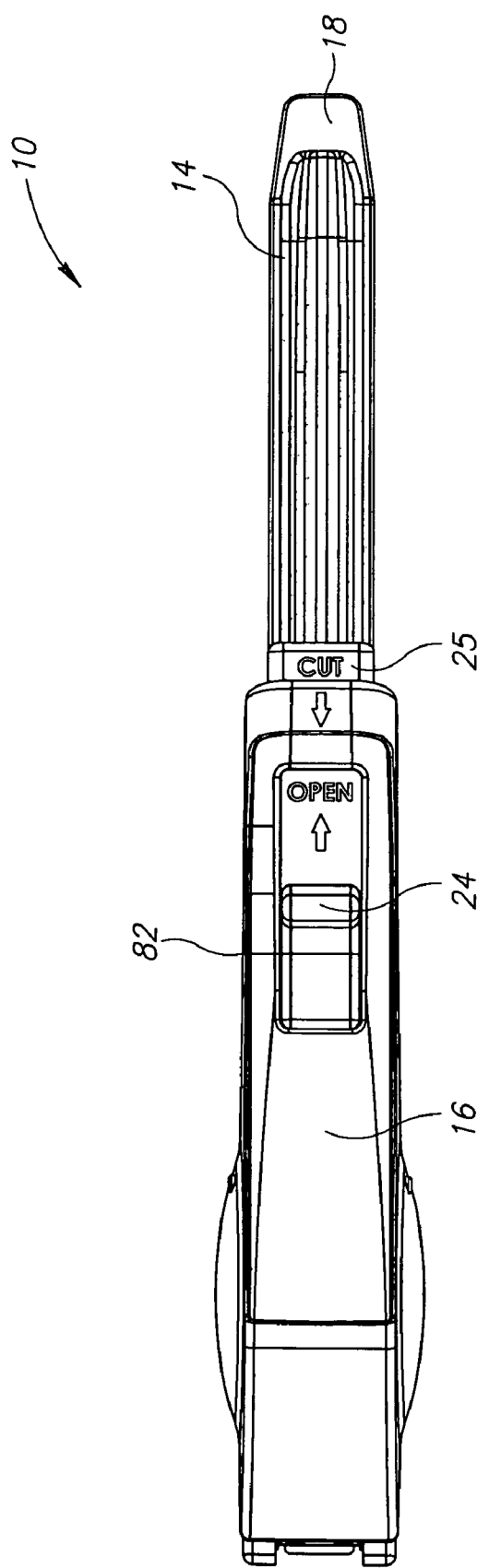

Reference is now made to FIGS. 8, 9, and 10 where top plan views of stapler 10 illustrate the three operational mode positions of selector element 24. The Figures include cut button 25, anvil member 14, lever member 16 and cartridge assembly 18. In FIG. 8, selector element 24 is shown in its neutral and closing mode position 80. In FIG. 9, selector element 24 is shown in its releasing mode position 84, while in FIG. 10, it appears in its stapling and cutting mode position 82. The releasing mode position 84 and the stapling and cutting mode position 82 are sometimes also referred to herein as the selector element's 24 distal and proximal positions, respectively.

The neutral and closing mode position is used when the stapler is inactive and when clamping tissue between anvil member 14 and chassis member 12. Clamping is effected when lever member 16 is squeezed causing anvil member 14 to pivot toward chassis member 12. The proximal stapling and cutting mode position 82 of FIG. 10 is the mode position used when stapling and cutting tissue. Releasing mode position 84 of FIG. 9 is used to release anvil member 14 and allow it to pivot away from chassis member 12 after stapling and cutting has been completed. It is also used if the first clamping attempt has been unsuccessful and the tissue to be excised has not been properly positioned. In such cases, the device must be opened by moving selector element 24 to the releasing mode position. Another attempt at positioning and clamping the tissue for excision is effected by first returning selector element 24 to its neutral and closing mode position 80. Changing the position of selector element 24 may be carried out regardless of the disposition of lever member 16. However, each new mode position becomes operatively effective only after lever member 16 is returned to its fully open configuration.

Referring again to FIG. 2, selector element 24 of stapler 10 is shown therein in its neutral and closing position described in conjunction with FIG. 8 above. By squeezing lever member 16, anvil member 14 is brought into close operational association with cartridge assembly 18 by locking linking mechanism 56. As anvil member 14 pivots, indicated by arrow 52B, relative to cartridge assembly 18, a bowel portion (not shown) is disposed between anvil member 14 and cartridge assembly 18 and held tightly therebetween. Anvil member 14 remains in close locked operational association with cartridge assembly 18, locking being effected by locking linking mechanism 56.

Reference is now made again to FIGS. 3A-3C and 5, as well as to FIG. 2. In the stapling and cutting operational mode, activated when selector element 24 is brought to its stapling and cutting mode position 82 as in FIG. 10, lever member 16 transforms an applied squeezing force into a predetermined driving force to slidably move slider assembly 20 in the distal direction along cartridge chassis member 42.

As lever member 16 is squeezed, pusher 62 pushes slider assembly 20 along cartridge chassis member 42. As pusher 62 advances in the distal direction, distal end 64 of pusher 62 engages tooth rack 66, which is part of slider assembly 20. By repeatedly squeezing lever member 16, successive individual teeth 68 of tooth rack 66 are operatively engaged by distal end 64 of pusher 62, thereby providing the pushing force and incremental step-like movement to slider assembly 20 along cartridge chassis member 42. It should be noted that prior to and throughout its operation pusher 62 is positioned obliquely with respect to slider assembly 20.

As slider assembly 20 moves, staples 50 are ejected from cartridge assembly 18 in a step-wise sequence moving increasingly away from the user. Additionally, as will be described in conjunction with FIG. 22 below, the bowel is stapled along at least two rows and cut along a line between the staple rows.

When selector element 24 is brought to its releasing mode position 84 described in conjunction with FIG. 9, pressing lever member 16 releases anvil member 14 from locking engagement with cartridge assembly 18, and anvil member 14 pivots away from cartridge assembly 18. Anvil member 14 pivots after pusher 62 has lifted away from tooth rack 66 and pushed against locking linking mechanism 56. Locking linking mechanism 56 then reverts from its substantially linear configuration to the essentially "bent" configuration shown in FIG. 2.

FIGS. 11-20 are cross sectional views of stapler 10 which show in detail the positions of the major members and elements of the stapler during various stages of its operation.

Figure 11:
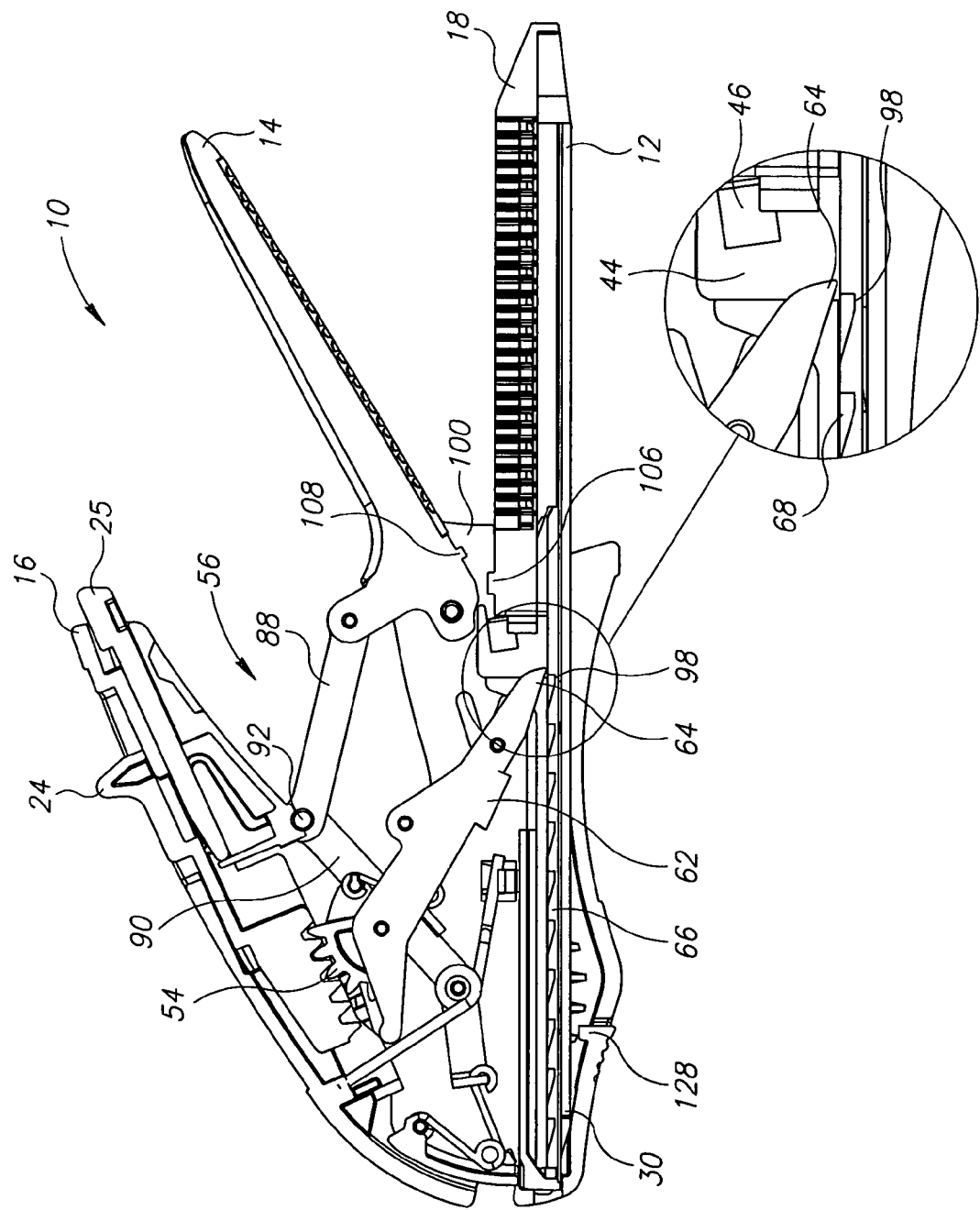
FIG. 11 is a cross-sectional view of the stapler with an anvil member in an open position.
Figure 12:
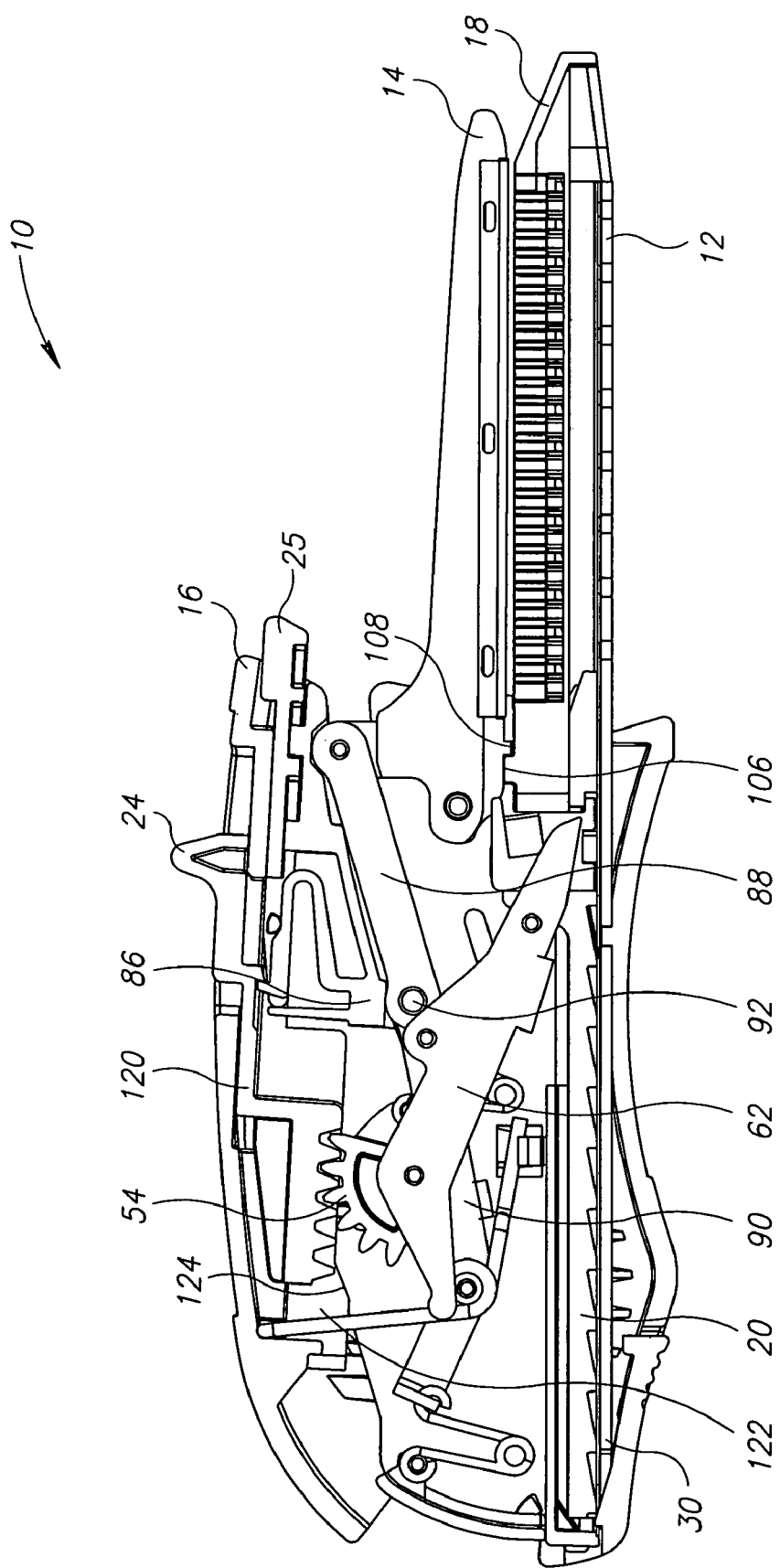
FIG. 12 is a partial cross-sectional view of the stapler in a closed position.
Figure 13:
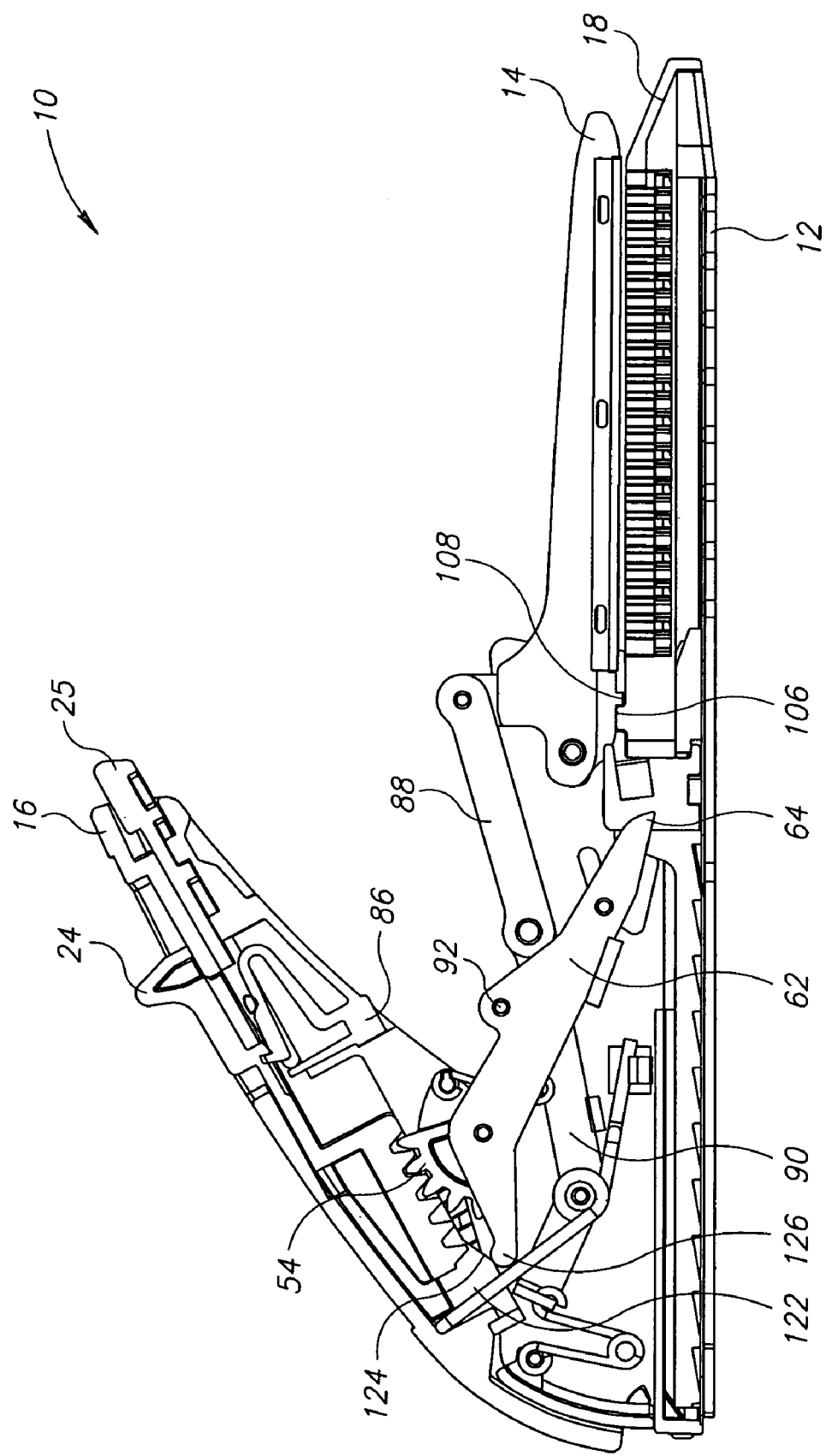
FIG. 13 is a partial cross-sectional view of the stapler in a position where the anvil is closed and the lever is open.

FIG. 11 shows stapler 10 in its neutral and closing mode similar to that shown in FIGS. 1 and 2 above. FIG. 12 shows stapler 10 in the same mode where tissue is clamped and held between anvil member 14 and cartridge assembly 18. In FIG. 12, lever member 16 is squeezed and held in its closed position. FIG. 13 shows stapler 10 in its neutral and closing mode with tissue being clamped and held between anvil member 14 and cartridge assembly 18 but with lever member 16 in its open position.

Figure 14:
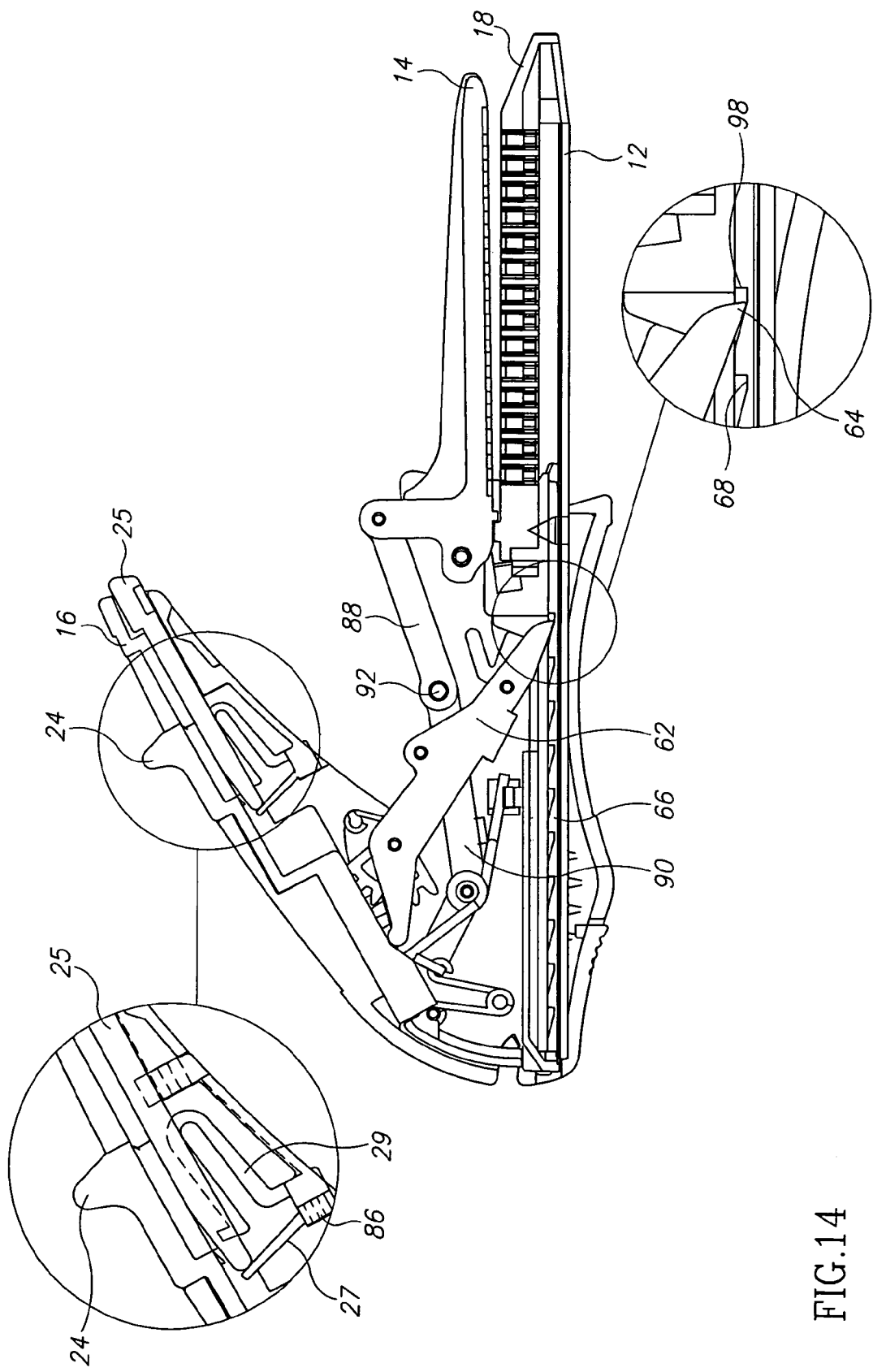
FIGS. 14, 15, 16 and 17 are partial cross-sectional views of the stapler in a stapling and cutting mode.
Figure 15:
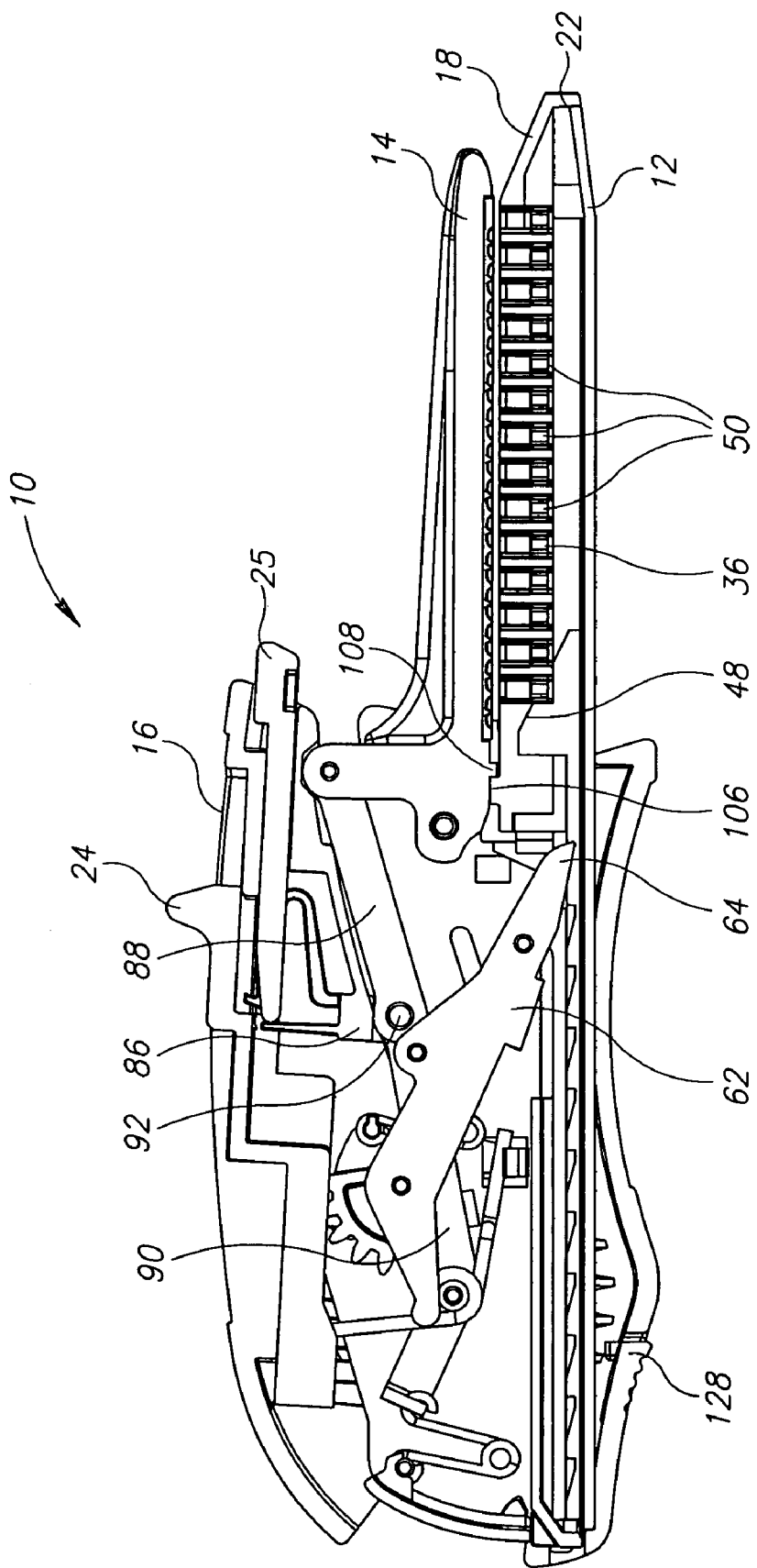
Figure 16:
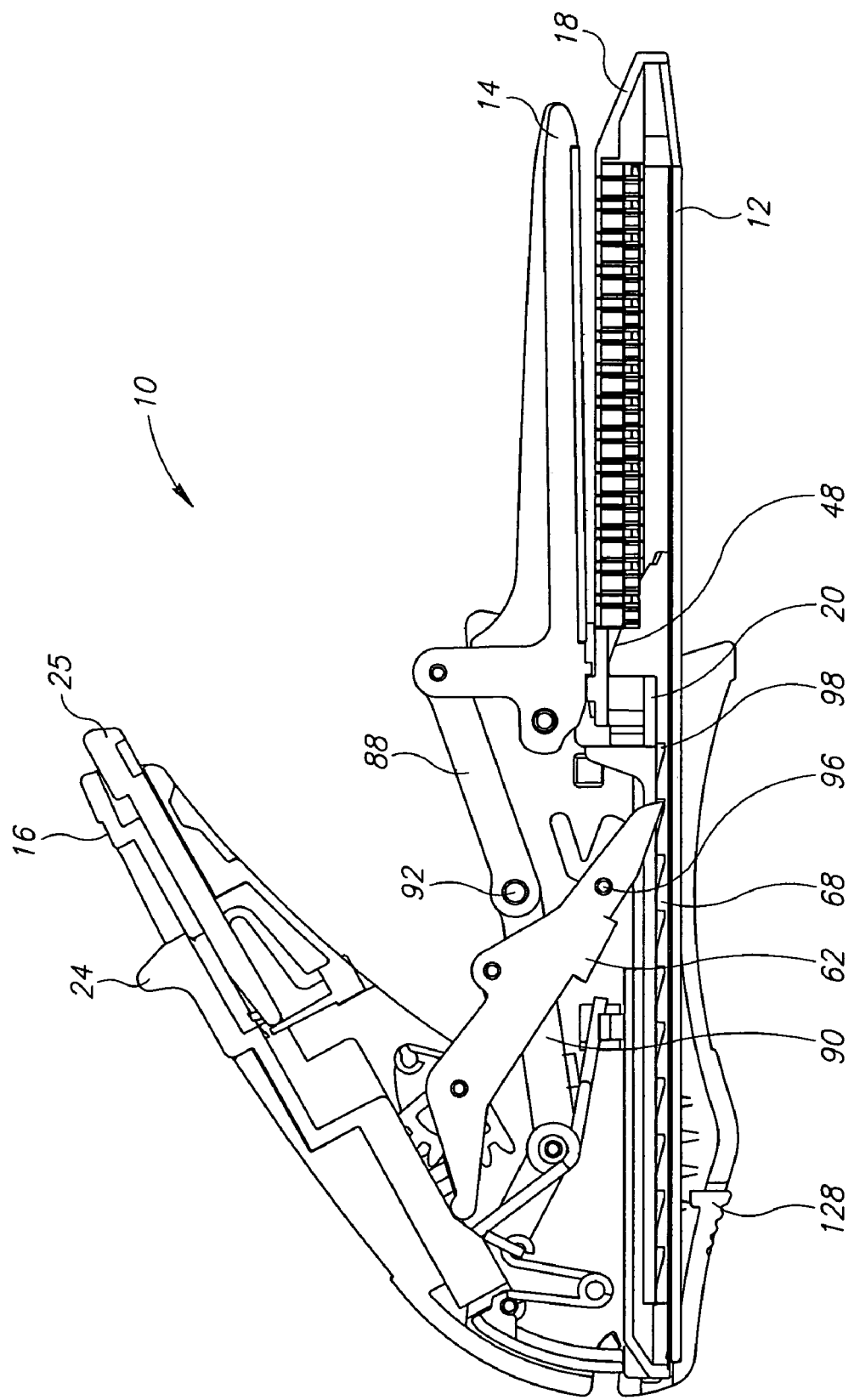
Figure 17:
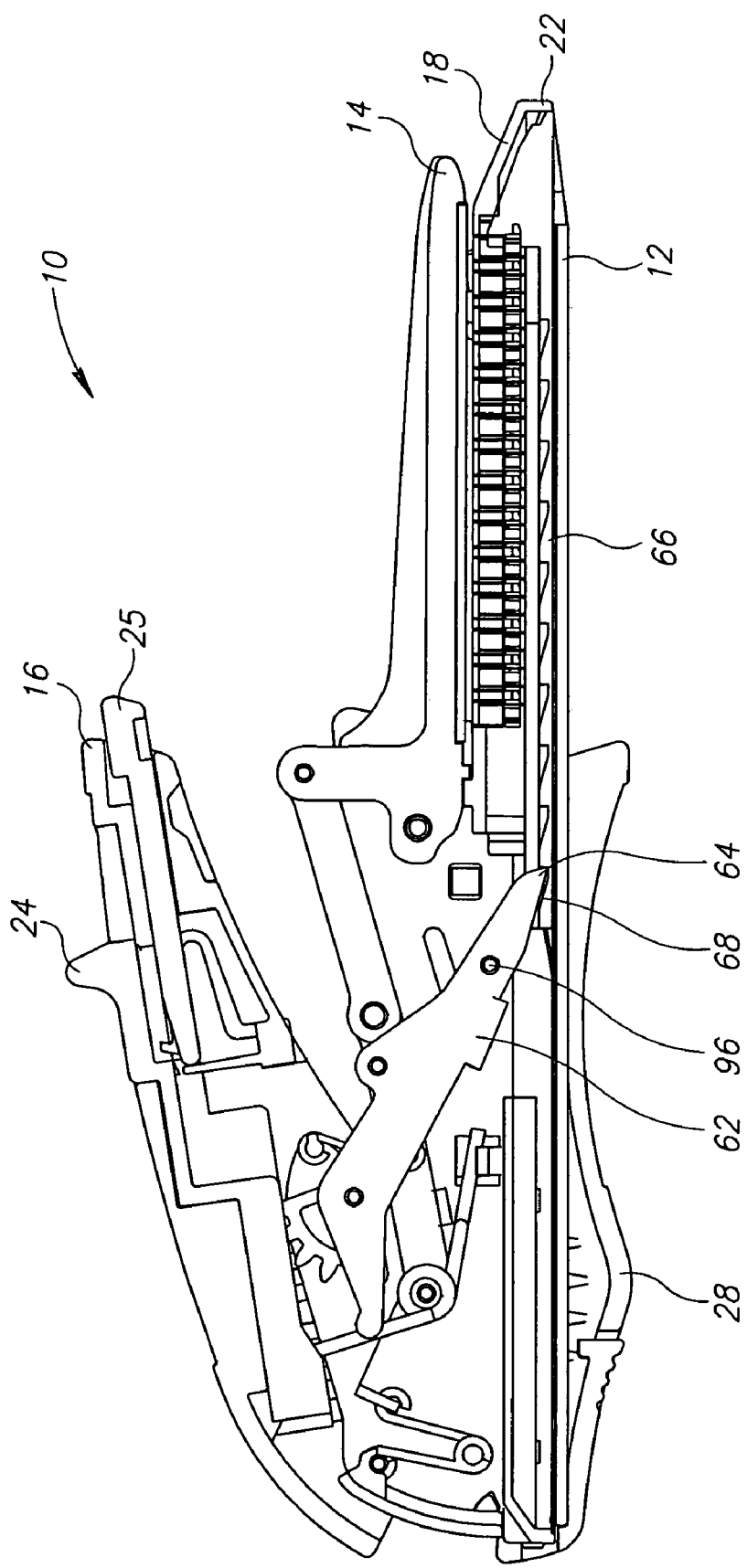

FIGS. 14, 15, 16 and 17 are partial cross-sectional views of stapler 10 while the device operates in its stapling and cutting mode. FIG. 14 shows stapler 10 in this mode with lever member 16 in its open position prior to the first squeeze of lever member 16. FIG. 15 shows the stapler in the same mode with lever member 16 closed after the initial squeeze in a series of repetitive squeezing operations. FIG. 16 shows the stapler with lever member 16 up after the first squeeze and prior to a series of further squeezes. FIG. 17 shows stapler 10 in its stapling and cutting mode after the final squeeze in a series of squeezes and with lever member 16 still being held in its closed position.

Figure 18:
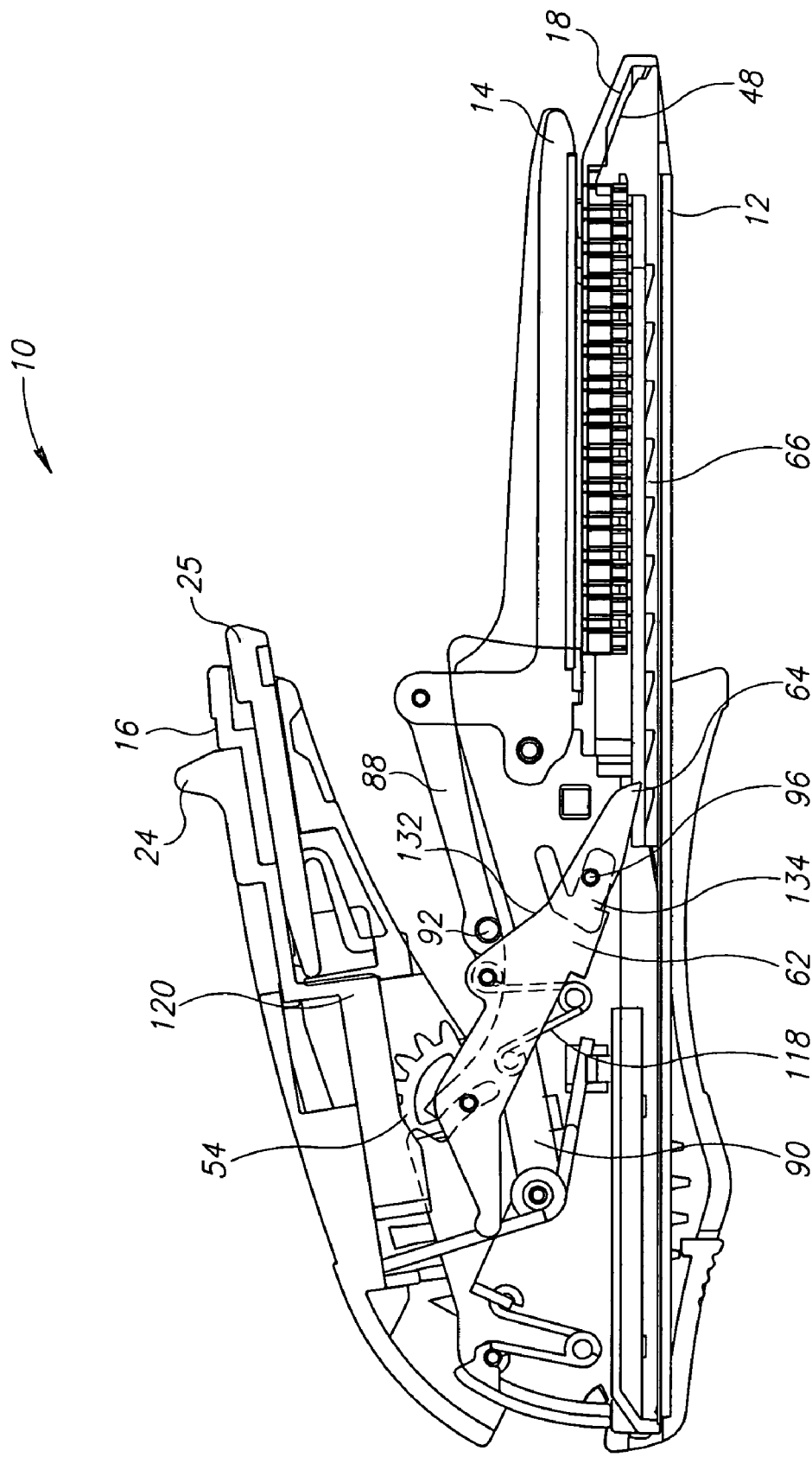
FIGS. 18 and 19 are partial cross-sectional views of the stapler with the selector mechanism in an open position prior to the release and opening of the anvil.
Figure 19:
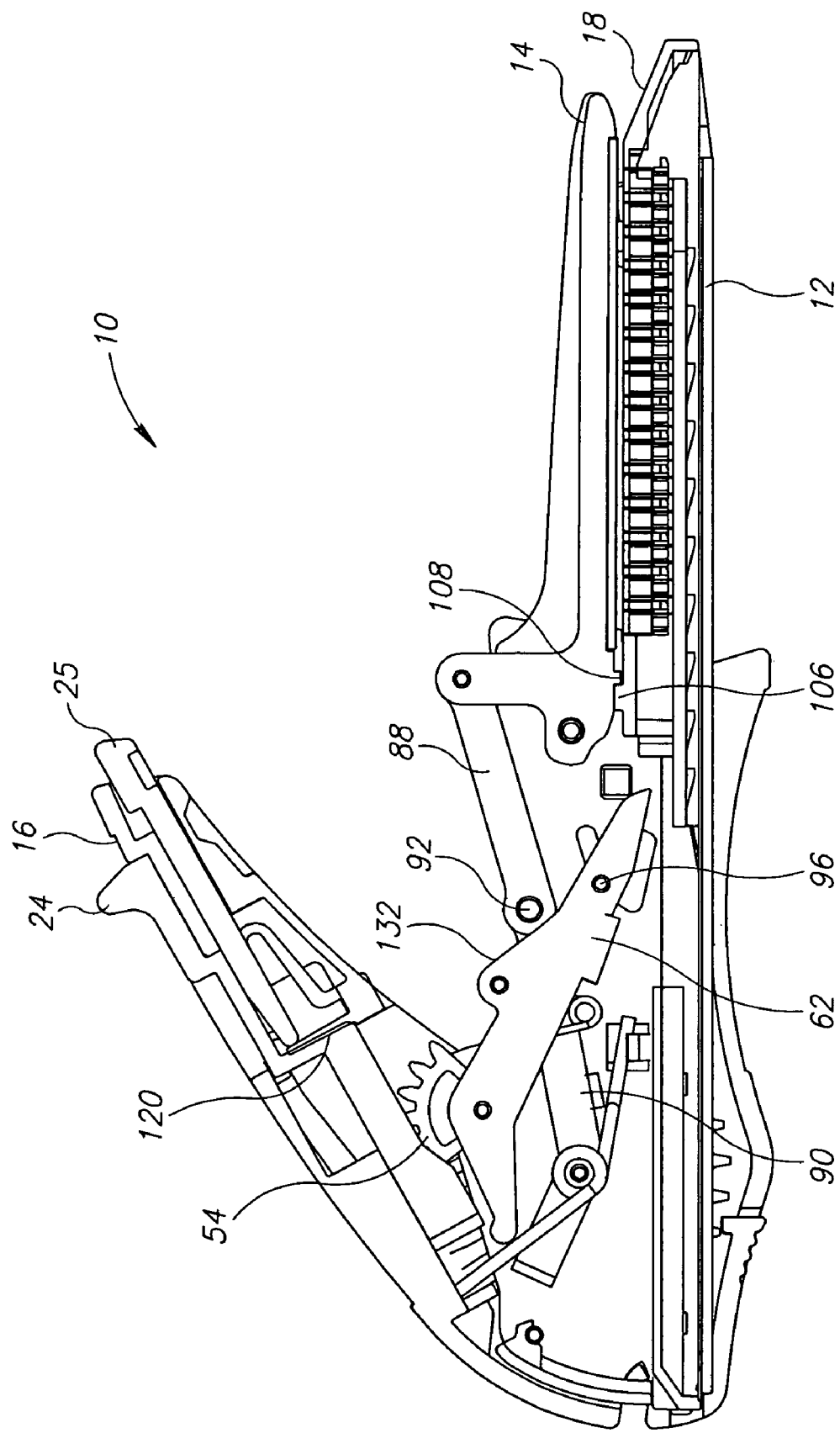
Figure 20:
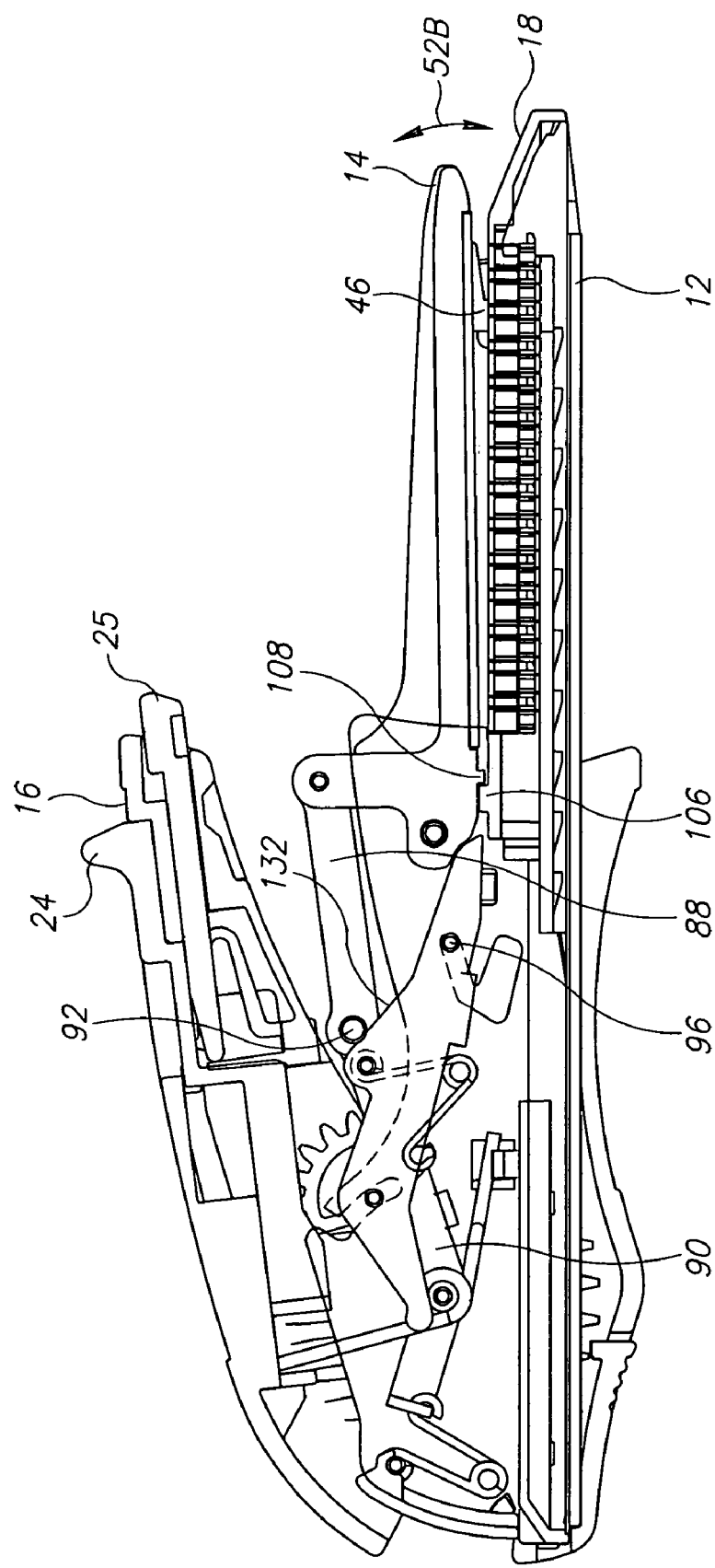
FIG. 20 is a partial cross-sectional view of the stapler with the anvil in a released open position after the stapling and cutting process.

FIG. 18 shows stapler 10 in its releasing mode after completing the stapling and cutting operation but before opening anvil member 14. FIG. 19 shows stapler 10 in releasing mode with anvil member 14 still closed but with lever member 16 released and in its up or open position. FIG. 20 is a partial cross-sectional view of stapler 10 with lever member 16 pressed and before complete release of locking linking mechanism 56. In FIG. 20, anvil member 14 is shown as beginning to open and pivot away from chassis member 12.

Each of FIGS. 11-20 will now be described in greater detail to more clearly illustrate the operation of stapler 10.

FIG. 11 to which reference is now made shows a cross sectional view of stapler 10 in its open position in neutral and closing mode as shown in FIGS. 1 and 2. In this mode, selector element 24 is disposed at neutral and closing mode position 80 as in FIG. 8 discussed above. Lever member 16, is disposed in a fully open configuration. Additionally, anvil member 14 is fully open and locking linking mechanism 56 is in its raised "bent" "disengaged" configuration. Slider assembly 20 is disposed at proximal end 30 of chassis member 12.

Included in FIG. 11 is an inset close-up view of distal end 64 of pusher 62 positioned above slider assembly 20. Also shown are teeth 68 and first distal tooth 98 and their relation to distal end 64 when stapler 10 is in its neutral and closing mode position. Pusher member 62 is in raised disengaged position relative to tooth rack 66. Distal end 64 does not enter first distal tooth 98 since pushing is not, and can not be, effected in the stapler's neutral and closing mode.

In FIG. 12, to which reference is now made, stapler 10 is shown in its neutral clamping position. In this position the user clamps a portion of tissue, typically, but without being limiting, the bowel, between anvil member 14 and cartridge assembly 18. This can be effected by squeezing (also herein sometimes described as "pumping" or "pressing") against spring mounted lever member 16 into its closed position while selector element 24 is in its neutral and closing mode position 80 as in FIG. 8. As a result of squeezing lever member 16, anvil member 14 moves to a closed position against cartridge assembly 18. Distal end 64 of pusher 62 still does not engage teeth 68 of tooth rack 66. Proximal end 126 of pusher 62 has dropped away from restraining surface 124 of mode transfer element 120.

Simultaneously, front 88 and back 90 links of locking linking mechanism 56 have pivoted around locking linking mechanism pin 92. Locking linking mechanism 56 locks after links 88 and 90 reach a substantially extended linear configuration. Locking occurs after locking leg 86 is pushed down against locking linking mechanism pin 92 as lever member 16 is squeezed and moves downward. Locking linking mechanism 56 and locking links 88 and 90 remain locked under tension from locking linking mechanism spring 116; anvil member 14 remains in a closed clamping position proximate to cartridge assembly 18. They remain locked even after lever member 16 reverts to its open raised position as in FIG. 13.

It should be remembered that in order for a surgeon to insert stapler 10 into the abdominal cavity with or without a hand port, it is often necessary that anvil member 14 be temporarily closed against cartridge assembly 18. This can be effected in a manner similar to the manner described in the previous paragraph but without clamping tissue. Squeezing lever member 16 is effected outside the body cavity thereby providing a reduced profile for stapler 10. Insertion through the incision or hand port then becomes possible.

FIG. 13, to which reference is now made, shows stapler 10 with selector element 24 still in its neutral and closing mode position, anvil member 14 in its closed, i.e. clamping, position and lever member 16 in its open position. The locking linking mechanism remains in its substantially linear extended position but pusher 62 returns to its restrained position where its proximal end 126 is again held against restraining surface 124. This reversion of lever member 16 to its open position can be effected by main spring 114. Moving selector element 24 to its release position and then squeezing lever member 16 opens anvil member 14 from its closed locked position as will be described herein below. After opening locked anvil member 14, it is possible to reposition the clamped tissue. This is effected by returning selector element 24 to its neutral and closing mode position and squeezing lever member 16. This operation closes anvil member 14 against cartridge assembly 18, again clamping the tissue as described in conjunction with FIG. 12.

FIGS. 14-17, to which reference is now made, show cross-sectional views of stapler 10 while the device is being operated in its stapling and cutting mode. In this mode, selector element 24 and selector mechanism 54 are positioned and operative to provide incremental "stepped" motion of slider assembly 20 in the distal direction by application of a predetermined pushing force. In order to facilitate application of such a predetermined pushing force, selector element 24 is moved distally to its stapling and cutting mode position 82, as indicated in FIG. 10. With lever member 16 in a fully open configuration, distal end 64 of pusher member 62 operationally engages tooth rack 66 of slider assembly 20 at first distal tooth 98 allowing for a pushing force to be applied to assembly 20.

FIG. 14 shows stapler 10 in its stapling mode after selector element 24 has been moved to its stapling and cutting mode position 82 by pressing cut button 25. As shown in greater detail in the upper inset, when cut button 25 is pressed it moves cut button spring 27 proximally in the direction of the proximal end 19 of device 10. Simultaneously, neutral mode spring 29 which holds selector element 24 in its neutral and closing mode is disengaged from element 24. Selector element 24 is then free to move to its stapling and cutting mode position 82. Selector element 24 moves distally as a result of the force exerted by selector spring 118 on selector mechanism 54 which tries to move mode transfer element 120 distally.

In the second insert in FIG. 14 the distal end 64 of pusher 62 is shown engaging first distal tooth 98 in a series of teeth 68 in tooth rack 66.

Moving to FIG. 15, stapler 10 is shown in its stapling and cutting position with lever member 16 down after being squeezed once. Engaged pusher 62, shown in the insert in FIG. 14, pushes on slider assembly 20 moving it one step forward towards the distal end 22 of cartridge assembly 18. As slider assembly 20 proceeds, stapler ejector wedge 48 pushes up on lifter row 36 causing the ejection of one series of staples 50. While moving forward as a result of squeezing lever member 16, blade 46 (not shown) positioned in blade holder 44 moves forward, cutting the tissue clamped between anvil member 14 and cartridge assembly 18.

Turning to FIG. 16 we see lever member 16 returned to its up or open position after the first squeeze shown in FIG. 15. Anvil member 14 is still in its down, clamping position held in place by locking linking mechanism 56, still in its extended substantially linear configuration. FIG. 16 is essentially the same as in FIG. 14 but the distal end 64 of pusher 62 has engaged the second tooth in the tooth rack 66 in FIG. 16 and is ready to advance slider assembly 20 one additional step after lever member 16 is again squeezed.

So as to provide stapling and cutting of the engaged bowel by incremental "stepped" advance of slider assembly 20, lever member 16 is repeatedly squeezed and released, causing pusher 62 to operationally engage the successive teeth 68 of tooth rack 66 while causing advance of tooth rack 66 in the distal direction. Incremental advance of tooth rack 66 in the distal direction causes slider assembly 20 to step-wise traverse its predetermined path along the length of chassis member 12. When slider assembly 20 moves distally, stapler ejector wedges 48 push on staple lifters 36, thereby sequentially ejecting staples 50 from cartridge 21 and successively crimping them against anvil member 14.

Crimping is effected after staple 50 has passed through the engaged bowel portion (not shown) in FIGS. 14-17. The total number of repeated incremental movements required will depend inter alia on the bowel size and on the predetermined geometry of stapler 10.

Figure 21:
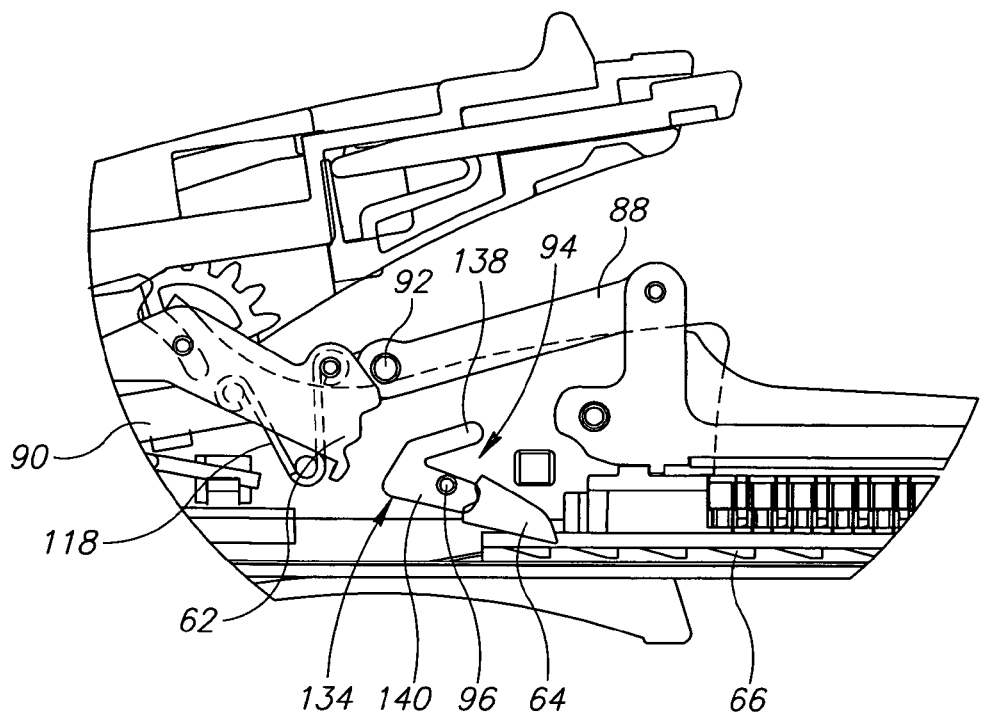
FIG. 21 is an enlarged view of V-shaped groove and guiding pin used in the stapler shown in FIGS. 1-20.

Release mechanism 94, best seen in FIG. 21, remains disengaged while stapler 10 is in its stapling and cutting mode. Guiding pin 96 is retained within and slides proximally in the lower leg 140 of V-shaped groove 134, discussed more fully below in conjunction with FIG. 21.

FIG. 17 shows the last squeezing position of lever member 16 in the stapling and cutting mode. Distal end 64 of pusher 62 is engaged to the last tooth 68 of tooth rack 66. Slider assembly 20 has reached the distal end 22 of cartridge assembly 18 as has blade 46 (not shown). Additional squeezing of lever member 16 will not move slider assembly 20 any further.

The many intermediate squeezing operations have not been shown in the series of FIGS. 14-17, but it is to be understood that each squeeze of lever member 16 incrementally advances the slider assembly 20 the distance of one tooth 68 in tooth rack 66 causing the ejection of a plurality of staples 50 with each step.

It should be noted that in FIGS. 12-17, when anvil member 14 is in its down position clamping tissue to chassis member 12, front 88 and back 90 links of locking linking mechanism 56 are in a substantially linear position essentially locking anvil member 14 in its down, clamping position. Additionally, when anvil member 14 is in its clamping position, cartridge 106 and locking 108 steps are engaged preventing cartridge assembly 18 from moving forward.

Further it should be noticed that in the stapling and cutting mode (FIGS. 14-17), pusher 62 is in a position that allows for engagement of the distal end 64 of pusher 62 with teeth 68 in tooth rack 66 thereby slidably pushing slider assembly 20. This is to be contrasted with the neutral and closing mode where proximal end 126 of pusher 62 abuts restraining surface 124 of mode transfer element 120.

After slider assembly 20 reaches distal end 22 of cartridge assembly 18, pusher member 62 ceases to engage tooth rack 66. If lever member 16 is squeezed again, tooth rack 66 will not advance in the distal direction and the operator will experience no further resisting force from lever member 16.

Additionally, should the geometry of the engaged bowel portion be such that the incremental distal advance of slide assembly 20 has completed the stapling and cutting operations before slider assembly 20 reaches distal end 22 of cartridge assembly 18, no further squeezing of lever member 16 is required and the release mode may be initiated.

Stapling and cutting may be stopped at anytime by bringing selector element 24 to its distal releasing mode position and squeezing lever member 16.

FIG. 18, to which reference is now made, shows a partial cross-sectional view of stapler 10 with its selector mechanism 54 positioned prior to the release and opening of anvil member 14. Selector element 24 has been moved to its releasing mode position 84 as in FIG. 9. Selector mechanism 54, which is in operative association with selector element 24 through mode transfer element 120, turns clockwise, thereby disengaging pusher 62 from tooth rack 66. Guiding pin 96 remains in the lower leg 140 of V-shaped groove 134, the latter shown enlarged in FIG. 21 and discussed below in conjunction therewith. When selector mechanism 54 turns clockwise, selector mechanism spring 118 pushes guiding pin 96 toward the upper leg 138 of V-shaped groove 134. Lever member 16 is shown in its squeezed position.

FIG. 19, to which reference is now made, shows open lever member 16 after the lever has been released with selector element 24 in its releasing mode position 84. As noted above, when selector element 24 is moved to the releasing mode position, mode transfer element 120 moves selector mechanism 54 to the right. As a result selector mechanism spring 118 (FIG. 2) brings pusher 62 to a more upright, but still oblique position, with respect to slider assembly 20. In FIG. 19, guiding pin 96 is guided into the upper leg 138 of V-shaped groove 134, to be described below in conjunction with FIG. 21.

FIG. 20 shows the direction that anvil member 14 pivots (arrow 52B) when anvil member 14 opens after selector element 24 has been moved to its releasing mode position, and after lever member 16 has been squeezed. Anvil member 14 opens because locking links 88 and 90 have pivoted around locking linking mechanism pin 92 from their substantially linear configuration to their "bent" configuration. In FIG. 20, lever member 16 is squeezed and guiding pin 96 is guided to the upper leg 138 of V-shaped groove 134 pushing pusher 62 up. Unlocking surface 132 of pusher 62 pushes against locking linking mechanism pin 92 causing it to move from its substantially extended linear configuration to its "bent" configuration. This causes anvil member 14 to open by pivoting as shown by arrow 52B.

Reference is now made to FIG. 21, where an expanded view of V-shaped groove 134 discussed above in conjunction with FIGS. 18-20 is shown. Riding in V-shaped groove 134 is guiding pin 96 which is connected firmly to pusher 62. V-shaped groove 134 and guiding pin 96 constitute release mechanism 94. V-shaped groove 134, part of chassis member 12, contains upper 138 and lower 140 legs. When selector element 24 is in neutral and closing mode position (FIG. 8) or stapling and cutting mode position (FIG. 9), guiding pin 96 is in the lower leg 140 of groove 134. When selector element 24 is in releasing mode position (FIG. 10), guiding pin 96 moves to upper leg 138.

It should be noted that in most of the previous Figures, groove 134 is not readily seen. Groove 134 is cut out of chassis member 12 and obscured by pusher 62 as presented in the other Figures. It should be noted that chassis member 12 includes in addition to an elongated end a second end that is obscured by chassis cover 28 shown in FIG. 1. In FIG. 21 part of the pusher is cut away revealing groove 134 in its entirety which is cut out of the larger, non-elongated, shaped proximal portion (not shown) of chassis member 12. Cut-out groove 134 can best be seen in FIG. 3B discussed above where the complete chassis member 12 is shown.

Stapler 10 is disengaged from the cut bowel portion and withdrawn from the abdominal cavity, through the incision or through the hand port. Depending on the size of the incision or port, stapler 10 can be withdrawn either directly or lever member 16 may first be squeezed close with selector element 24 in the neutral and closing mode position. In such a case, anvil member 14 would again be brought proximate to cartridge assembly 18 resulting in a reduced profile allowing for easy withdrawal of the stapler.

Figure 22:
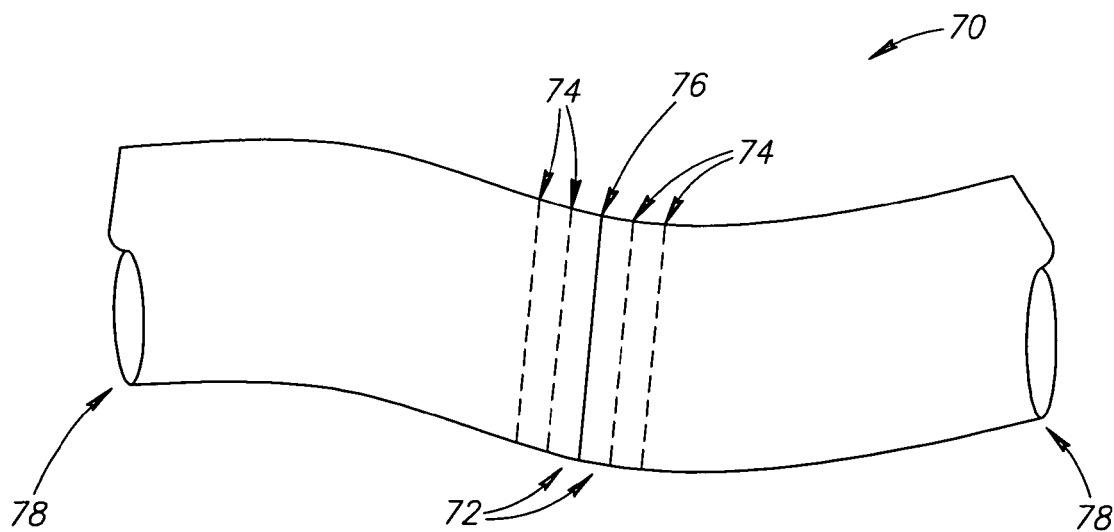
FIG. 22 is a partial perspective view of a portion of bowel indicating stapling and excision.

Referring now to FIG. 22, there is seen a bowel portion 70 having ends 78 subjected to stapling and cutting performed according to the series of operations discussed in conjunction with FIGS. 11-20. The distal movement of slider assembly 20 (FIGS. 14-17) causes stapler ejector wedges 48 to raise staple lifters 36 (FIGS. 3A-3C). Lifters 36 then successively press against two or more generally parallel rows 34 of staples 50, thereby ejecting them from cartridge 21. Staples 50 are pushed against anvil member 14 and are thereby crimped and closed, i.e. forced into a "B" shape. The ejected staples seal both ends 72 of cut bowel 70 between the two or more rows 74 of staples 50. Stapling prevents the contents of bowel 70 from leaking into the peritoneal cavity. As slider assembly 20 advances in a step-wise fashion and after each set of ejected staples 50 is crimped, blade element 46 (FIGS. 3A-3C for example) advances in the distal direction of cartridge assembly 18, cutting bowel 70 along excision line 76 between the two or more rows 74 of inserted staples 50.

In order, for example, to excise a diseased portion of a bowel, a second stapling and cutting procedure, similar to the one described immediately above, is required. This second stapling and cutting procedure provides a second cut to the diseased portion of bowel 70 which effects the total severance of that portion and allows for its removal from the abdominal cavity. Subsequently, ends 72 of bowel 70 are joined by an anastomosis procedure, and continuity of bowel 70 is restored. Anastomosis can be effected using a separate anastomosis device or the stapler of the present invention.

In order, for example, to effect side-to-side anastomosis of the two stumps of the stapled and cut bowel, a third stapling and cutting procedure is required. In this third stapling and cutting procedure, the two stumps are positioned side-to-side either in the same or in opposite directions.

Two close enterotomies are made, one in each lumen. The anvil and the cartridge assembly are introduced simultaneously all the way through each one of the enterotomies. When positioned the anvil is closed over the cartridge assembly, clamping the adjacent walls of the two lumens to each other. In this position, the lever is pressed and stapling and cutting occurs in between the previously stapled lines. When the stapling process is completed, the device is opened and removed from the lumens with the enterotomies closed either by stapling or suturing.

It should be understood that locking linking mechanism 56, which appears inter alia in FIGS. 2 and 12-20 discussed above, acts as a toggle mechanism. The mechanism includes two links which are brought into substantially extended linear configuration and self-lock in that configuration. Anvil member 14 is closed when links 88 and 90 of locking linking mechanism 56 are in a substantially extended linear configuration; anvil member 14 is opened when locking linking mechanism 56 reverts back to its original "bent" configuration as shown, for example, in FIG. 2. The extended substantially linear configuration may, and usually does, exceed a linear configuration with the angle centered on pin 92 between locking links 88 and 90 being somewhat greater than 180°. This latter case may also be described herein as the "over center" position. Alternatively, the angle may be somewhat less than 180°. This latter configuration may also be described herein as the "under center" configuration. In this latter case, a latch mechanism discussed in conjunction with FIGS. 24A-24E below may be used to hold the links in a locked configuration. However, the angle of the original "bent" configuration, i.e. with knee 142 as in FIG. 2, is always substantially less than 180°. It should also be readily apparent to a person skilled in the art that while locking linking mechanism in the Figures presented show the mechanism as including two links, other embodiments may contain more than two links.

Figure 23A:
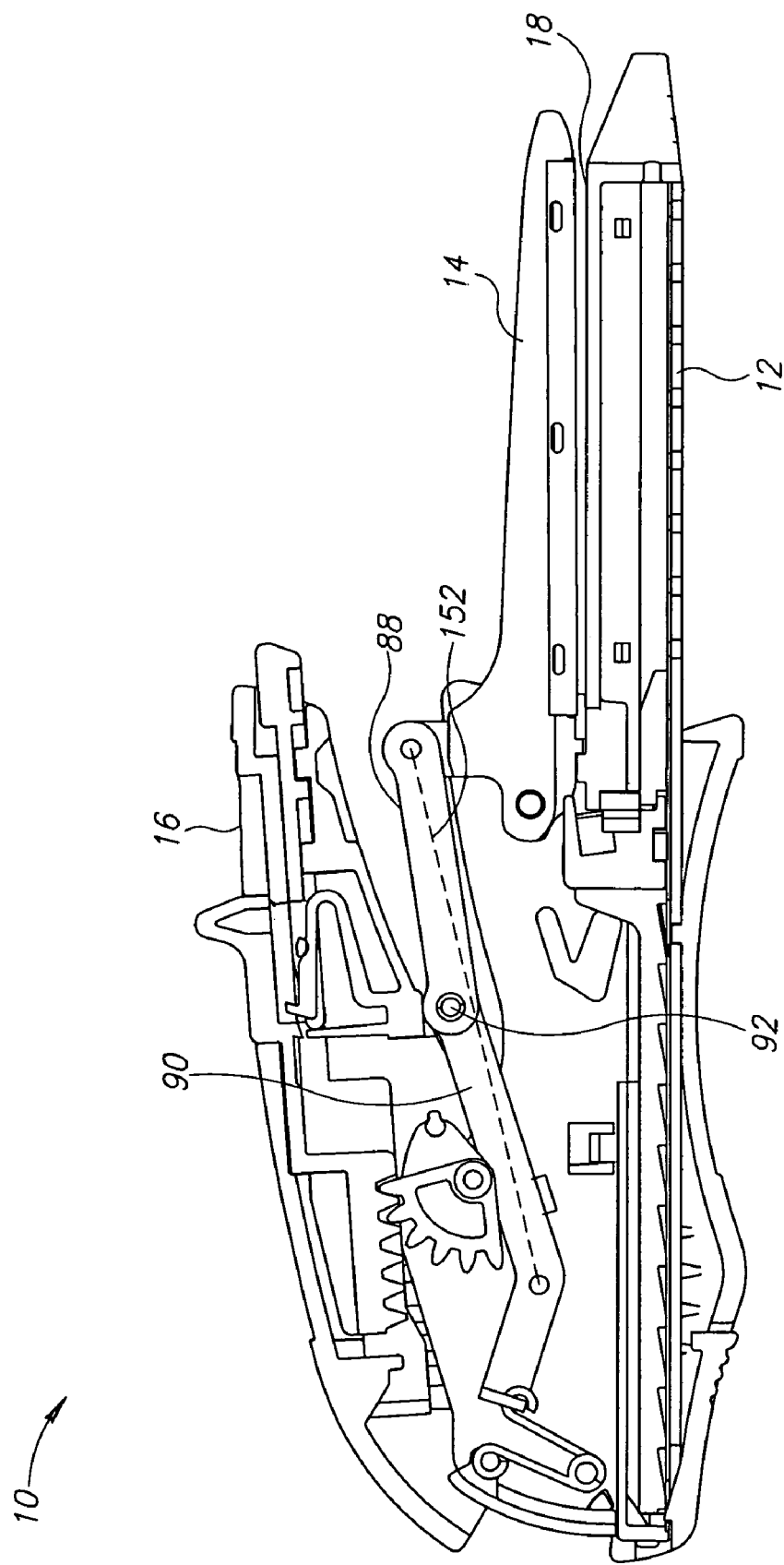
FIGS. 23A-23C are views of the under center, substantially linear, and over center positions respectively of the locking linking mechanism of the stapler of the present invention.
Figure 23B:
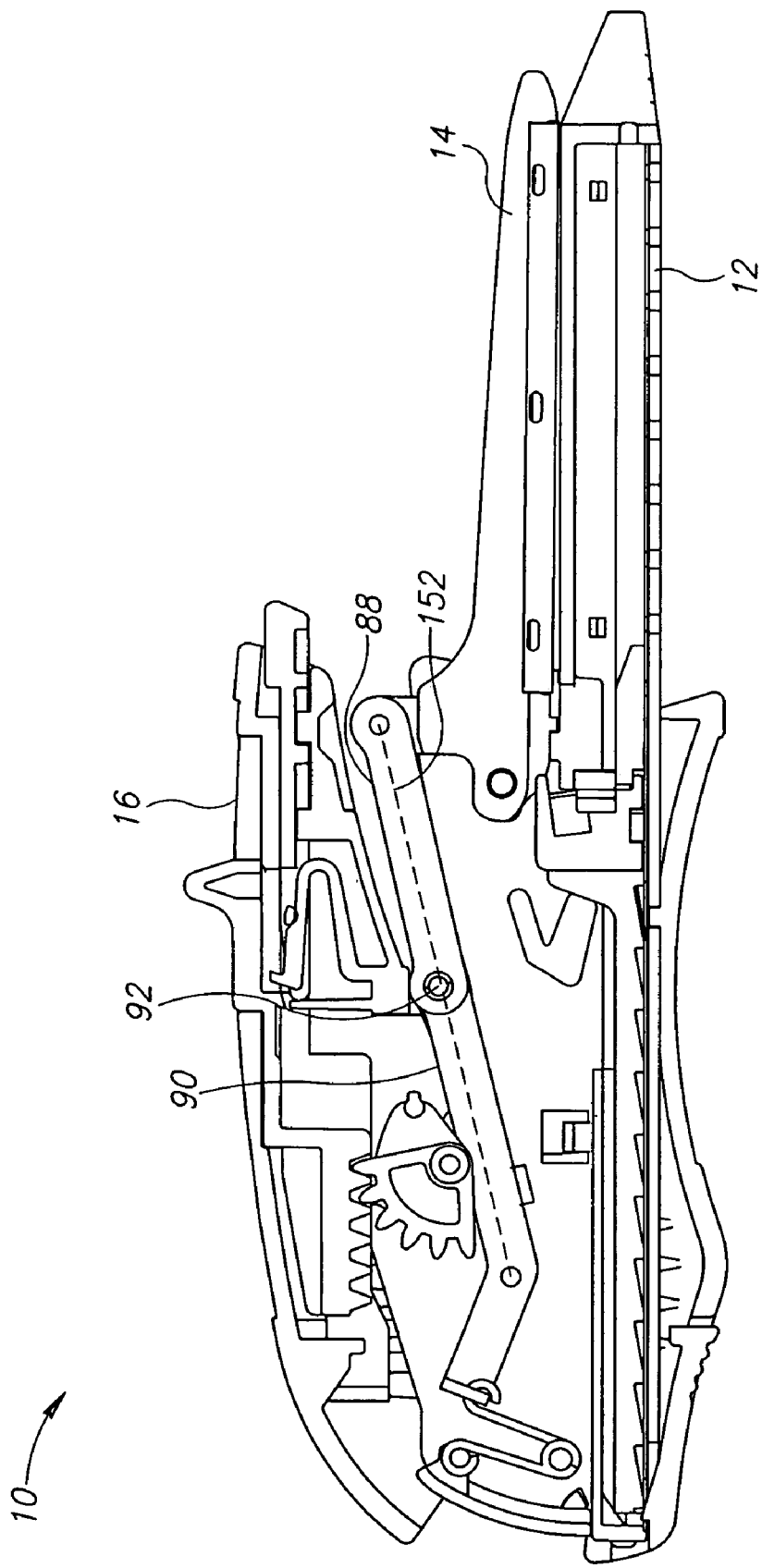
Figure 23C:
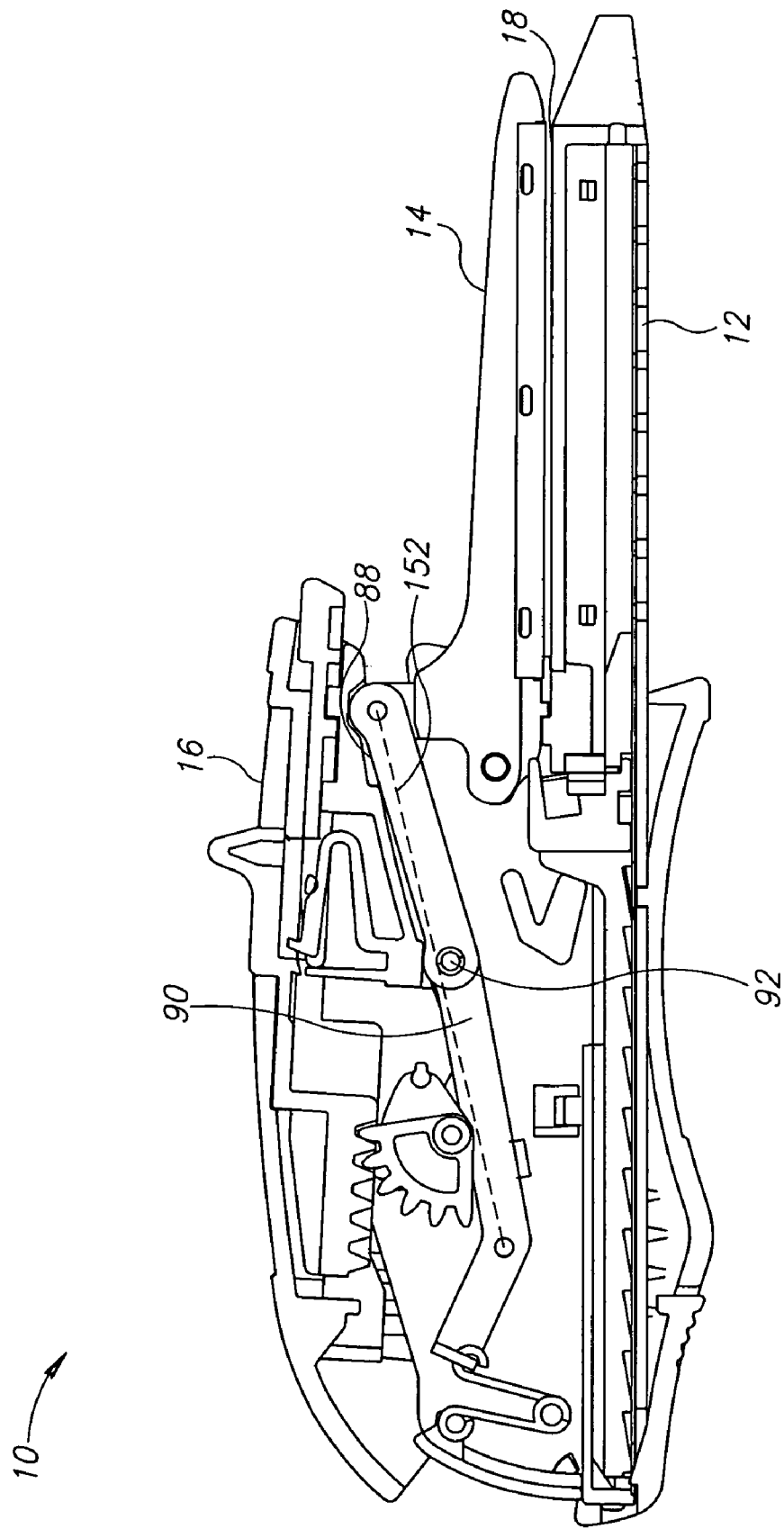

FIGS. 23A-23C, to which reference is now made, show the "under center", "substantially linear" and "over center" relationship respectively of links 88 and 90 in the locking linking mechanism 56 of the present invention. This is best seen by viewing hatched line 152 in the Figures. In FIG. 23B, line 152 represents the substantially linear position with a substantially straight line running through locking linking mechanism pin 92, the line being formed by fully extended links 88 and 90. Pin 92 may be in an under or over center position as shown in FIGS. 23A and 23C respectively; typically, the present invention is constructed to operate in the latter configuration.

Reference is now made to FIGS. 24A-24E which represent one possible latch mechanism for locking the locking linking mechanism 556 when the linking mechanism 556 is locked in an "under center" position. FIGS. 24A-24E emphasis the novel aspects of the latch mechanism and do not include those elements, such as the pusher-ratchet mechanism, described in conjunction with FIGS. 1-21 above. In the embodiment of FIGS. 24A-24E, these operate in a manner similar to that discussed previously. Accordingly, no additional description will be provided relating to previously described elements. In FIGS. 24A-24E elements identical to those in the embodiment of FIGS. 1-21 have been given identical numbers but with a prefix "5". Only some of the previously identified parts will be labeled. These are intended primarily as a way of orienting the reader in regard to the construction and orientation of the latch mechanism.

Figure 24A:
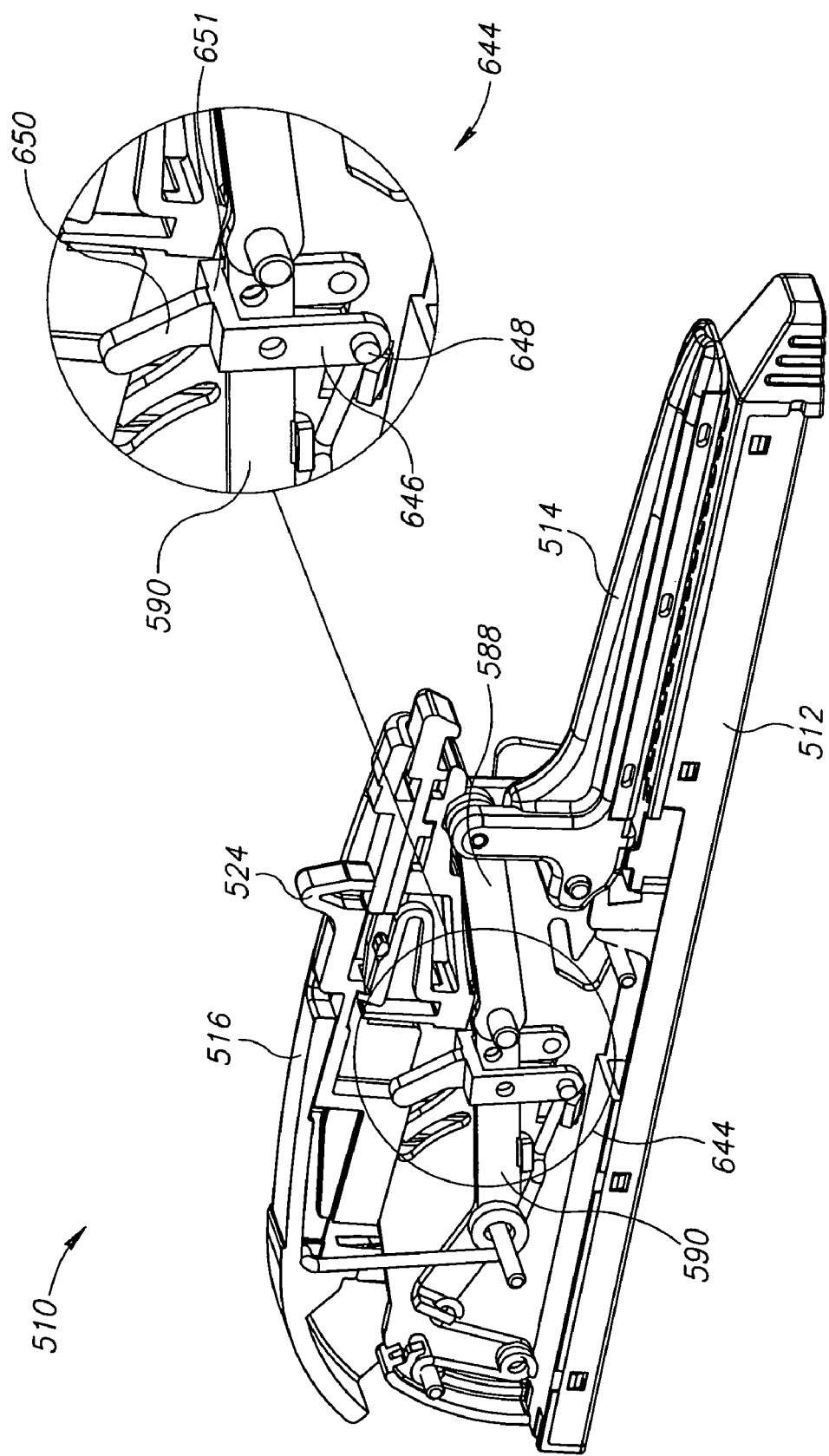
FIG. 24A is an isometric view of a latch mechanism for locking the stapler of the present invention.

FIG. 24A is an isometric partial sectional view of stapler 510 including latch mechanism 644. An inset in FIG. 24A shows the detailed construction of latch mechanism 644. Mechanism 644 includes latch legs 646, latch protrusion 648, and a latch arm 650 extending from latch bridge 651. Latch mechanism 644 is rotatably attached to back link 590 with a screw (not shown) and is spring (also not shown) loaded.

Figure 24B:
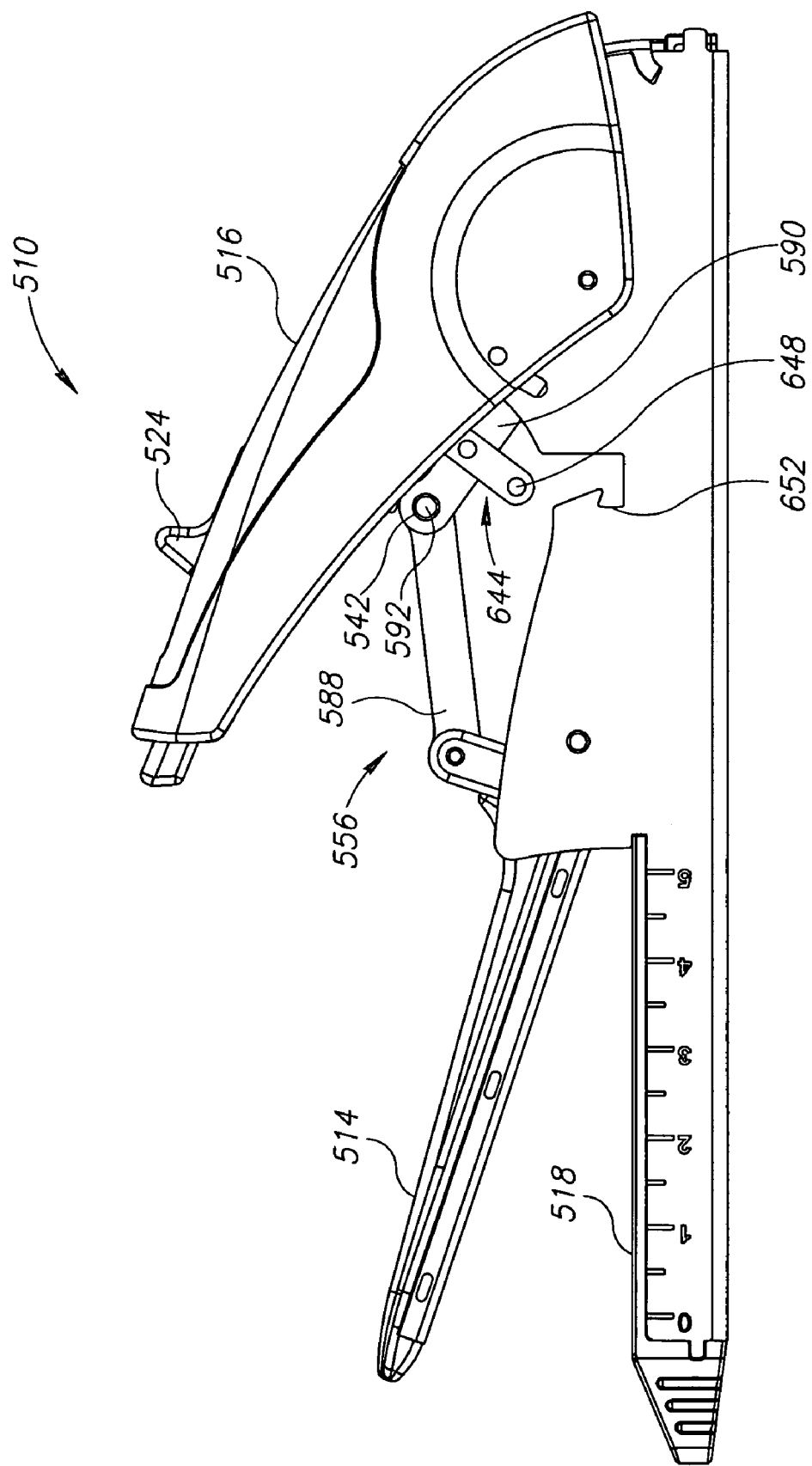
FIGS. 24B-24E are views of the different stages of operation of the latch mechanism shown in FIG. 24A.
Figure 24C:
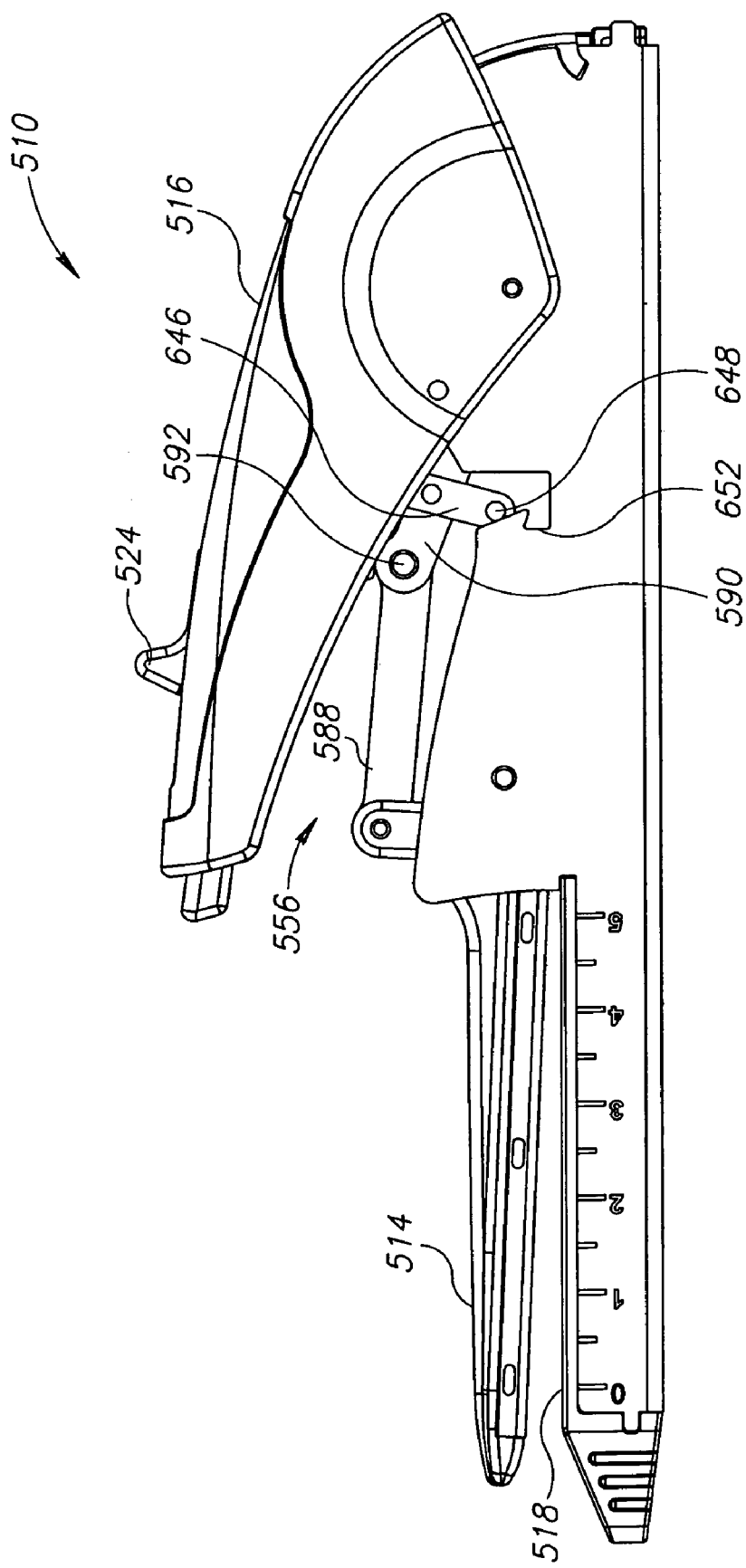
Figure 24D:
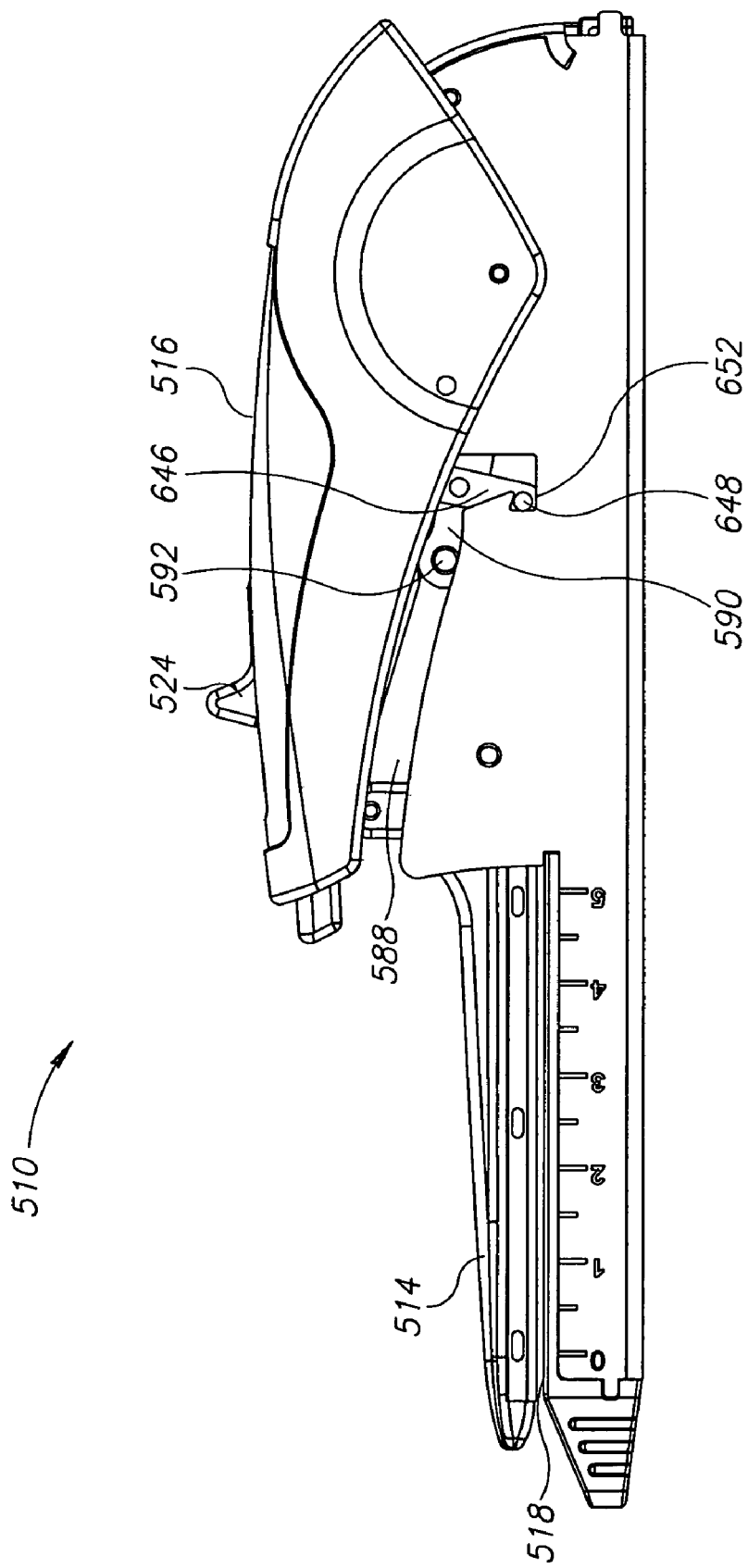
Figure 24E:
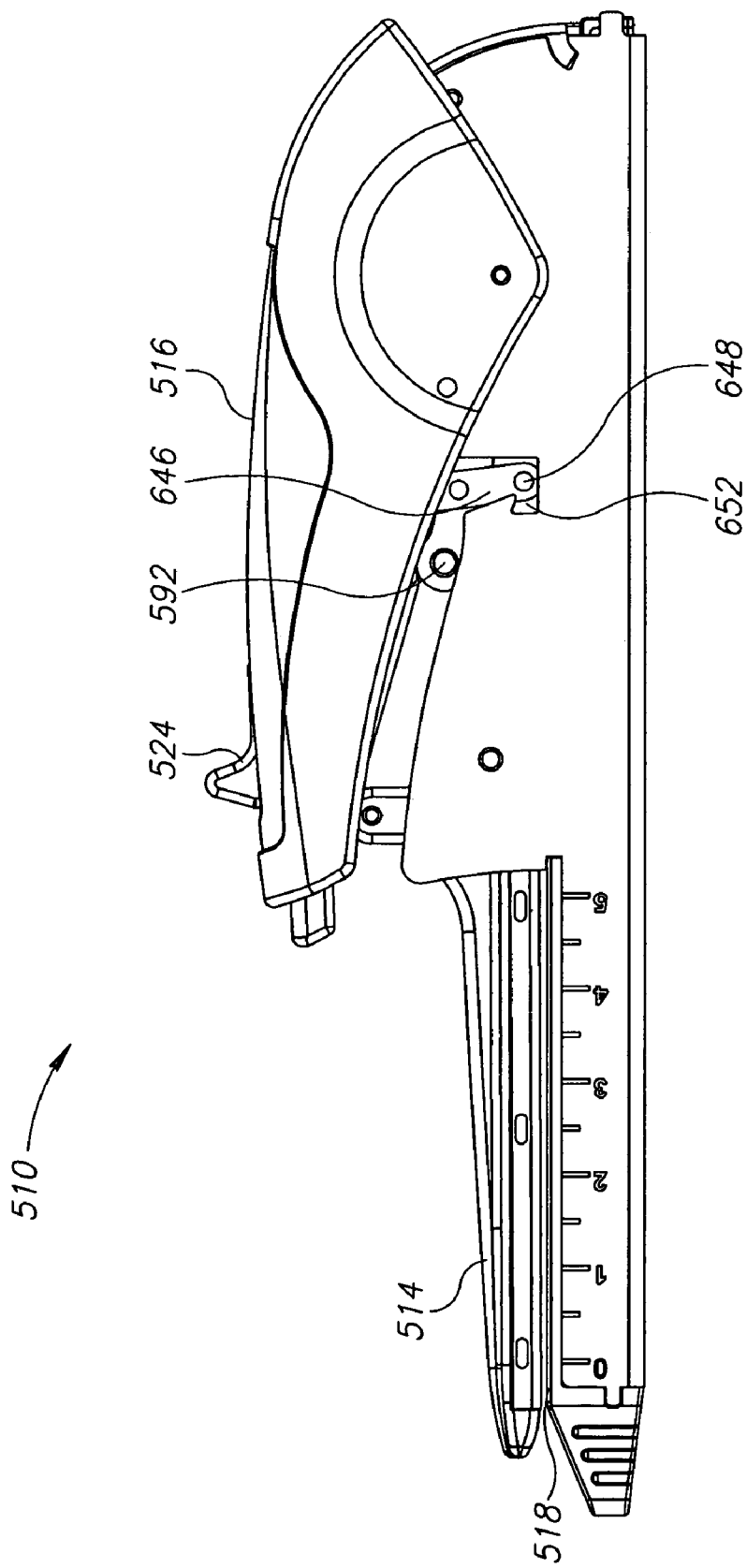

FIG. 24B shows the open position of stapler 510 as well as the position of latch mechanism 644 when stapler 510 is in that position. FIG. 24C shows the locking linking mechanism as it begins to close. Latch mechanism 644 slides on an incline 654 of latch receiving groove 652 towards its engaged position therein. FIG. 24D shows latch mechanism 644 in its locked position. It should be noted that links 588 and 590 do not form a linear configuration but remain slightly bent at locking mechanism pin 592 in an "under center" position. The two links remain in this configuration because latch protrusion 648 is held in latch receiving groove 652, preventing bending of the locking linking mechanism 556. FIG. 24E shows the release of latch mechanism 644, the release being actuated only after pushing selector element 524 distally.

As can be readily seen, as lever member 516 is squeezed, it contacts and presses on the knee 542 of locking linking mechanism 556. As a result latch mechanism 644 moves downward together with back link 590 and rotates slightly as it meets incline 654 until it reaches latch receiving groove 652. When it reaches groove 652, latch protrusion 648 enters the groove, thereby retaining links 588 and 590 in a locked, "under center" position while holding anvil member 514 proximate to cartridge assembly 518. Latch protrusion 648 of latch mechanism 644 moves outward from receiving groove 652 when selector element 524 is moved distally to its open position. This outward movement unlocks the locking linking mechanism 556 formed, in part, by links 588 and 590.

Using a latch mechanism 644 as in FIGS. 24A-24E allows the stapler's 510 locking linking mechanism to be locked in an "under center" configuration that is at an angle formed around pin 592 of less than 180°. This angle is best seen in FIG. 24A and FIG. 23A as the angle is obscured in FIGS. 24B-24E.

It should be readily understood that other latch mechanisms or their equivalents may also be used. The latch mechanism illustrated in FIGS. 24A-24E and discussed in conjunction therewith is exemplary only and is not to be considered limiting.

In another embodiment, latch mechanism 644 may be attached to the chassis and not to back link 590. In such an embodiment, the latch can engage with locking linking mechanism pin 92 when holding locking linking mechanism 556 in its locked position.

Incremental drive mechanisms other than the pusher-ratchet mechanism discussed above may be used in other embodiments of staplers constructed according to the present invention.

Figure 25A:
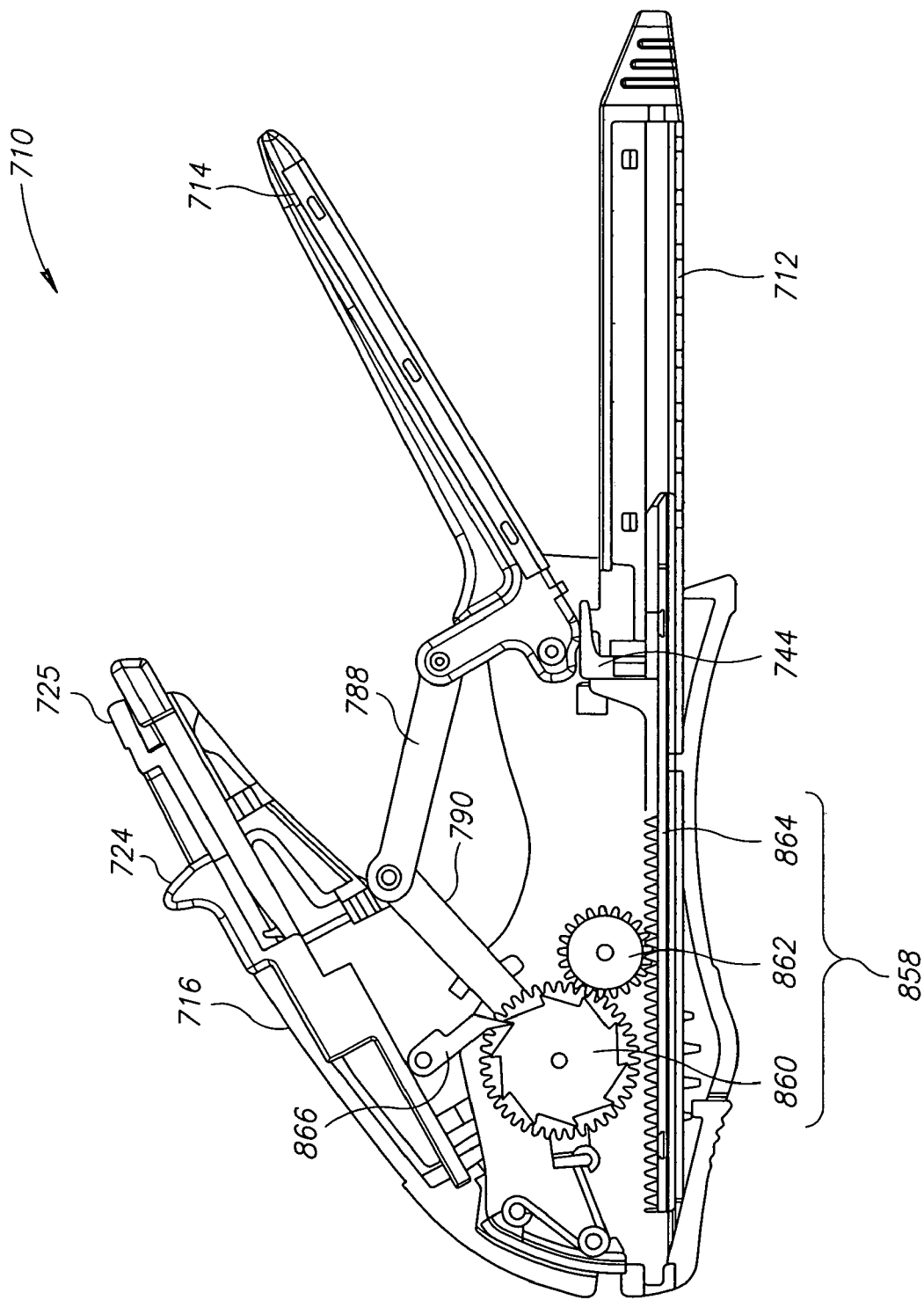
FIGS. 25A-25B are two views of an incremental drive mechanism based on gears for the stapler of the present invention.
Figure 25B:
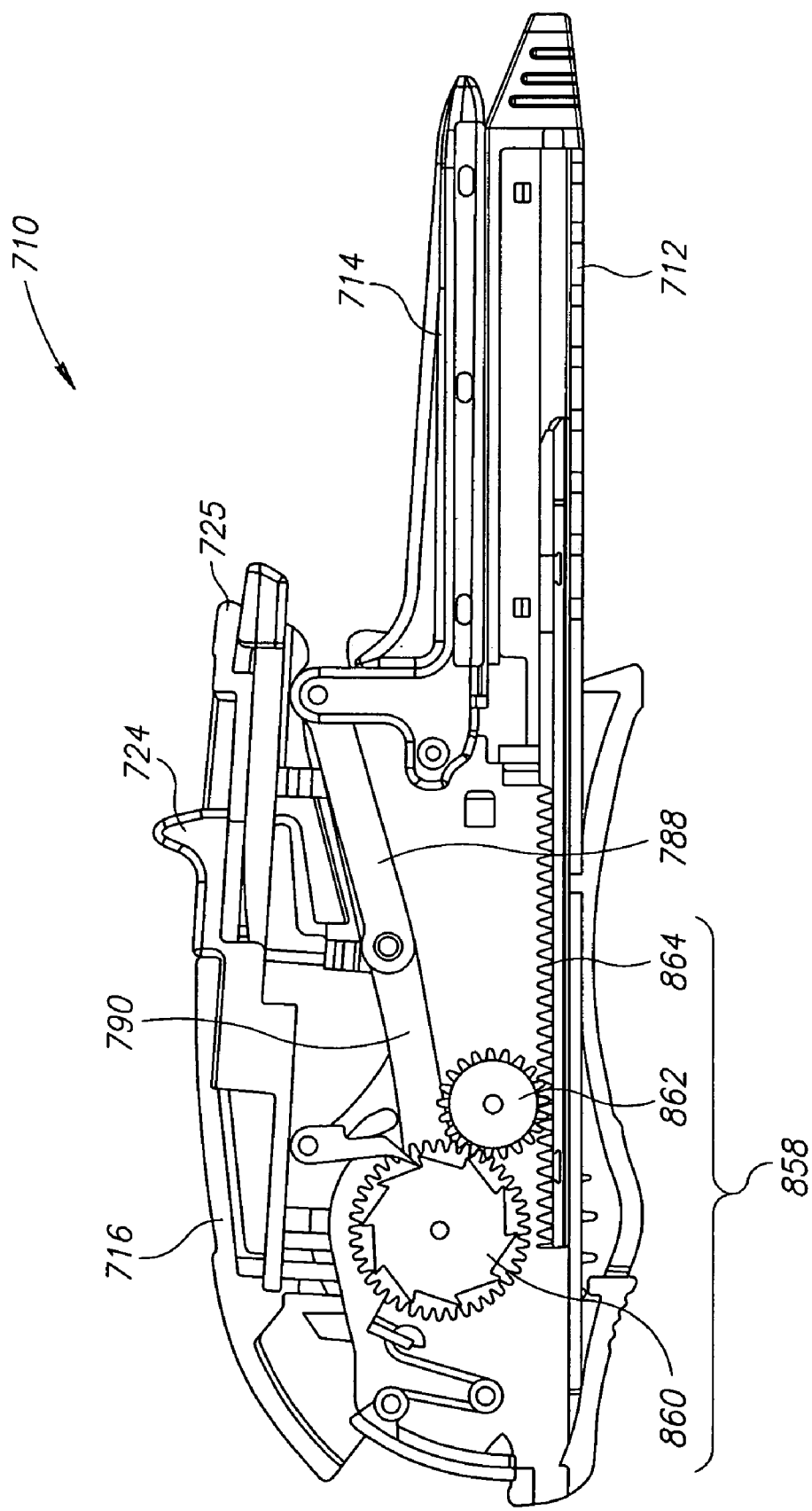

In another embodiment of the present invention, the incremental drive mechanism may be a gear mechanism. A stapler 710 containing a gear mechanism 858 is shown in FIGS. 25A-25B. FIG. 25A shows stapler 710 in its open position while FIG. 25B shows stapler 710 in its closed operative position. Parts similar in construction and/or operation to those discussed previously have been given the same numerals but with a prefix of "7" and will not be discussed in conjunction with FIGS. 25A-25B. Similarly, many elements have remained unnumbered as they have been discussed above in conjunction with FIGS. 1-21 and do not relate directly to the new feature, gear mechanism 858, discussed here. Only the new features of the drive will be described in this additional embodiment.

Gear mechanism 858 includes a large gear 860 which is engaged with a small gear 862. The latter during operation further engages with gear rack 864. Large gear 860 is operated by gear pusher 866 which is engagable with the teeth of gear 860. When lever member 716 is in its open position, gear pusher 866 is disengaged from large gear 860. When lever member 716 is squeezed, gear pusher 866 moves downward and engages with large gear 860 turning and advancing small gear 862 one tooth in gear rack 864 causing rack 854 to advance one "step".

After each additional squeeze of lever member 716, gear rack 864 advances incrementally in a step-wise fashion one tooth at a time. In front of gear rack 864 and in operative attachment therewith are staple wedges and a blade element, very similar to those shown inter alia in FIGS. 2-3C. The former lifts staple lifters much as do the wedges in the slider assembly associated with the pusher-ratchet mechanism described in conjunction with FIGS. 1-21. Stapling and cutting proceeds in the fashion described previously in the embodiment of FIGS. 1-21. The control of the operational mode of stapler 710 is effected by selector element 724 which is operative much the same as described previously with previous embodiments. It should be noted that the locking linking mechanism shown in FIGS. 25A-25B is also operative as in previously described embodiments and its description will not be repeated here.

Figure 26A:
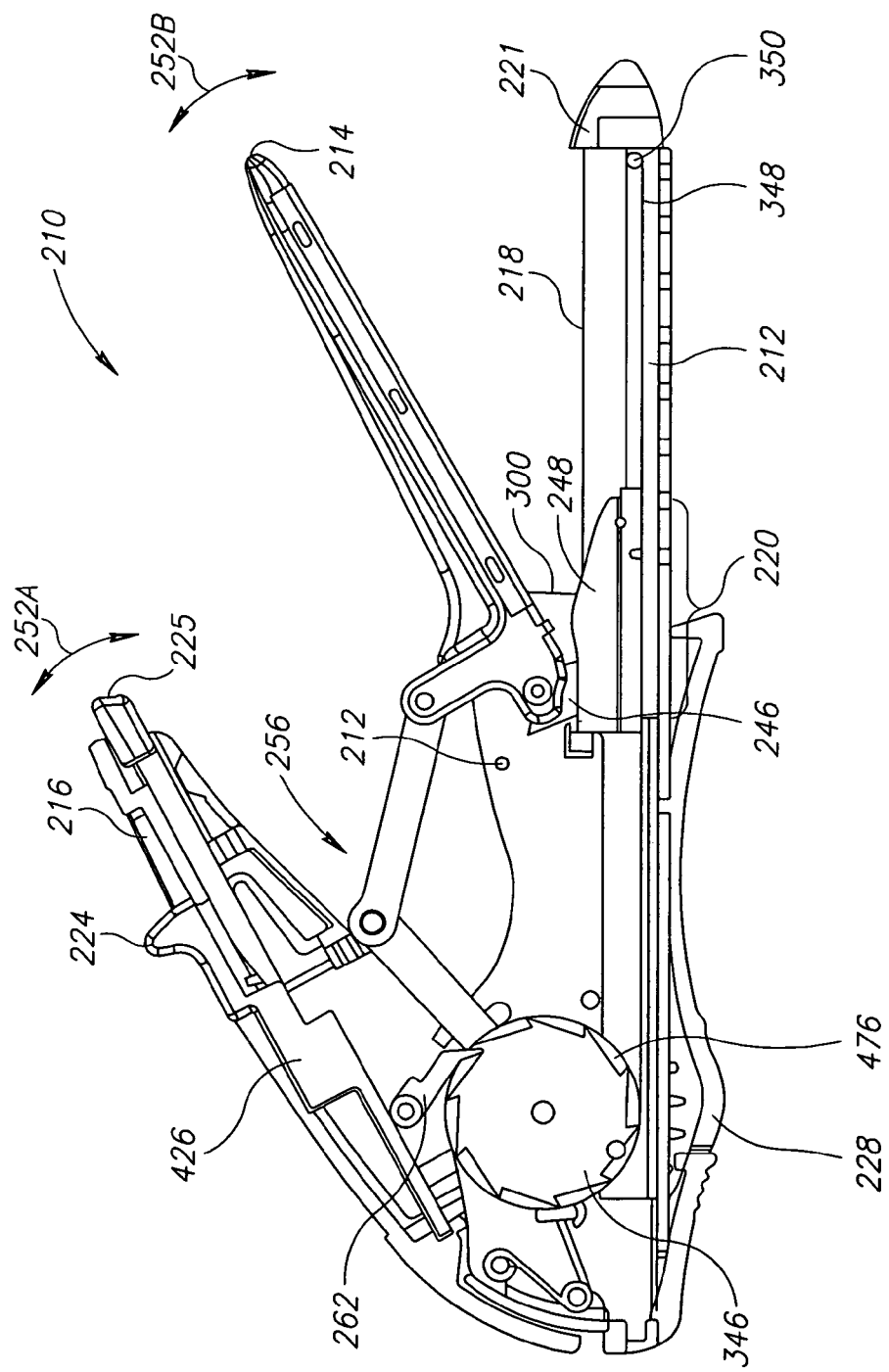
FIGS. 26A-26B are two views of an incremental drive mechanism based on a pulley for the stapler of the present invention.
Figure 26B:
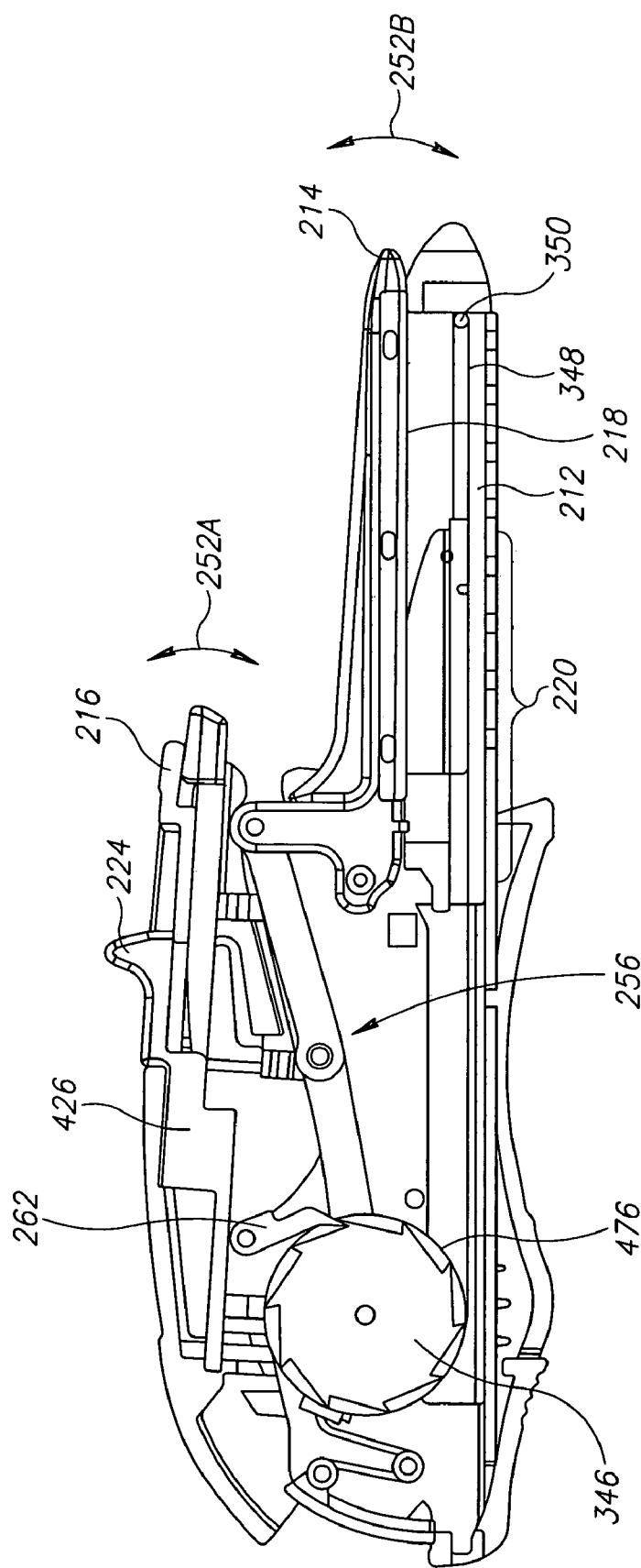

Yet another embodiment of the incremental drive mechanism, a pulley system, for the stapler of the present invention, is shown in FIGS. 26A and 26B. FIG. 26A shows stapler 210 in its open position while FIG. 26B shows stapler 210 in its closed position. Parts similar in construction and/or operation to those discussed previously in conjunction with FIGS. 1-21 are given the same numerals as in those Figures but with a prefix of "2" and will not be discussed further. Only the new features of the pulley mechanism will be described here. Additionally, many elements have remained unnumbered as they have been discussed elsewhere and will not be discussed again.

The operative novel feature here is the pulley which includes a rotating drum 346 to which wire 348 is attached and around which wire 348 is wound. Near the end of cartridge assembly 218 is a wire axis pin 350 around which wire 348 is positioned and then attached to slider assembly 220.

Rotating drum 346 is constructed to have teeth along its periphery. In engagement with the teeth of rotating drum 346 is drum pusher 262. A ratchet mechanism (not shown) permits rotation of the drum only in the clockwise direction. When lever member 216 is brought from its open to its closed position as from its position in FIG. 26A to FIG. 26B, drum pusher 262 engages with and pushes on the teeth of drum 346 in a step-wise fashion. As a result, rotating drum 346 rotates clockwise incrementally, winding wire 348 around drum 346. This winding action pulls on and moves wire 348 in a step-wise fashion. As in previous embodiments, lever member 216 is repeatedly squeezed causing step-wise incremental rotational movement of drum 346. As a result of winding wire 348 around drum 346, step-wise incremental linear motion is imparted to the slider assembly 220 as it is pulled along its predetermined path in the chassis member 212.

As noted, the second end of the wire is attached to slider assembly 220. As the wire is wound step-wise around drum 346, the slider assembly 220 is pulled and moves distally in the direction of wire axis pin 350. As slider assembly 220 moves, it staples and cuts tissue held between anvil member 214 and cartridge assembly 218 as described in previous embodiments. Staples are ejected and crimped as described previously; slider assembly 220 includes staple wedges (not shown) which lift staple lifters of cartridge assembly 218. Cutting is effected by a cutting blade (not shown). Selector element 224 selects between the operational modes as discussed above in conjunction with the embodiment of FIGS. 1-21. Similarly, locking linking mechanism 256 operates as discussed above.

Repeatedly releasing and squeezing lever member 216 causes slider assembly 220 to traverse the length of chassis member 212 in the distal direction and to successively eject all staples from cartridge assembly 218. The number of repeated releasing and squeezing movements depends on the bowel size and the predetermined geometry of stapler 210.

When slider assembly 220 reaches the most distal position of chassis member 212, drum 346 is released from the ratchet mechanism (not shown) to allow free rotation of drum 346. This permits unrolling wire 348 from about drum 346 while pulling blade assembly 246 to its extreme proximal position in chassis member 212. Replacement cartridge assembly 218 and replacement blade assembly 246 are fixed in position relative to chassis member 212. Stapler 210 is then again ready for use.

It should readily be understood that in accordance with another preferred embodiment of the present invention, the wire can be configured to wind around the rotating drum and the pusher can be configured vis-a-vis the teeth on the drum so that the slider assembly may be made to move in the proximal direction instead of the distal. This may be accompanied by appropriate modification of the ratchet mechanism in association with the drum.

The operation of the pulley embodiment was discussed in terms of a wire. It is readily understood by one skilled in the art that a band or the like can be used instead of a wire.

It should be noted that the anvil shown and discussed herein with its funnel-shaped recesses (FIGS. 6A-6D and discussion therewith) may be used with any stapling device to ensure proper crimping of the staples. Stapling devices which can use such an anvil include other linear, curved and circular staplers.

In the embodiments above, the selector element has been shown positioned on the lever element. However in other embodiments the selector element can be positioned at other locations of the stapler, such as on the chassis. In all cases, the selector element must be capable of selecting the operative mode of the stapler and be in operative association with the locking linking mechanism and the release mechanism. Similarly, it should be operable by the user with one hand.

While we have presented embodiments with a single selector element in other embodiments of the present invention, the stapler may employ two or more selector elements. Each of these selector elements would select between at least two operational modes of the stapler and each of the elements should be operable by the user with one hand.

In the embodiments of the stapler discussed above, the selector element has been described as selecting between three operative modes. It is readily understood that the one or more selector elements of the stapler may be operative to choose between a plurality of operative modes where the number of operative modes is at least two.

In the above discussion the stapler has been described as being used in bowel resections. It should be evident to one skilled in the art that other organs can also be resected using the stapler of the present invention with little or no modification. Such organs include, but are not limited to, the uterus, esophagus and lungs.

It should be readily apparent to one skilled in the art that the device and method of the present invention can be used to excise tissue of animals as well as humans particularly, but without being limiting, other mammalian species.

In yet another embodiment of the present invention a palm size surgical stapler suitable for single hand operation includes a locking mechanism and an actuating mechanism that operate in a scissor-like fashion. Additionally, no selector mechanism is required. Removal of the selector button makes possible even easier single hand operation of the device and it reduces physician confusion and misuse of the stapler. Additionally, the structural complexity introduced by use of a selector element is eliminated. The increased effective length of the anvil member in this embodiment resulting from joining it to its anvil frame allows for greater accuracy when the anvil is brought into proximity and apposition with the cartridge assembly positioned in the distal portion of the chassis member. The construction of the stapler in this embodiment also allows for operating the stapler with less force. In FIGS. 27-36 relating to this embodiment, elements substantially identical to those shown in the embodiments of FIGS. 1-26B are numbered similarly. The function and operation of these elements will not be described again as they have been described above.

Figure 27:
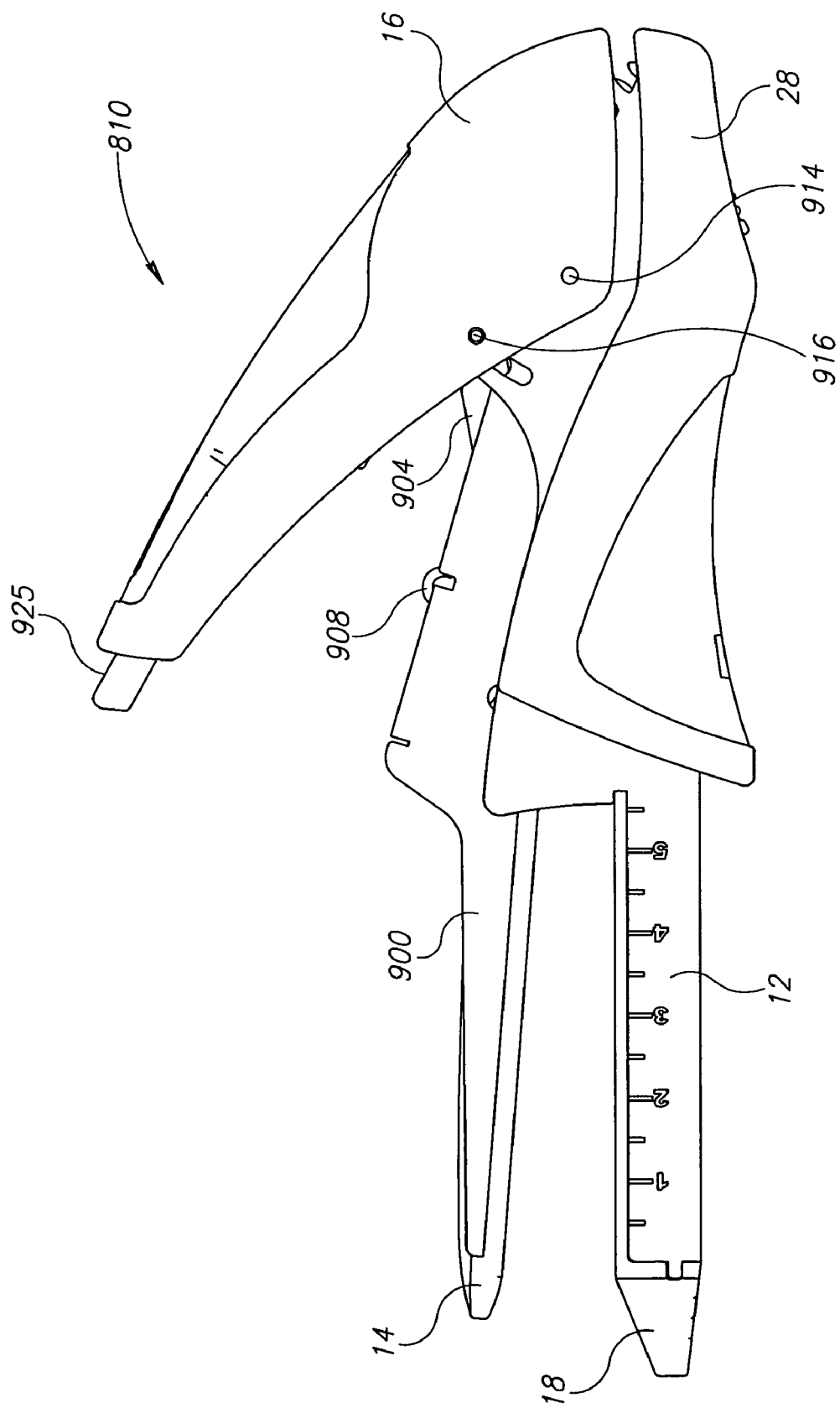
FIG. 27 is a view of a stapler constructed according to another embodiment of the present invention.
Figure 28:
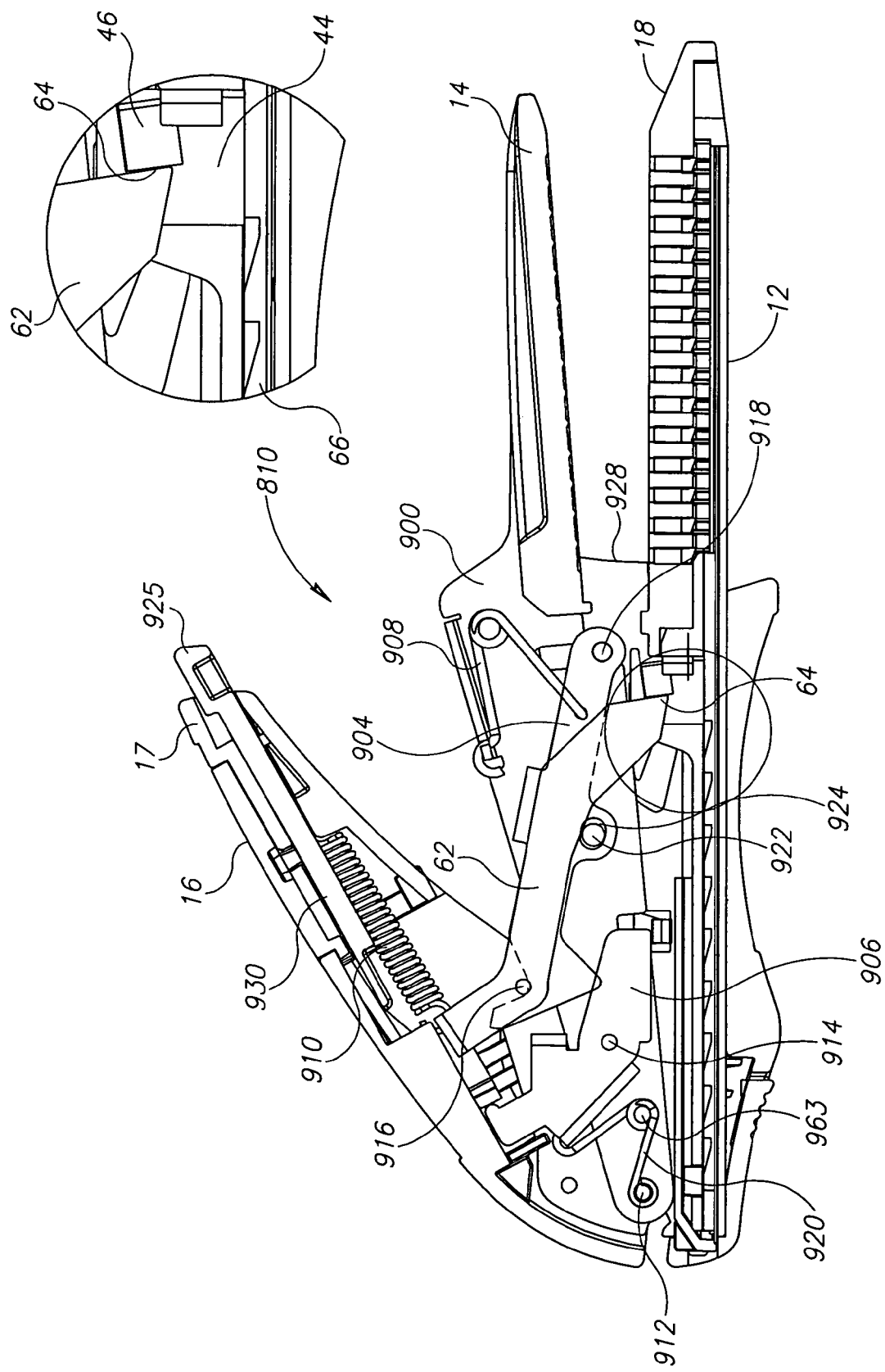
FIG. 28 is a cut-away view of the stapler shown in FIG. 27 which also includes a detail view of the pusher and the teeth of the slider assembly.

Reference is now made to FIGS. 27 and 28 which show an external view and a cut-away view, respectively, of a stapler 810 constructed according to the embodiment of the present invention discussed in the preceding paragraph. FIG. 27, the external view, is very similar to the one shown and discussed above in conjunction with FIG. 1. In this embodiment of the invention, as can readily be seen in FIGS. 27 and 28, there is no selector element and no selector mechanism.

Anvil member 14 is attached directly to anvil frame 900 forming a rigid, or substantially rigid, compound anvil member. Anvil member 14 and anvil frame 900 are typically, but without intending to be limiting, made of metal injection molding and sheet metal, respectively. These parts may be joined by any of several methods known in the art, such as, but again without intending to be limiting, laser welding. It is contemplated that in some cases these parts may also be made of plastic and joined by any known appropriate method. It is further contemplated that in some cases these two pieces may be integrally formed as a single piece. The joined anvil member-anvil frame's (at times referred to herein as "compound anvil member") greater effective length, allows for better alignment between anvil member 14 and the staple cartridge (best seen in FIGS. 3A-3C as element 21) positioned in the extended "snout-like" distal portion of chassis member 12. It also allows for the use of less force during operation of stapler 810.

In what is described herein with regard to the embodiment shown in FIGS. 27-36, "proximal" relates to the side of the stapler or element of the stapler closest to the user, while "distal" refers to the side of the stapler or element of the stapler furthest from the user. To properly orient the position of the user, element 18 in FIGS. 27 and 28 is positioned near the distal end of stapler 810 while element 912 (FIG. 28) and element 28 (FIG. 27) are located near its proximal end.

Figure 29:
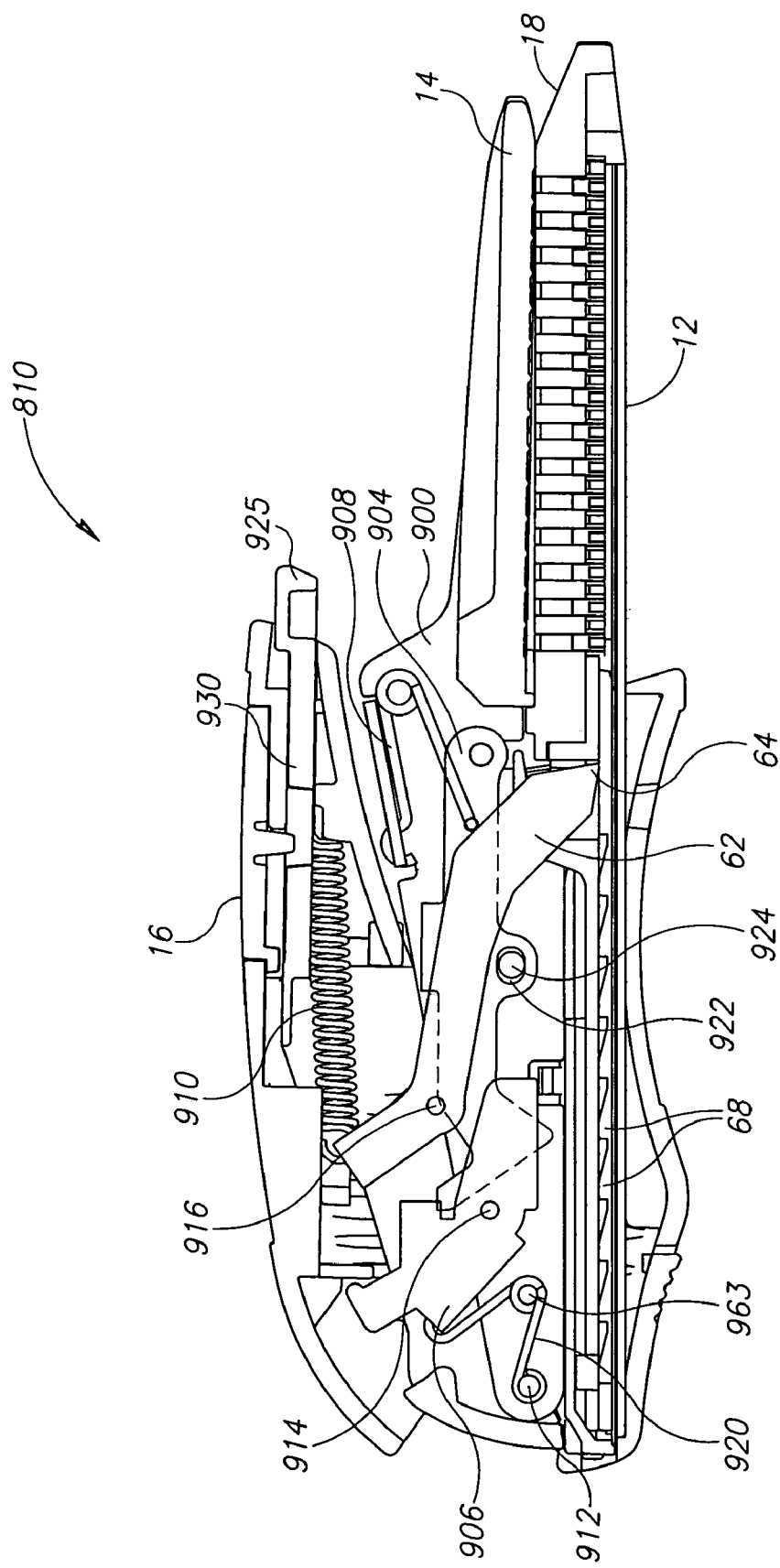
FIGS. 29-36 show the steps of operation of the stapler shown in FIG. 27.

FIG. 28 shows a cut-away view of stapler 810 in the stapler's open configuration. In this configuration, anvil member 14 is spaced apart from the distal portion of chassis member 12. FIG. 29, to be discussed below, shows a cut-away view of stapler 810 with the stapler in its closed configuration. In the stapler's closed configuration, anvil member 14 is held proximate to cartridge assembly 18, the latter positioned in the extended distal portion of chassis member 12, with tissue (not shown) to be stapled and cut held therebetween. A fully exposed view of chassis member 12, not just its distal end, is best seen in FIG. 3B. It should be understood that element 134 shown there is not necessarily required in the present embodiment.

Stapler 810 contains a slider assembly (best seen in FIGS. 3A-3C as element 20), which contains a tooth rack 66 with teeth 68. It also contains a cartridge (best seen in FIGS. 3A-3C as element 21) containing staples (best seen in FIGS. 3A-3C as element 50) positioned within cartridge assembly 18 in the distal portion of chassis member 12. The construction, function and operation of these elements have been discussed above; accordingly, these will not be discussed again.

Stapler 810 also contains a blade member 44 held in a blade holder 46 and a wedge (best seen in FIGS. 3A-3C as element 48) and lifters (best seen in FIGS. 3A-3C as element 36) mechanism for ejecting staples (best seen in FIGS. 3A-3C as element 50) from the cartridge (best seen in FIGS. 3A-3C as element 21). The wedge and lifters mechanism for ejecting staples from the cartridge has also been discussed above.

Stapler 810 in FIGS. 27-36 contains an anvil member 14 and a chassis member 12 which are very like those described in previous embodiments. A perspective bottom view of stapler 810 would be essentially the same as that shown in FIG. 7 but without the selector element 24 shown in that Figure. Accordingly, these elements and their operation will also not be discussed again.

FIG. 28 shows a lever 16 having a distal end 17 at which is positioned a release button 925. When lever 16 is pressed, it rotates in the closed direction that is in the direction of anvil member 14. Joined to lever 16 is lever spring 910 which is biased to cause lever 16 to return to its open position after pressure exerted on lever 16 is removed.

Also shown in FIG. 28 is scissor pin 922. Pin 922 is connected to anvil frame 900 and acts as an axis point for locking link 904. Locking link 904 includes an eccentric oval aperture 924 which moves relative to scissor pin 922. Pin 922 also serves as a support point for pusher 62 when pusher 62 engages and disengages from tooth rack 66 of the slider assembly (best seen in FIGS. 3A-3C as element 20). The slider assembly functions as part of the incremental drive mechanism as described in previous embodiments.

When locking link 904 is in its locked, substantially horizontal, position, it rests against and is arrested by anvil locking element 906. When locking link 904 is locked, anvil member 14 is held proximate to and in apposition with cartridge assembly 18, positioned in the extended distal portion of chassis member 12, in which a staple cartridge (best seen in FIGS. 3A-3C as element 21) is positioned.

Anvil locking element 906 is held on chassis member 12 by anvil locking element pin 914. Again it should be remembered that chassis member 12 is constructed substantially as shown in FIG. 3B even though its full construction is obstructed in FIGS. 27-36. Element 906 is also in operational association with chassis member 12 and axis pin 912 by anvil locking link element spring 920. Spring 920 is joined at one end to anvil locking element 906 and at the other end to axis pin 912.

Attached to the distal end of anvil frame 900 is anvil spring 908. Spring 908 is connected at one end to anvil frame 900 and at the other to locking link 904. When locking link 904 is locked against anvil locking element 906, anvil member 14 is held proximate to the distal portion of chassis member 12, and anvil spring 908 is compressed (FIG. 29). Spring 908 is biased to allow anvil member 14 to rotate away from the distal portion of chassis member 12 when locking link 904 is released and no longer held and immobilized by anvil locking element 906.

FIG. 28 shows pusher 62 which pushes the slider assembly (best seen in FIGS. 3A-3C as element 20) and tooth rack 66 contained therein substantially as described in conjunction with FIGS. 11-20. The operation of pusher 62 will be described further below.

In FIG. 28, pusher pin 916 can be seen to pass through pusher 62 and serves as an axis for pusher 62. Pusher pin 916, as shown in FIG. 27, is also attached to lever 16. Pressing lever 16 down causes pusher pin 916 to push locking link 904 down. Due to the stapler's scissor-like locking mechanism, this in turn causes anvil frame 900 to move down towards cartridge assembly 18 in the distal portion of chassis member 12. When locking link 904 arrives at its most extreme downward position it is locked in place by anvil locking element 906.

As discussed further below, the first press of lever 16 causes pusher pin 916 to move down and against locking link 904 so that link 904 locks against anvil locking element 906. When the pressure on lever 16 is released, pusher pin 916 moves up while locking link 904 remains locked in its substantially horizontal locked position. Subsequent presses of lever 16 cause pusher pin 916 to again move down so that pusher 62 engages with a tooth 68 of tooth rack 66.

Releasing the pressure on lever 16 causes pusher pin 916 to move up, while it causes pusher 62 to disengage from tooth rack 66 as described in greater detail below.

Figure 30:
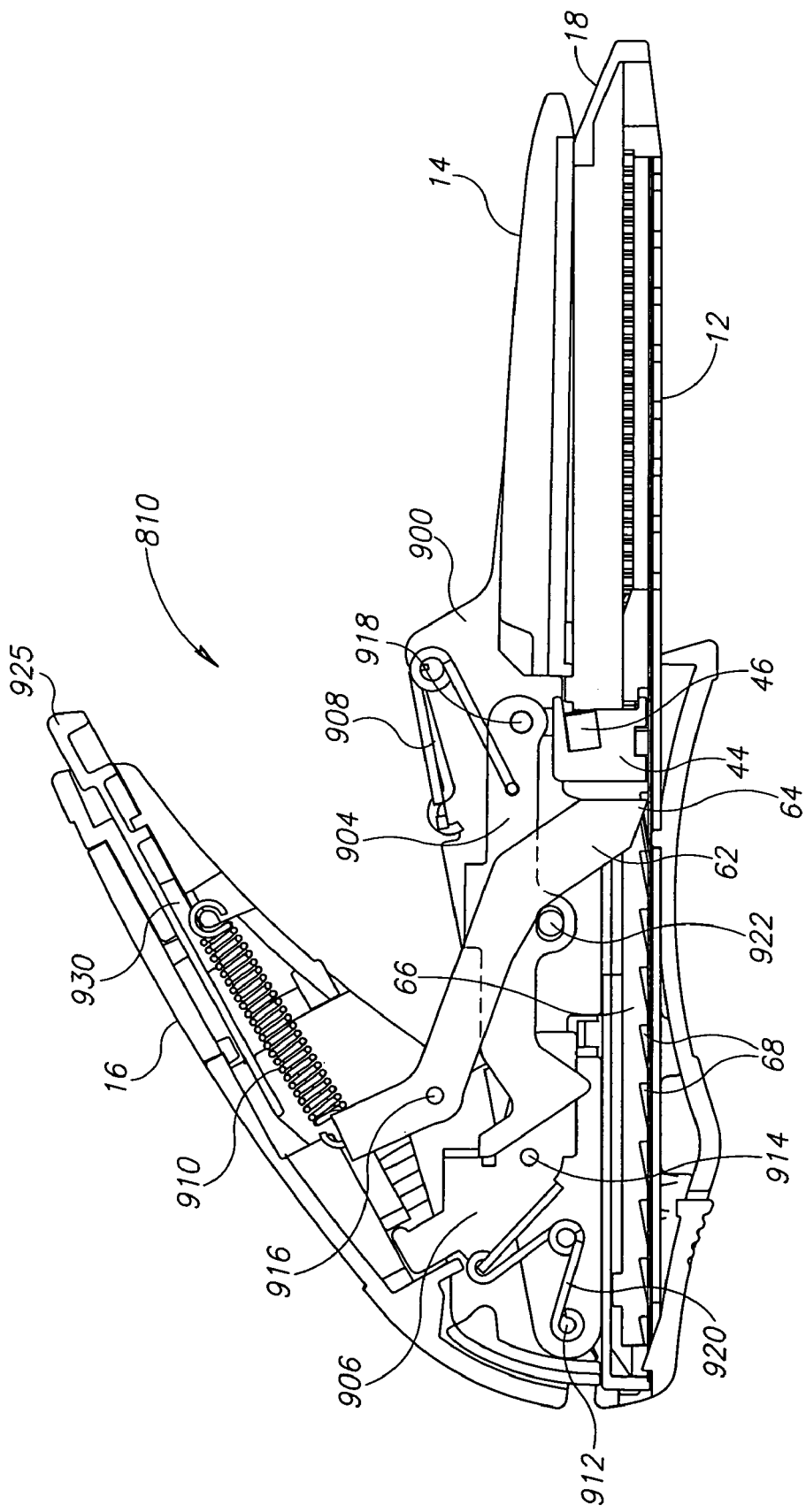
Figure 31:
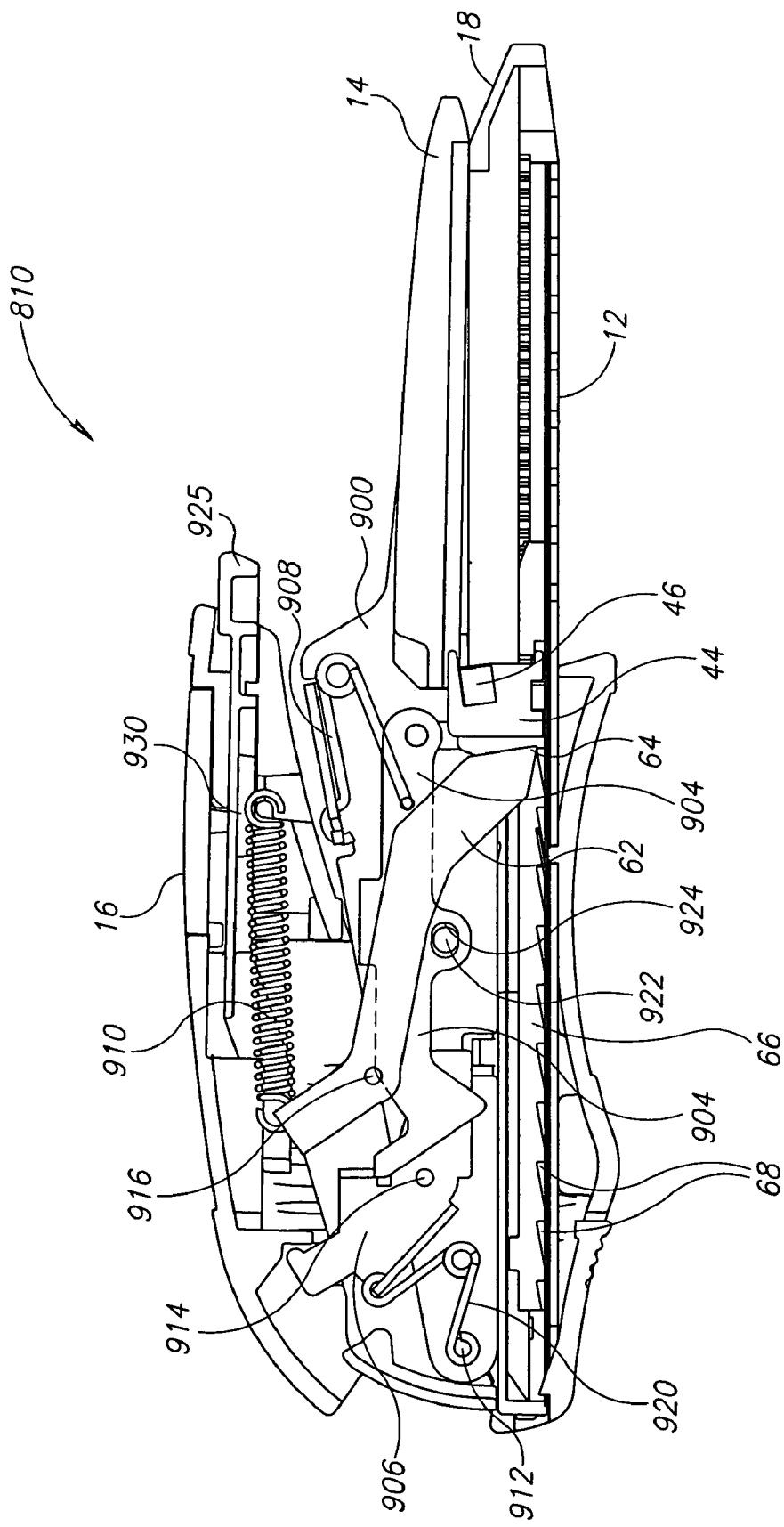
Figure 32:
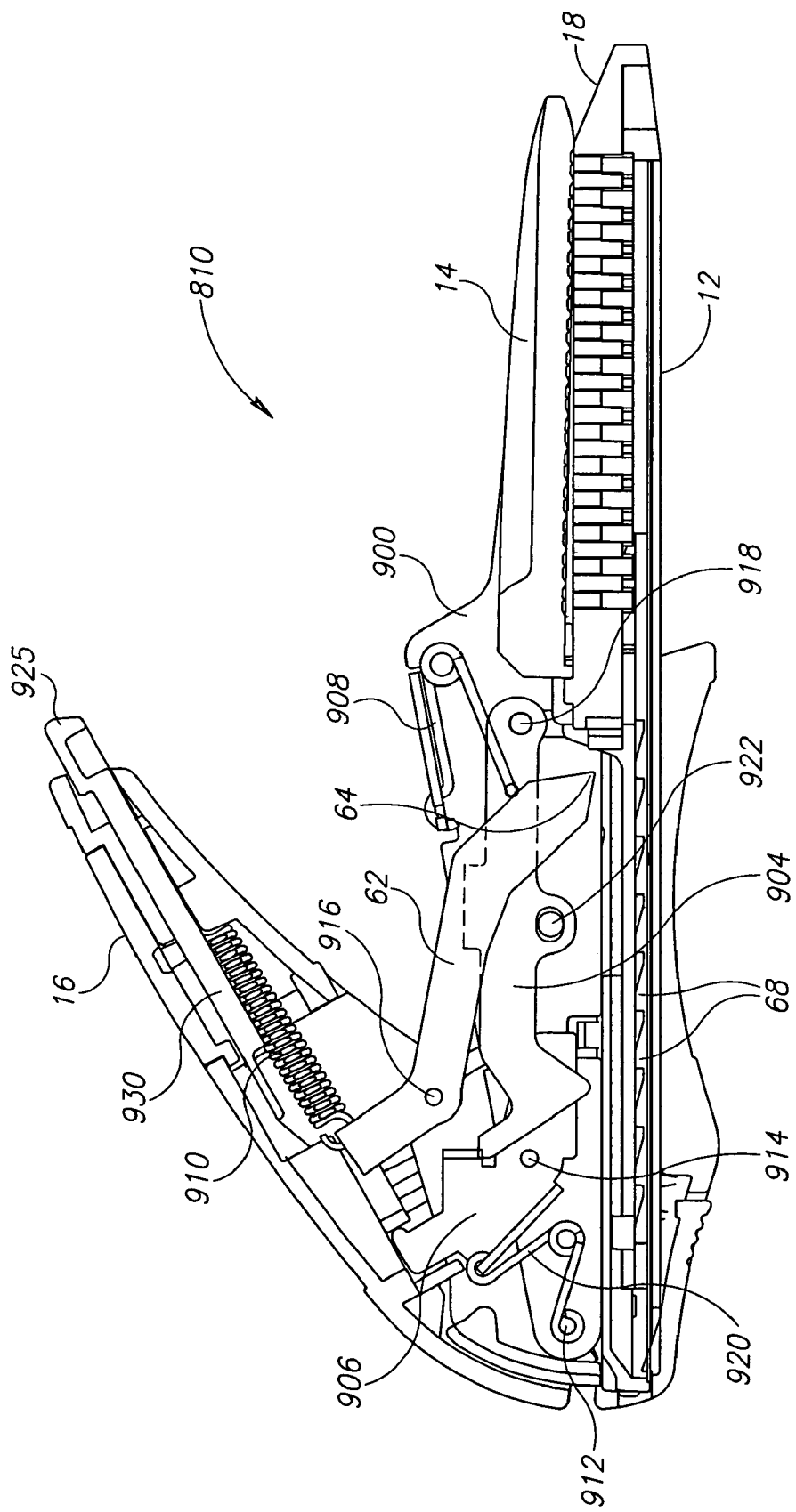

Stapler 810 is operated as follows:

1. After tissue (not shown) to be stapled and cut is positioned between anvil member 14 and cartridge assembly 18, the latter positioned at the extended distal portion of chassis member 12, lever 16 of stapler 810 is pressed. Lever 16 moves from it open position as shown in FIG. 28 to its closed position as shown in FIG. 29 by rotating in the direction of anvil member 14. As a result of this pressing action, pin 916 moves against locking link 904. Link 904 then moves down from its original substantially diagonal position (FIG. 28) and presses against anvil locking element 906. Element 906 immobilizes and locks locking link 904 and thereby also locks anvil member 14 in its closed position as shown in FIG. 29. When pressure on lever 16 is released, lever 16 returns to its original unpressed position (FIG. 30) because of the restorative force provided by lever spring 910. In FIG. 30, and in all subsequent figures other than FIG. 36, anvil member 14 is locked and held proximate to cartridge assembly 18 positioned in the distal portion of chassis member 12 with tissue held therebetween, and locking link 904 is held against anvil locking element 906.

Figure 33:
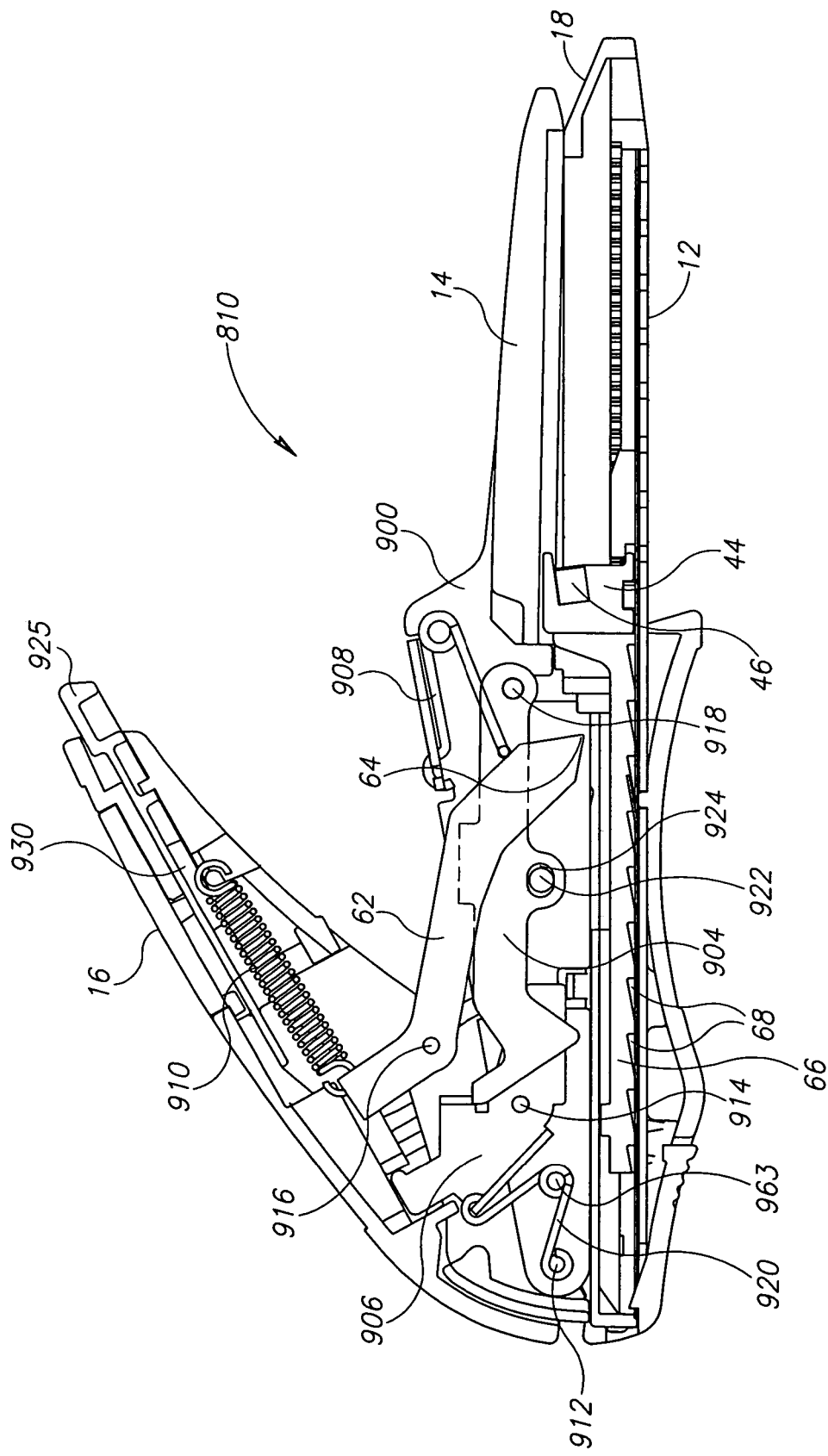

2. When lever 16 is pressed a second time (FIG. 31), the distal end 64 of pusher 62 engages with the distal-most tooth 68 of tooth rank 66. The pusher pushes the slider assembly (best seen in FIGS. 3A-3C as element 20) and tooth rack 66 forward by the distance between a pair of adjacent teeth 68. After release of lever 16, the lever returns to its original open position as in FIG. 32 while pusher 62 disengages from tooth rack 66. FIG. 33 is similar to FIG. 32 but better presents the advance of blade element 46 and blade member 44 resulting from the engagement and pushing action discussed and shown in conjunction with FIG. 31.

3. Lever 16 is pressed a third time and pusher 62 engages with the second most distal tooth 68 of tooth rank 66 (not shown). The engagement is very similar to that shown in FIG. 31 with the sole difference being the tooth being engaged by pusher 62. When engaged, the pusher pushes the slider assembly (best seen in FIGS. 3A-3C as element 20) and tooth rack 66 forward by the distance between a pair of adjacent teeth 68. After release of lever 16, the lever returns to its original open position as in FIG. 32 while pusher 62 disengages from tooth rack 66.

Figure 34:
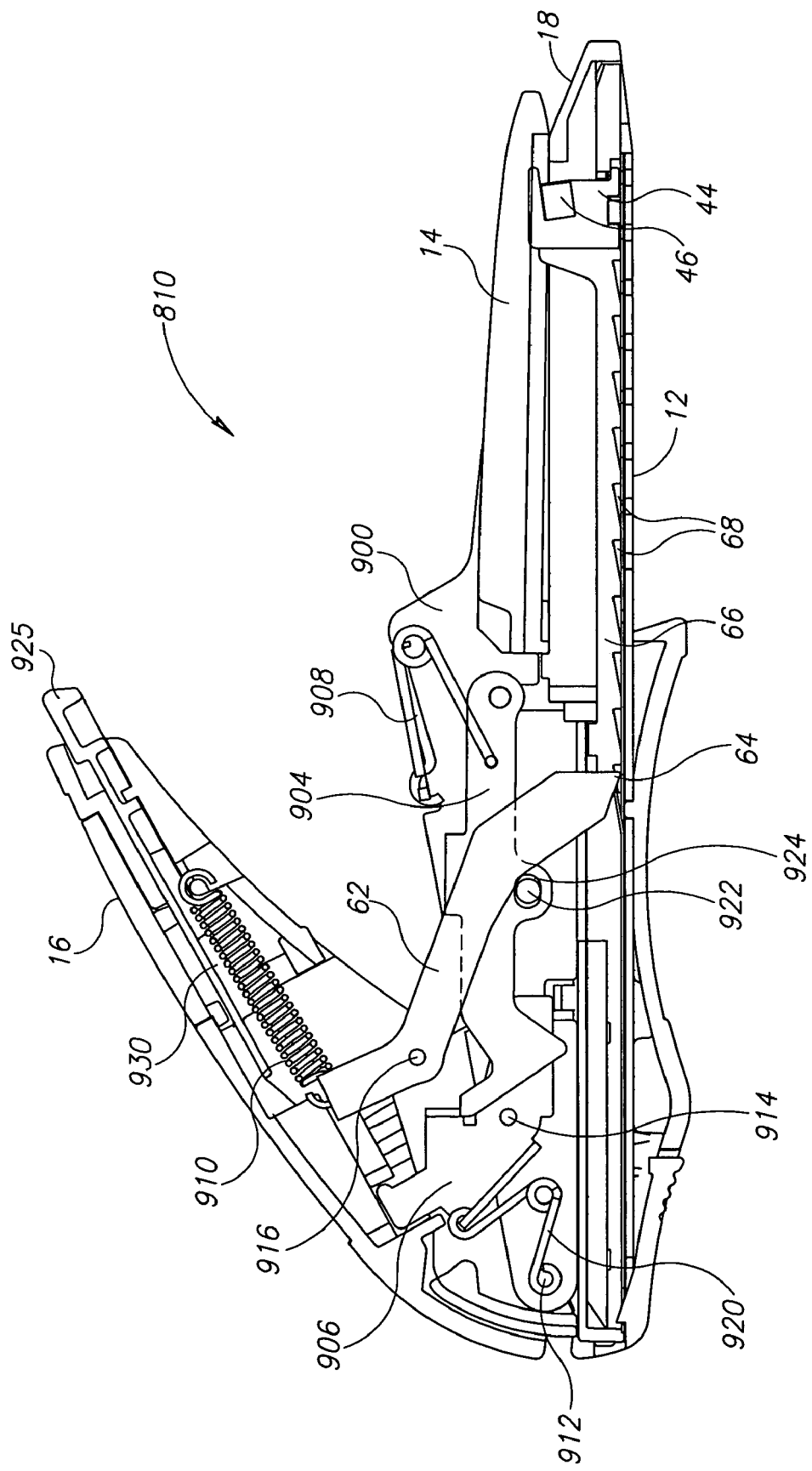

4. Step 3 is repeated several times until the wedge (best seen in FIGS. 3A-3C as element 48) and lifter (best seen in FIGS. 3A-3C as element 36) elements discussed above in conjunction with FIGS. 3-5A and elsewhere in the text reach the end of the staple cartridge (best seen in FIGS. 3A-3C as element 21) positioned in cartridge assembly 18. Distal end 64 of pusher 62 engages with the last tooth 68 of tooth rack 66 (FIG. 34). It should be noted that as described above in other embodiments with other figures, blade member 46 in blade holder 44 moves step-wise behind the wedge (best seen in FIGS. 3A-3C as element 48), the latter actuating the stapling operation. The tissue held between anvil member 14 and cartridge assembly 18 (in which the staples are positioned) is stapled and then very shortly thereafter cut by blade member 46.

Figure 35:
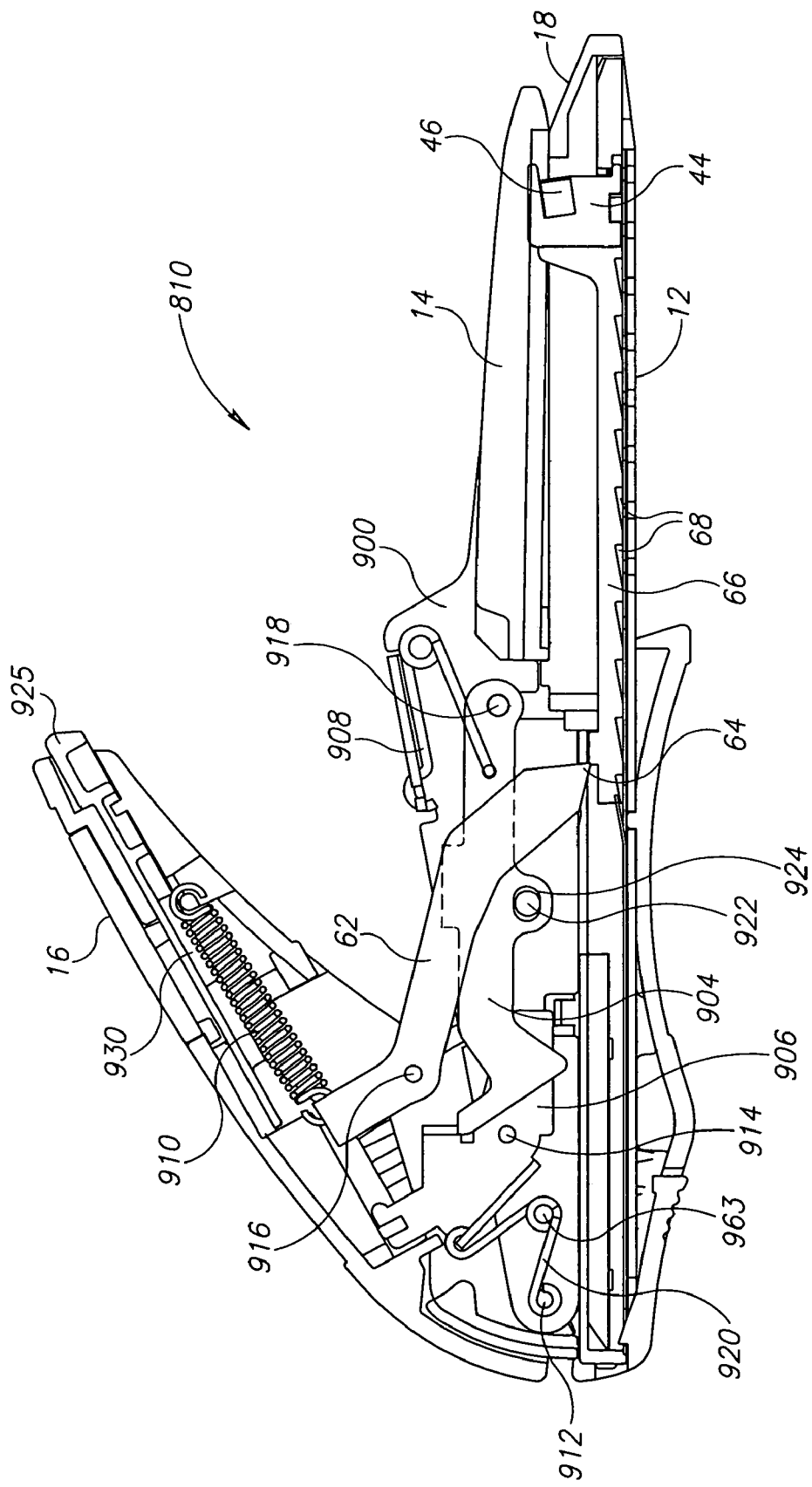

5. Lever 16 is released and pusher 62 is disengaged from tooth rack 66 (FIG. 35).

Figure 36:
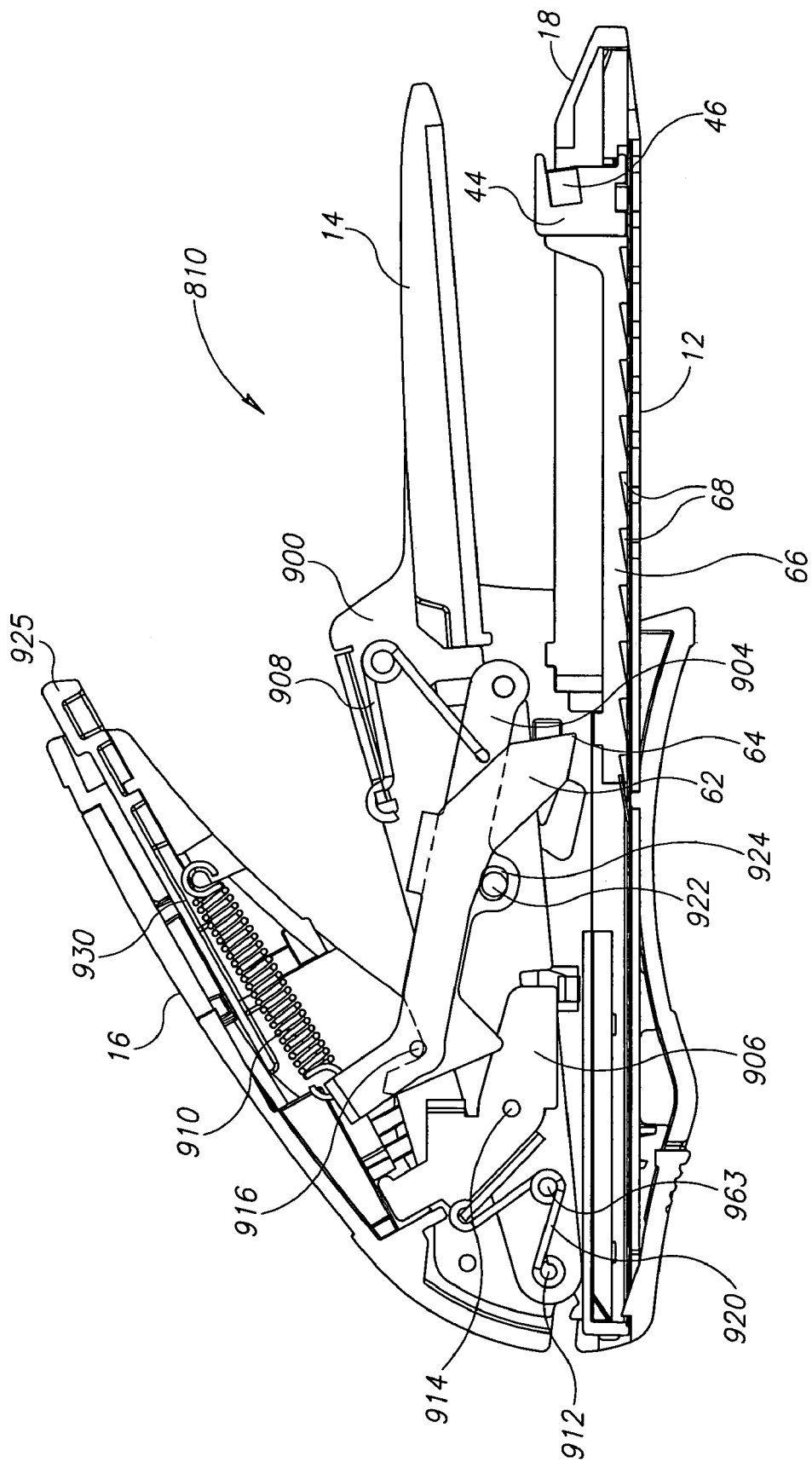

6. Release button 925 is then pushed. Release element 930, in operative association with release button 925, moves against and pushes anvil locking element 906. This in turn causes locking link 904 to move from its closed substantially horizontal position (e.g. FIG. 32) to its original unlocked substantially diagonal position (FIG. 28). Simultaneously, anvil locking link element 906 is returned by biased spring 920 to its original position and anvil member 14 rotates away from chassis member 12 (FIG. 36).

It should be noted that the tissue held between anvil member 14 and cartridge assembly 18 may be repositioned at any point during the stapler's stapling and cutting operation. This may be effected by pressing release button 925 as in step 6, repositioning the tissue, pressing the lever as in step 1 to lock the stapler's anvil member 14 in position and then proceeding with step 4 where pusher 62 reengages with tooth rack 66.

The above last described embodiment includes a scissor-like locking operation as opposed to the toggle locking mechanism used in previous embodiments and discussed therewith. One blade of the "scissors" is anvil member 14 joined to anvil frame 900; it extends from axis pin 912 to the distal end of anvil member 14. Pin 912 remains substantially stationary during operation of the stapler. The second blade of the "scissors" can be thought of as locking link 904. The proximal end of locking link 904 is held by locking link pin 918 and is therefore substantially immovable. During closing of the stapler, the distal end of anvil element 14 and the proximal end of locking link 904 move down, as does scissor pin 922. As noted above, pin 922 is fixed to anvil frame 900. Locking link 904 moves relative to scissor pin 922 due to the latter's freedom to move in oval aperture 924.

In stapler 810 shown and discussed in conjunction with FIGS. 27-36 no selector mechanism is required. It should be noted that the stapler embodiments shown and discussed in conjunction with FIGS. 1-26B may also have variations which do not require, and can be operated without, a selector button and mechanism. In some variations, the cut button shown therein may be replaced with a release button as in the embodiment shown in FIGS. 27-36.

As with previous embodiments, the tissue stapler of this last embodiment can be used on bowel tissue and, with little or no modification, on tissue of other organs as well. Such other organs include, but are not limited to, the uterus, esophagus and lungs.

Similarly, it should be readily apparent to one skilled in the art that the device and method of the present invention can be used to excise tissue of animals as well as humans particularly, but without being limiting, other mammalian species.

It will be appreciated by persons skilled in the art that the present invention is not limited by the drawings and description hereinabove presented. Rather, the invention is defined solely by the claims that follow.

What is claimed is:

1. A palm-size stapler for hand-assisted laparoscopic and open surgery comprising:
   a) a chassis member in which at least the following elements are supported:
      i) a cartridge assembly for containing at least two rows of staples; and
      ii) a slider assembly operative to slidably move along a predetermined path with respect to said cartridge assembly, thereby to provide a predetermined staple ejection force to cause the ejection of staples from said cartridge assembly, said slider assembly including:
         at least one staple ejector element aligned with said at least two rows of staples for causing ejection of the staples;
   b) an anvil member operable in closed and open positions with respect to said cartridge assembly and when in a closed position said anvil member is spaced from said cartridge assembly so as to hold a portion of tissue to be stapled therebetween and to allow closure of staples ejected into the tissue from said cartridge assembly in response to the predetermined staple ejection force provided by said slider assembly;

c) a lever member mounted to said chassis member pivotably movable with respect to said cartridge assembly and operable by using one hand; and d) a locking mechanism operable in locked and unlocked positions and in operative association with said anvil member, said locking mechanism being brought to its locked position when said lever member is pressed and brought down, and when said locking mechanism is brought to its locked position said anvil member is brought to and locked in its closed position and held adjacent to said cartridge assembly during subsequent operation, thereby to allow closure of staples in the portion of the tissue held between said cartridge assembly and said anvil member as said slider assembly advances step-wise incrementally ejecting staples into the tissue with each step.

2. A stapler according to claim 1, further including an incremental drive mechanism operative to engage with and to provide a predetermined driving force to said slider assembly causing an incremental step-wise sliding motion thereof, said incremental drive mechanism allowing for interruption of the operation of said stapler during surgery and allowing for repositioning of the tissue being stapled when said locking mechanism is released by a release mechanism, said release mechanism in operative association with said locking mechanism, said anvil member being brought to its open position from its closed position after release of said locking mechanism.

3. A stapler according to claim 2, wherein said anvil member is connected rigidly to an anvil frame thereby to form therewith an extended substantially rigid compound anvil member, wherein said compound anvil member extends from an axis pin positioned near the proximal end of said stapler to the distal end of said anvil member, and said compound anvil member is hingedly mounted on said axis pin.

4. A stapler according to claim 3, wherein said locking mechanism further comprises a pusher pin, a locking link and an anvil locking element, said locking link in operational engagement with said compound anvil member allowing scissor-like motion therebetween, and said pusher pin positioned on said lever member, said pusher pin moving downward in a direction generally toward said slider assembly when said lever member is depressed, and moving upward in a direction generally away from said slider assembly when the said lever is released, and wherein said pusher pin is operative, when moving downward, to push said locking link against said anvil locking element so as to become engaged therewith and so as to hold said anvil member in said closed position after depression of said lever member until activation of said release mechanism.

5. A stapler according to claim 4, wherein said incremental drive mechanism is a pusher-ratchet mechanism that comprises a.) a pusher positioned obliquely to said ratchet mechanism and b.) a ratchet mechanism, wherein said ratchet mechanism is formed as part of said slider assembly, and said pusher is mounted for pivoting about an axis extending substantially transversally therethough and also extending substantially through said pusher pin.

6. A stapler according to claim 5, wherein said pusher is operatively associated with a slidable tooth rack so as to incrementally move said slider assembly of said stapler along a predetermined path in a stepped fashion.

7. A stapler according to claim 2, wherein said incremental drive mechanism is a pusher-ratchet mechanism that comprises a.) a pusher positioned obliquely to said ratchet mechanism and b.) a ratchet mechanism, wherein said ratchet mechanism is formed as part of said slider assembly, and said pusher is mounted for pivoting about an axis extending substantially transversally therethough and also extending substantially through a pusher pin positioned on said lever member.

8. A stapler according to claim 1, wherein said cartridge assembly is configured to hold a cartridge of staples, and said anvil member has proximal and distal surfaces with respect to said cartridge assembly, said proximal surface having therein a plurality of recesses formed to be in registration with the staples in said cartridge in said cartridge assembly, and configured to retain the plurality of staples in a planar arrangement during and subsequent to crimping of the staples.

9. A stapler according to claim 1, further including a blade element attached to said slider assembly, operative to advance in incremental steps corresponding to the advance of said slider assembly in incremental steps, thereby to incrementally cut through the tissue held between said anvil member and said cartridge assembly in accordance with the advance of said slider assembly.

10. A stapler according to claim 1, wherein said locking mechanism further comprises a pusher pin, a locking link and an anvil locking element, said locking link in operational engagement with said anvil member allowing scissor-like motion therebetween, and said pusher pin positioned on said lever member, said pusher pin moving downward in a direction generally toward said slider assembly when said lever member is depressed, and moving upward in a direction generally away from said slider assembly when the said lever is released, and wherein said pusher pin is operative, when moving downward, to push said locking link against said anvil locking element so as to become engaged therewith and so as to hold said anvil member in said closed position after depression of said lever member until activation of a release mechanism which is in operational communication with said anvil locking element and which operates to release said locking mechanism bringing it from its locked to its unlocked position.

11. A palm-size stapler for hand-assisted laparoscopic and open surgery comprising:

a) a chassis member in which at least the following elements are supported:
 i) a cartridge assembly for containing at least two rows of staples; and
 ii) a slider assembly operative to slidably move along a predetermined path with respect to said cartridge assembly, thereby to provide a predetermined staple ejection force to cause the ejection of staples from said cartridge assembly, said slider assembly including:
  at least one staple ejector element aligned with said at least two rows of staples for causing ejection of the staples;

b) a lever member mounted to said chassis member pivotably movable with respect to said cartridge assembly and operable by using one hand;

c) an anvil member operable in closed and open positions with respect to said cartridge assembly and when in closed position said anvil member is spaced from said cartridge assembly so as to hold a portion of tissue being stapled therebetween, and to allow closure of staples ejected into the tissue from said cartridge assembly in response to the predetermined staple ejection force provided by said slider assembly; and d) an incremental drive mechanism in operational association with said slider assembly, said drive mechanism operative to engage with and to provide a predetermined driving force to said slider assembly causing an incremental step-wise sliding motion thereof, said incremental drive mechanism also allowing for interruption of the operation of said device during surgery and allowing repositioning of the portion of tissue being stapled.

12. A stapler according to claim 11, wherein said anvil member is connected rigidly to an anvil frame thereby to form therewith an extended substantially rigid compound anvil member, wherein said compound anvil member extends from an axis pin positioned near the proximal end of said stapler to the distal end of said anvil member, and said compound anvil member is hingedly mounted on said axis pin.

13. A stapler according to claim 12, further including a locking mechanism operable in locked and unlocked positions and in operative association with said anvil member, said locking mechanism brought to its locked position when said lever member is pressed and brought down, and when said locking mechanism is brought to its locked position said anvil member is brought to its closed position and held adjacent to said cartridge assembly during subsequent stapler operation until a release mechanism in operative association with said locking mechanism is activated unlocking said locking mechanism thereby allowing said anvil member to pivot away from said cartridge assembly.

14. A stapler according to claim 12, wherein said locking mechanism further comprises a pusher pin, a locking link and an anvil locking element, said locking link in operational engagement with said compound anvil member allowing scissor-like motion therebetween, and said pusher pin positioned on said lever member, said pusher pin moving downward in a direction generally toward said slider assembly when said lever member is depressed, and moving upward in a direction generally away from said slider assembly when said lever is released, and wherein said pusher pin is operative when moving downward to push said locking link against said anvil locking element so as to become engaged therewith and so as to hold said anvil member in said closed position after depression of said lever member until activation of said release mechanism which operates to release said locking mechanism bringing it from its locked to its unlocked position.

15. A stapler according to claim 14, wherein said incremental drive mechanism is a pusher-ratchet mechanism that comprises a.) a pusher positioned obliquely to said ratchet mechanism and b.) a ratchet mechanism, wherein said ratchet mechanism is formed as part of said slider assembly, and said pusher is mounted for pivoting about an axis extending substantially transversally therethough and also extending substantially through said pusher pin.

16. A stapler according to claim 15, wherein said pusher is operatively associated with a slidable tooth rack so as to incrementally move said slider assembly of said stapler along a predetermined path in a stepped fashion.

17. A stapler according to claim 11, wherein said cartridge assembly is configured to hold a cartridge of staples, and said anvil member has proximal and distal surfaces with respect to said cartridge assembly, said proximal surface having therein a plurality of recesses formed to be in registration with the staples in said cartridge in said cartridge assembly, and configured to retain the plurality of staples in a planar arrangement during and subsequent to crimping of the staples.

18. A stapler according to claim 11, further including a blade element attached to said slider assembly, operative to advance in incremental steps corresponding to the advance of said slider assembly in incremental steps, thereby to incrementally cut through the tissue held between said anvil member and said cartridge assembly in accordance with the advance of said slider assembly.

19. A stapler according to claim 11, wherein said incremental drive mechanism is a pusher-ratchet mechanism that comprises a.) a pusher positioned obliquely to said ratchet mechanism and b.) a ratchet mechanism, wherein said ratchet mechanism is formed as part of said slider assembly, and said pusher is mounted for pivoting about an axis extending substantially transversally therethrough and also extending substantially through a pusher pin positioned on said lever member.

20. A stapler according to claim 11, further including a locking mechanism which comprises a pusher pin, a locking link and an anvil locking element, said locking link in operational engagement with said anvil member allowing scissor-like motion therebetween, and said pusher pin positioned on said lever member, said pusher pin moving downward in a direction generally toward said slider assembly when said lever member is depressed, and moving upward in a direction generally away from said slider assembly when said lever is released, and wherein said pusher pin is operative when moving downward to push said locking link against said anvil locking element so as to become engaged therewith and so as to hold said anvil member in said closed position after depression of said lever member until activation of a release mechanism which is in operational communication with said anvil locking element and which operates to release said locking mechanism bringing it from its locked to its unlocked position.

* * * * *